US008404829B2

(12) United States Patent
Gray et al.

(10) Patent No.: US 8,404,829 B2
(45) Date of Patent: Mar. 26, 2013

(54) PREDICTIVE AND THERAPEUTIC MARKERS IN OVARIAN CANCER

(75) Inventors: Joe W. Gray, San Francisco, CA (US); Yinghui Guan, South San Francisco, CA (US); Wen-Lin Kuo, San Ramon, CA (US); Jane Fridlyand, San Francisco, CA (US); Gordon B. Mills, Houston, TX (US)

(73) Assignees: The Regents of the University of California, Oakland, CA (US); The Board of Regents, University of Texas System, Austin, TX (US)

( * ) Notice: Subject to any disclaimer, the term of this patent is extended or adjusted under 35 U.S.C. 154(b) by 124 days.

(21) Appl. No.: 11/814,798

(22) PCT Filed: Jan. 19, 2006

(86) PCT No.: PCT/US2006/002202
§ 371 (c)(1),
(2), (4) Date: Jul. 23, 2008

(87) PCT Pub. No.: WO2006/081158
PCT Pub. Date: Aug. 3, 2006

(65) Prior Publication Data
US 2008/0312096 A1 Dec. 18, 2008

Related U.S. Application Data

(60) Provisional application No. 60/647,183, filed on Jan. 25, 2005.

(51) Int. Cl.
*C07H 20/04* (2006.01)
*C07H 21/02* (2006.01)
*A61K 48/00* (2006.01)

(52) U.S. Cl. .................. 536/24.5; 536/23.1; 514/44

(58) Field of Classification Search ............ 435/6, 91.1, 435/91.31, 455; 514/44; 536/23.1, 24.5
See application file for complete search history.

(56) References Cited

U.S. PATENT DOCUMENTS
2002/0068709 A1 * 6/2002 Orum et al. .................. 514/44
2004/0023267 A1 2/2004 Morris

FOREIGN PATENT DOCUMENTS
WO WO 03/006477 * 1/2003
WO WO 03/080808 * 10/2003

OTHER PUBLICATIONS

Rack et al (Genes, Chromosomes & Cancer, 1998, 23:220-226).*
Shtivelman et al., Molecular and Cellular Biology, vol. 10, No. 4, pp. 1835-1839 (1990).*
Khvorova et al., Cell, vol. 115, pp. 209-216 (2003).*
Crooke, S., Ann. Rev. Medicine, vol. 55, pp. 61-95 (2004).*
Peracchi et al., Rev. Med. Virol., vol. 14, pp. 47-64 (2004).*
Agrawal et al., Molecular Med. Today,vol. 6, pp. 72-81 (2000).*
Chirila, et al., Biomaterials, vol. 23, pp. 321-342 (2002).*
Opalinska et al., Nature Rev., vol. 1, pp. 503-514 (2002).*
Jang et al., Expert Rev. Medical Devices, vol. 1, No. 1, pp. 127-138 (2004).*
Storlazzi, et al., "Identification of a commonly amplified 4.3 Mb region with overexpression of *C8FW*, but not *MYC* in *MYC*-containing double minutes in myeloid malignancies," *Human Molecular Genetics*, vol. 13 (14):pp. 1479-1485, (May 26, 2004).
Suzuki, et al., "An approach to analysis of large-scale correlations between genome changes and clinical endpoints in ovarian cancer," *Cancer Research.*, vol. 60, pp. 5382-5385, (Oct. 1, 2000).

\* cited by examiner

*Primary Examiner* — Amy Bowman
(74) *Attorney, Agent, or Firm* — Michelle Chew Wong; Lawrence Berkeley National Laboratory

(57) ABSTRACT

Cancer markers may be developed to detect diseases characterized by increased expression of apoptosis-suppressing genes, such as aggressive cancers. Genes in the human chromosomal regions, 8q24, 11q13, 20q11-q13, were found to be amplified indicating in vivo drug resistance in diseases such as ovarian cancer. Diagnosis and assessment of amplification levels certain genes shown to be amplified, including PVT1, can be useful in prediction of poor outcome of patient's response and drug resistance in ovarian cancer patients with low survival rates. Certain genes were found to be high priority therapeutic targets by the identification of recurrent aberrations involving genome sequence, copy number and/or gene expression are associated with reduced survival duration in certain diseases and cancers, specifically ovarian cancer. Therapeutics to inhibit amplification and inhibitors of one of these genes, PVT1, target drug resistance in ovarian cancer patients with low survival rates is described.

3 Claims, 17 Drawing Sheets

Fig. 4
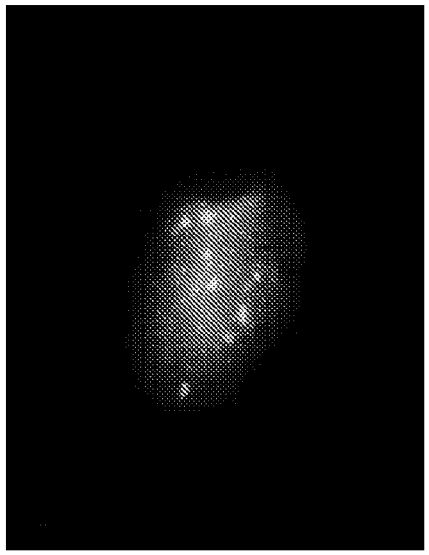
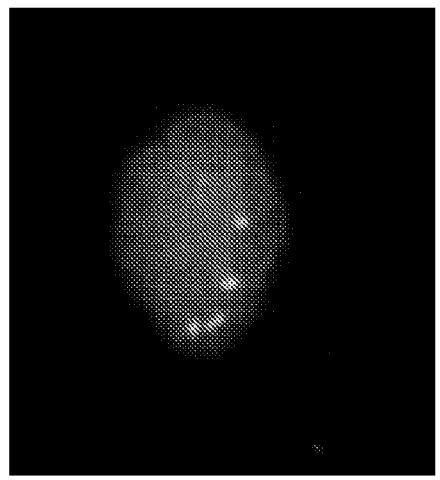
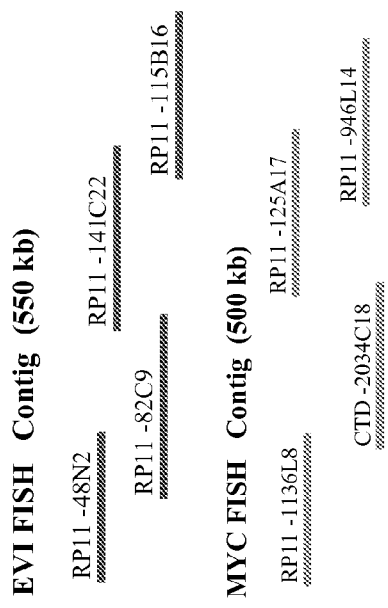
EVI FISH Contig (550 kb)
RP11-48N2   RP11-141C22
    RP11-82C9        RP11-115B16
MYC FISH Contig (500 kb)
RP11-1136L8   RP11-125A17
    CTD-2034C18   RP11-946L14
A          B          C Effects on Cell Cycle of PVT1siRNA in Cell Lines Overexpressing PVT1

Effects on Cell Cycle of PVT1siRNA in Cell Lines Not Expressing PVT1

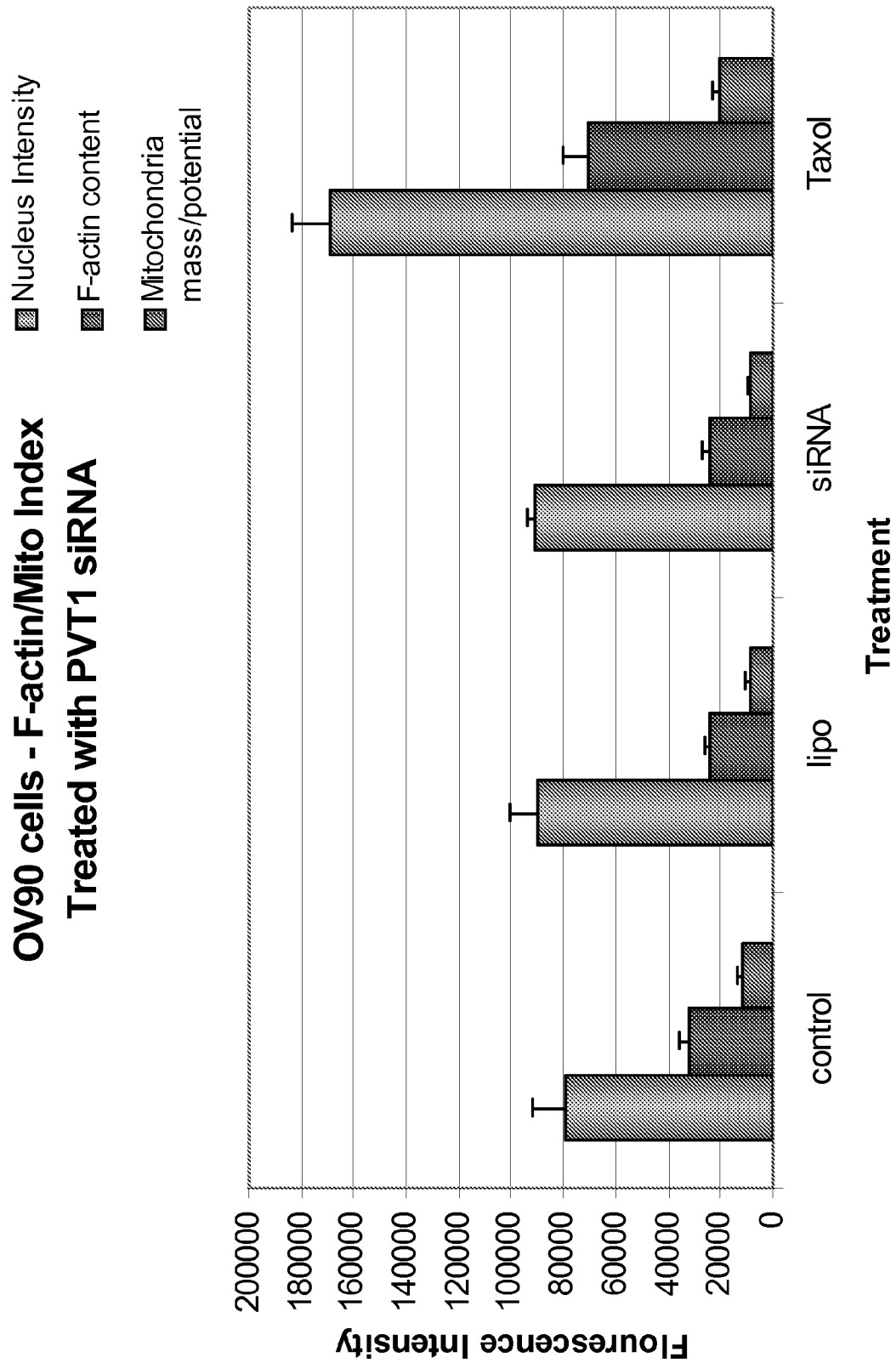

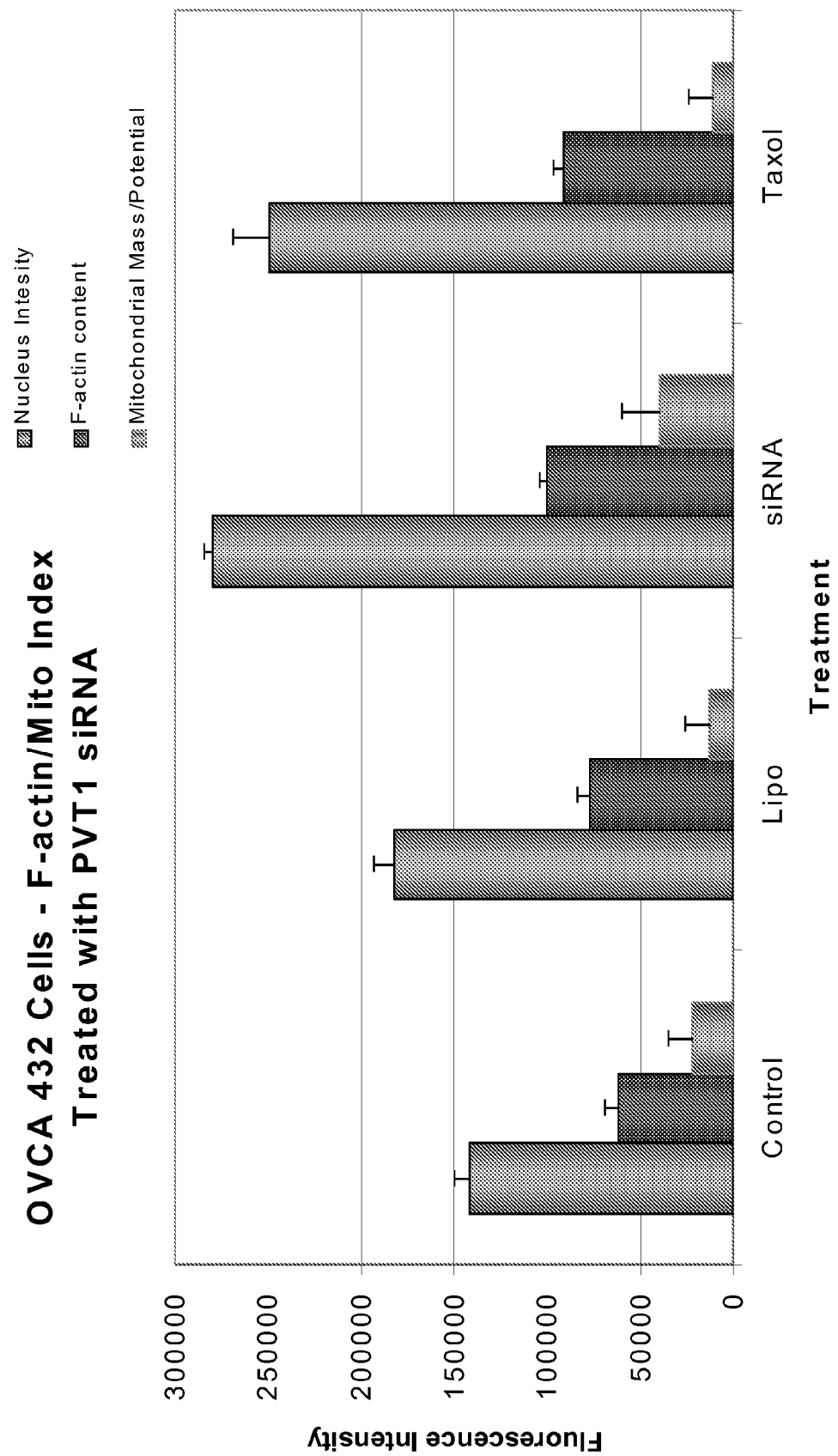

Myc amplicon May/04 freeze, chr8:128,624,346-129,818,226bp

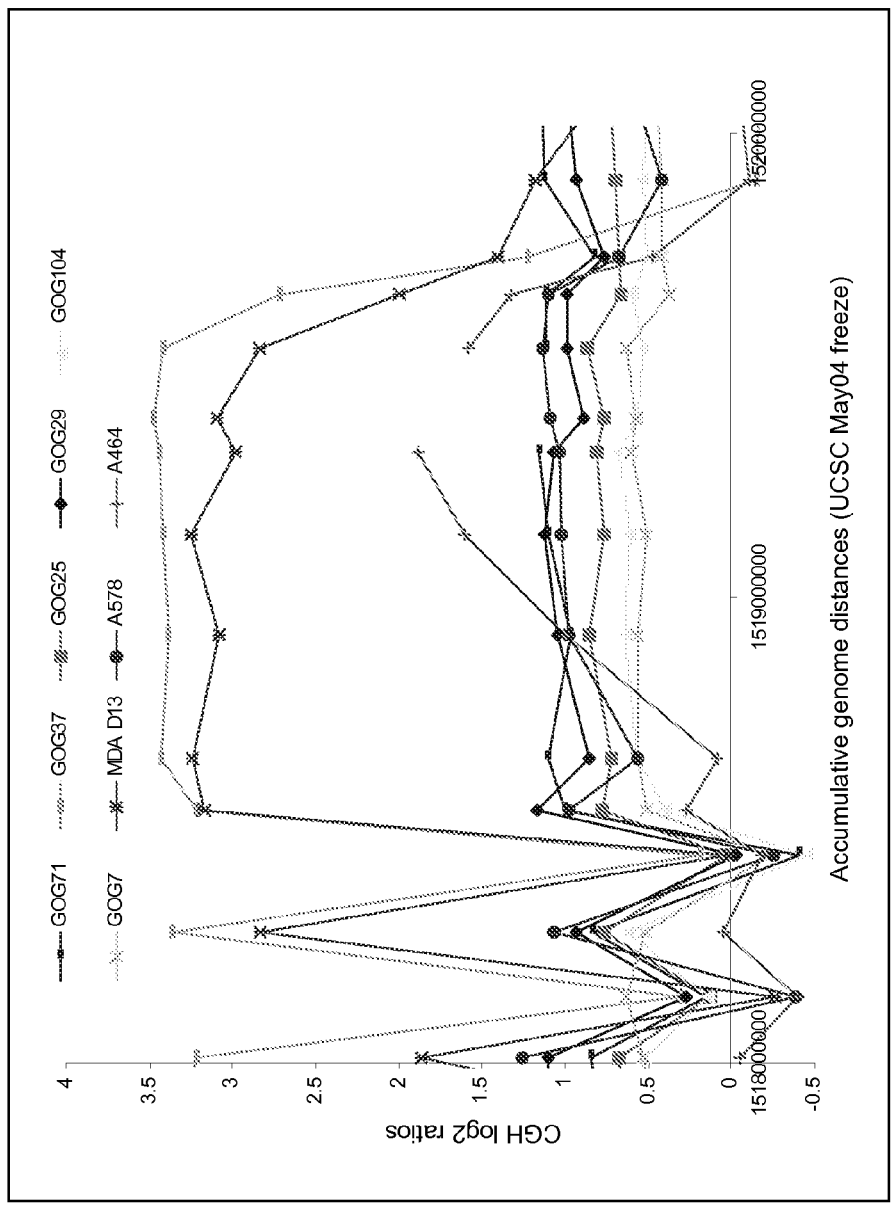

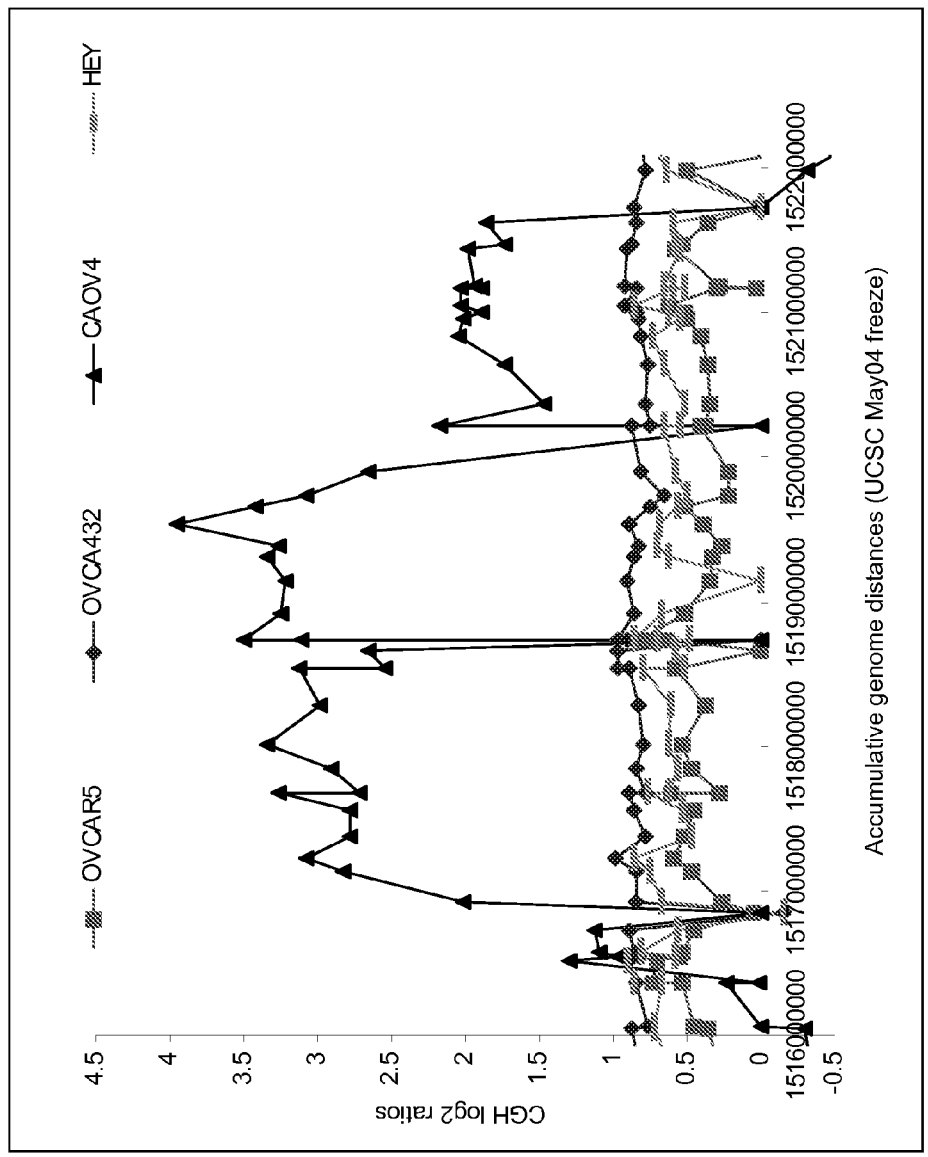

```
                        SEQUENCE LISTING

<160> NUMBER OF SEQ ID NOS: 23

<210> SEQ ID NO 1
<211> LENGTH: 1536
<212> TYPE: DNA
<213> ORGANISM: Homo sapiens

<400> SEQUENCE: 1
cgagcacatg ggccgcgggc cgggcgggct cggggcggcc gggacgagga ggggcgacga      60
cgagctgcga gcaaagatgt gccccgggac ccccggcacc ttccagtgga tttccttgcg     120
gaaaggatgt tggcggtccc tgtgacctgt ggagacacgg ccagatctgc cctccagcct     180
gatcttttgg ccagaaggag attaaaaaga tgcccctcaa gatggctgtg ctgtcagctg     240
catggagctt cgttcaagta ttttctgagc ctgatggatt tacagtgatg ttcagtggtc     300 tgggaataa cgctggtgga accatgcact ggaatgacac acgcccggca catttcagga     360
tactaaaagt ggttttaagg gaggctgtgg ctgaatgcct catggattct tacagcttgg     420
atgtccatgg gggacgaagg actgcagctg gctgagaggg ttgagatctc tgtttactta     480
gatctctgcc aacttccttt gggtctccct atggaatgta agacccgac tcttcctggt      540 gaagcatctg atgcacgttc catccggcgc tcagctgggc ttgagctgac catactccct     600
ggagccttct cccgaggtgg gcgggtgacc ttggcacata cagccatcat gatggtactt     660
taagtggagg ctgaatcatc tccccttga gctgctttgg gaacgtggcc cccttggtgt      720 tccccttta ctgccaggac actgagattt ggagaggtaa gtggcttacc tgaggccatg     780
```

-continued

```
tgctaacaga gaagatgaag agatgattga acaggccta agaccagacc taagggtctg      840 tacatttttcc acatactttc catatctttta gaggcctgac caaagcagat cttttccttt   900
cttctaggta agtccaaagg cacctgcctg ctgggcccac tgttttctaa ctttcctaac     960
tttctgatcc cttggaggtg ataatcaaat attctagtct gaggcattgg gatacatggt    1020
gctaggttct gagactctgc gtcaggcctg aaccctgcat tttgtggagg tgggtgggag    1080
aatgttcccc tggggaacat gcctagacac ggggacaac agttgccctc atggggaggt     1140
acctgtttac tcgctgttat ggaccgctt tcacaaaacc actgcaggtg agtgagttcc     1200
tgctgaatat caggcctggt gtctctagac tcattattcc cccacccaac ccctatgtta    1260
gttcatctcg agccacattt ttattgccat aatccaggcc tggacaggcc aagatctttt    1320
aacaatttta attactgaaa ataataactg cattttttttt taaagcccaa cttttttggta  1380 agtcagccca aaatacagtc tttgtgttgc catctgggaa ctggatttgg aattgttctt    1440
ccatgagact gcagagcaga acggcagggc cagaggtccc acgagctggt cagacccggt    1500
tctgctcctt gctggctgag tgaccttggg cattgt                              1536
```

<210> SEQ ID NO 2
<211> LENGTH: 1100
<212> TYPE: DNA
<213> ORGANISM: Homo sapiens

<400> SEQUENCE: 2

```
acgaggaggg gcgacgacga gctgcgagca aagatgtgcc ccgggacccc cggcaccttc      60
cagtggattt ccttgcggaa aggatgttgg cggtccctgt gacctgtgga gacacggcca    120
gatctgccct ccagcctgat cttttggcca aaggagatt aaaaagatgc ccctcaagat     180
ggctgtgcct gtcagctgca tggagcttcg ttcaagtatt ttctgagcct gatggattta   240
cagtgatctt cagtggtctg gggaataacg ctggtggaac catgcactgg aatgacacac    300
gcccggcaca tttcaggata ctaaaagtgg ttttaaggga ggctgtggct gaatgcctca    360
tggattctta cagcttggat gtccatgggg gacgaaggac tgcagctggc tgagagggtt    420
gagatctctg tttacttaga tctctgccaa cttccttttgg gtctccctat ggaatgtaag   480
accccgactc ttcctggtga agcatctgat gcacgttcca tccggcgctc agctgggctt    540
gagattcctg gaacaccac catggagggc ctggcctttg gcgtggaca gtctgtggct     600 gggtgggaac gtcaggagtg gggcctgcct ctttgctggg aatgccgtgc actcccagcc    660
cacttgcccc atgccagcac tcgaggcagg acttcgcagc tgaccatact ccctggagcc    720
ttctcccgag gtgcgcgggt gaccttggca catacagcca tcatgatggt actttaagtg    780
gaggctgaat catctcccct ttgagctgct tggcacgtgg ctcccttggt gttcccttt     840 tactgccagg acactgagat ttggagaggc aactacacag ccagtggtgg gaaagcacct    900
aatttacatc ttcatgcatt gaaactgatg tcactcacct ctccccttg acctggaaga    960 gccctgaag gctgccatag ggaaatgat aacccattct acagctgctg aaactgaggc     1020
ccagggagtg tccagagctt tctgaggtcc accatgtact gttgaccagg atgagtgata   1080
gccacctggt gacaatgttg                                               1100
```

<210> SEQ ID NO 3
<211> LENGTH: 19
<212> TYPE: RNA
<213> ORGANISM: Artificial
<220> FEATURE:
<223> OTHER INFORMATION: siRNA sense sequence

```
<400> SEQUENCE: 3
cagccaucau gaugguacu                                                    19

<210> SEQ ID NO 4
<211> LENGTH: 19
<212> TYPE: RNA
<213> ORGANISM: Artificial
<220> FEATURE:
<223> OTHER INFORMATION: siRNA antisense sequence

<400> SEQUENCE: 4
aguaccauca ugauggcug                                                    19

<210> SEQ ID NO 5
<211> LENGTH: 21
<212> TYPE: RNA
<213> ORGANISM: Artificial
<220> FEATURE:
<223> OTHER INFORMATION: siRNA sense sequence

<400> SEQUENCE: 5
ccggcacauu ucaggauacu a                                                 21

<210> SEQ ID NO 6
<211> LENGTH: 21
<212> TYPE: RNA
<213> ORGANISM: Artificial
<220> FEATURE:
<223> OTHER INFORMATION: siRNA sense sequence

<400> SEQUENCE: 6
accaugcacu ggaaugacac a                                                 21

<210> SEQ ID NO 7
<211> LENGTH: 21
<212> TYPE: RNA
<213> ORGANISM: Artificial
<220> FEATURE:
<223> OTHER INFORMATION: siRNA sense sequence

<400> SEQUENCE: 7
gcugcaugga gcuucguuca a                                                 21

<210> SEQ ID NO 8
<211> LENGTH: 21
<212> TYPE: RNA
<213> ORGANISM: Artificial
<220> FEATURE:
<223> OTHER INFORMATION: siRNA sense sequence

<400> SEQUENCE: 8
agcaucugau gcacguucca u                                                 21

<210> SEQ ID NO 9
<211> LENGTH: 21
<212> TYPE: RNA
<213> ORGANISM: Artificial
<220> FEATURE:
<223> OTHER INFORMATION: siRNA antisense sequence

<400> SEQUENCE: 9
auggaacgug caucagaugc u                                                 21

<210> SEQ ID NO 10
<211> LENGTH: 21
<212> TYPE: RNA
```

```
<213> ORGANISM: Artificial
<220> FEATURE:
<223> OTHER INFORMATION: siRNA sense sequence

<400> SEQUENCE: 10
ggacuucgca gcugaccaua c                                              21

<210> SEQ ID NO 11
<211> LENGTH: 21
<212> TYPE: RNA
<213> ORGANISM: Artificial
<220> FEATURE:
<223> OTHER INFORMATION: siRNA antisense sequence

<400> SEQUENCE: 11
guauggucag cugcgaaguc c                                              21

<210> SEQ ID NO 12
<211> LENGTH: 21
<212> TYPE: RNA
<213> ORGANISM: artificial
<220> FEATURE:
<223> OTHER INFORMATION: siRNA sense sequence

<400> SEQUENCE: 12
cauacagcca ucaugauggu a                                              21

<210> SEQ ID NO 13
<211> LENGTH: 21
<212> TYPE: RNA
<213> ORGANISM: artificial
<220> FEATURE:
<223> OTHER INFORMATION: siRNA antisense sequence

<400> SEQUENCE: 13
uaccaucaug auggcuguau g                                              21

<210> SEQ ID NO 14
<211> LENGTH: 21
<212> TYPE: RNA
<213> ORGANISM: artificial
<220> FEATURE:
<223> OTHER INFORMATION: siRNA sense sequence

<400> SEQUENCE: 14
ggugaagcau cugaugcacg u                                              21

<210> SEQ ID NO 15
<211> LENGTH: 21
<212> TYPE: RNA
<213> ORGANISM: artificial
<220> FEATURE:
<223> OTHER INFORMATION: siRNA antisense sequence

<400> SEQUENCE: 15
acgugcauca gaugcuucac c                                              21

<210> SEQ ID NO 16
<211> LENGTH: 21
<212> TYPE: RNA
<213> ORGANISM: artificial
<220> FEATURE:
<223> OTHER INFORMATION: siRNA sense sequence

<400> SEQUENCE: 16
gacuucgcag cugaccauac u                                              21
```

```
<210> SEQ ID NO 17
<211> LENGTH: 21
<212> TYPE: RNA
<213> ORGANISM: Artificial
<220> FEATURE:
<223> OTHER INFORMATION: siRNA antisense sequence

<400> SEQUENCE: 17
aguaugguca gcugcgaagu c                                              21

<210> SEQ ID NO 18
<211> LENGTH: 19
<212> TYPE: RNA
<213> ORGANISM: Artificial
<220> FEATURE:
<223> OTHER INFORMATION: siRNA sense sequence

<400> SEQUENCE: 18
gaggcgaaca cacaacguc                                                 19

<210> SEQ ID NO 19
<211> LENGTH: 19
<212> TYPE: RNA
<213> ORGANISM: Artificial
<220> FEATURE:
<223> OTHER INFORMATION: siRNA antisense sequence

<400> SEQUENCE: 19
gacguugugu guucgccuc                                                 19

<210> SEQ ID NO 20
<211> LENGTH: 92
<212> TYPE: DNA
<213> ORGANISM: Homo sapiens

<400> SEQUENCE: 20
catccggcgc tcagctgggc ttgagctgac catactccct ggagccttct cccgaggtgg    60
gcgggtgacc ttggcacata cagccatcat ga                                  92

<210> SEQ ID NO 21
<211> LENGTH: 16
<212> TYPE: DNA
<213> ORGANISM: Artificial
<220> FEATURE:
<223> OTHER INFORMATION: PCR primer

<400> SEQUENCE: 21
catccggcgc tcagct                                                    16

<210> SEQ ID NO 22
<211> LENGTH: 21
<212> TYPE: DNA
<213> ORGANISM: Artificial
<220> FEATURE:
<223> OTHER INFORMATION: PCR primer

<400> SEQUENCE: 22
tcatgatggc tgtatgtgcc a                                              21

<210> SEQ ID NO 23
<211> LENGTH: 27
<212> TYPE: DNA
```

```
<213> ORGANISM: Artificial
<220> FEATURE:
<223> OTHER INFORMATION: Probe sequence

<400> SEQUENCE: 23
ctgaccatac tccctggagc cttctcc                                          27
```

PREDICTIVE AND THERAPEUTIC MARKERS IN OVARIAN CANCER

CROSS-REFERENCE TO RELATED APPLICATIONS

This application claims benefit of priority to U.S. Provisional Patent Application No. 60/647,183, filed on Jan. 25, 2005, and International Patent Application PCT/US2006/02202, filed Jan. 19, 2006, which are hereby incorporated by reference in their entirety.

STATEMENT OF GOVERNMENTAL SUPPORT

This invention was made during work supported by the National Cancer Institute, through Grants CA 58207 and CA 64602 and during work supported by the U.S. Department of Energy under Contract No. DE-AC02-05CH11231. The government has certain rights in this invention.

REFERENCE TO SEQUENCE LISTING AND TABLE APPENDIX

The present application incorporates the attached sequence listing in its entirety. The sequence listing in paper and computer readable form are identical. The present application also incorporates attached Tables 2-6 in their entirety.

BACKGROUND OF THE INVENTION

1. Field of the Invention

The present invention also relates to markers and chromosomal amplification indicating in vivo drug resistance. More specifically, the present invention relates to using cancer markers and chromosomal region analyses for the prediction of patient outcome in ovarian cancer patients.

The present invention also relates to markers and therapeutics targeting in vivo drug resistance. More specifically, the present invention relates to the diagnosis and treatment using cancer markers and therapeutics which target drug resistance in ovarian cancer patients with low survival rates.

2. Related Art

The rapid and nearly inevitable onset of resistance in ovarian cancer has stimulated the evaluation of numerous alternative therapeutic agents. Those showing activity in ovarian cancer whose disease has relapsed after therapy with platinum and a taxane include doxil, topotecan, gemcitabine vinorelbine, etoposide and oxali platin (Harries, M. & Gore, M. Part II: chemotherapy for epithelial ovarian cancer-treatment of recurrent disease. *Lancet Oncol* 3, 537-45 (2002); Eltabbakh, G. H. & Awtrey, C. S. Current treatment for ovarian cancer. *Expert Opin Pharmacother* 2, 109-24 (2001)). In addition, advances in understanding the biology of ovarian cancer have led to the identification of cell cycle regulators, growth factor receptors, signal transduction pathways and angiogenic mechanisms that differ in normal and malignant cells. A number of targeted agents have entered clinical trials including small molecular weight inhibitors, monoclonal antibodies, and antisense and gene therapy (See, H. T., Kavanagh, J. J., Hu, W. & Bast, R. C. Targeted therapy for epithelial ovarian cancer: current status and future prospects. *Int J Gynecol Cancer* 13 (2003); Seiden, M. V. Ovarian cancer. *Oncologist* 6, 327-32 (2001)). However, most of these compounds do not specifically attack mechanisms leading to resistance.

Ovarian cancer remains the most lethal gynecologic cancer in the United States. Approximately twelve of every thousand women in this country will develop ovarian cancer in their lifetime and of these, nine or ten will succumb to the disease (American Cancer Society: Cancer Facts and Figures (URL: <http://www.cancer.org>). 2002). Most ovarian cancers are detected at an advanced stage, which contributes to the lethality. Current clinical management strategies for advanced ovarian cancers typically involve surgical reduction followed by platinum plus taxane based therapies (See Johnston, S. R. Ovarian cancer: review of the National Institute for Clinical Excellence (NICE) guidance recommendations. *Cancer Invest* 22, 730-42 (2004); Sandercock, J., Parmar, M. K., Torri, V. & Qian, W. First-line treatment for advanced ovarian cancer: paclitaxel, platinum and the evidence. *Br J Cancer* 87, 815-24 (2002); Harries, M. & Gore, M. Part II: chemotherapy for epithelial ovarian cancer-treatment of recurrent disease. *Lancet Oncol* 3, 537-45 (2002); and Harries, M. & Gore, M. Part J: chemotherapy for epithelial ovarian cancer-treatment at first diagnosis. *Lancet Oncol* 3, 529-36 (2002)). Most platinum compounds produce DNA cross-links (Bose, R. N. Biomolecular targets for platinum antitumor drugs. *Mini Rev Med Chem* 2, 103-11 (2002)) thereby inducing an apoptotic response via death receptor mechanisms as well as mitochondrial pathways (Boulikas, T. & Vougiouka, M. Cisplatin and platinum drugs at the molecular level. (Review). *Oncol Rep* 10, 1663-82 (2003); Giaccone, G. Clinical perspectives on platinum resistance. *Drugs* 59 Suppl 4, 9-17; discussion 37-8 (2000)). Taxanes, on the other hand, inhibit cell proliferation and trigger apoptotic responses by stabilizing otherwise dynamic microtubules that are important for centrosome and mitotic spindle function (Abal, M., Andreu, J. M. & Barasoain, I. Taxanes: microtubule and centrosome targets, and cell cycle dependent mechanisms of action. *Curr Cancer Drug Targets* 3, 193-203 (2003)). Unfortunately, response rates are variable and most patients eventually develop resistance to these therapies (Harries, M & Gore, M., *Lancet Oncol* 3, 529-45 (2002); Boulikas, T. & Vougiouka, M., *Oncol Rep* 10, 1663-82 (2003); and van der Burg, M. E. Advanced ovarian cancer. *Curr Treat Options Oncol* 2, 109-118 (2001)). It is an objective thereforeto identify the subset of patients with the lowest survival rate (i.e. survive less than 24 months) on these therapies and to develop therapeutic strategies specifically targeted against the molecular lesions in their tumors.

A more promising approach in the long term is likely to attack the pathways leading to resistance. Numerous studies have suggested that both proliferative and anti-apoptotic pathways may be important in the onset and maintenance of chemoresistance (see review by Frazier et al., Chemoresistance in human ovarian cancer: the role of apoptotic regulators. *Reprod Biol Endocrinol* 1, 66 (2003)). Pathways implicated in apoptosis include the death receptor family, the PI3K/AKT cell survival pathway, FAK/β-integrin signaling, prohibitin, XIAP, and p53 mediated damage response. Novel agents designed to counter these resistance mechanisms are being explored (Vasey, P. A. Resistance to chemotherapy in advanced ovarian cancer: mechanisms and current strategies. *Br J Cancer* 89 Suppl 3, S23-8 (2003)). Our understanding of the p53 damage surveillance machinery is most well developed and agents targeting tumors lacking p53 function are well along in clinical evaluations and show substantial activity (Wolf, J. K. et al. A phase I study of Adp53 (INGN 201; ADVEXIN) for patients with platinum- and paclitaxel-resistant epithelial ovarian cancer. *Gynecol Oncol* 94, 442-8 (2004); Seemann, S., Maurici, D., Olivier, M., de Fromentel, C. C. & Hainaut, P. The tumor suppressor gene TP53: implications for cancer management and therapy. *Crit. Rev Clin Lab Sci* 41, 551-83 (2004)). However, insufficient evidence now exists to identify the apoptosis-suppressing genes that might be most effectively targeted in specific platinum/taxane treated patients.

One way to identify high priority apoptosis-suppressing genes is to identify recurrent aberrations involving genome sequence, copy number and/or gene expression that are associated with reduced survival duration. Markers for these genes can then be developed to detect aggressive cancers and inhibitors of these genes can be developed to treat these cancers. Genomic, epigenomic and gene expression changes in ovarian cancers that are associated with reduced survival duration reported recently include: (a) elevated/altered expression of COX-2 expression, p53 and SMAD4 (Erkinheimo, T. L. et al. Elevated cyclooxygenase-2 expression is associated with altered expression of p53 and SMAD4, amplification of HER-2/neu, and poor outcome in serous ovarian carcinoma. *Clin Cancer Res* 10, 538-45 (2004)), (b) reduced interferon gamma expression (Marth, C. et al. Interferon-gamma expression is an independent prognostic factor in ovarian cancer. *Am J Obstet Gynecol* 191, 1598-605 (2004)), (c) increased expression of focal adhesion kinase (FAK)(Sood, A. K. et al. Biological significance of focal adhesion kinase in ovarian cancer: role in migration and invasion. *Am J Pathol* 165, 1087-95 (2004)) (d) high bikunin expression (Tanaka, Y. et al. Reduced bikunin gene expression as a factor of poor prognosis in ovarian carcinoma. *Cancer* 98, 424-30 (2003)), (e) p16 methylation (Katsaros, D. et al. Methylation of tumor suppressor gene p16 and prognosis of epithelial ovarian cancer. *Gynecol Oncol* 94, 685-92 (2004)) and over expression of RAB25 (Cheng, K. W. et al. The RAB25 small GTPase determines aggressiveness of ovarian and breast cancers. *Nat Med* 10, 1251-6 (2004)). These studies have been guided by biological insights into the molecular events that are associated with ovarian cancer progression and provide information that may be used to develop useful prognostic markers. They are limited, however, since they do not provide information about the relative importance of these markers.

Relative importance has been assessed by others to identify aberrations that are most strongly associated with poor outcome in ovarian cancer using tumor transcription profiling and array technology. Published studies so far include a study that identified 182 hypermethylated CpG sequences associated with poor outcome (Wei, S. H., Brown, R. & Huang, T. H. Aberrant DNA methylation in ovarian cancer: is there an epigenetic predisposition to drug response? *Ann N Y Acad Sci* 983, 243-50 (2003)) and a gene expression profiling study that reported an 115-gene signature Ovarian Cancer Prognostic Profile (OCPP) associated with short survival duration (Spentzos, D. et al. Gene expression signature with independent prognostic significance in epithelial ovarian cancer. *J Clin Oncol* 22, 4648-58 (2004)).

One of the inventors with others have also described in U.S. Pat. No. 6,268,184 that the identification of chromosomal abnormalities and amplification in the human 20q13 chromosomal region can be used as a prognostic indicator of breast cancer.

RELATED PUBLICATIONS

Volik, S., Zhao, S., Chin, K., Brebner, J. H., Hemdon, D. R., Tao, Q., Kowbel, K., Huang, G., Lapuk, A., Kuo, W-L., Magrane, G., de Jong, P., Gray, J. W., and Collins, C. (2003). End Sequence Profiling: sequence-based analysis of aberrant genomes. PNAS 100:7696-701.
Anand N, Murthy S, Amann G, Wernick M, Porter L A, Cukier I H, Collins C, Gray J W, Diebold J, Demetrick D J, Lee J M. (2002) Protein elongation factor EEF 1A2 is a putative oncogene in ovarian cancer. Nat. Genet. 31:301-305.
Gray, J. W., Suzuki, S., Kuo, W.-L., Polikoff, D., Deavers, M., Smith-McCune, K., Berchuck, A., Pinkel, D., Albertson, D. and Mills, G. (2003). Specific Keynote: Genome Copy Number Abnormalities in Ovarian Cancer. Gynecologic Oncology, Vol. 88, Issue 1, S16-S21.
Cheng, K. W., Lahad, J. P., Kuo, W.-L., Lapuk, A., Yamada, K., Auersperg, N., Liu, J., Smith-McCune, K., Lu, K. H., Fishman, D., Gray, J. W., Mills, G. B. (2004) The RAB25 small GTPase determines aggressiveness of ovarian and breast cancers. Nat. Med. 10:1251-11256
Lapuk, A., Volik, S., Vincent, R., Kuo, W-L., de Jong, P., Collins, C., Gray, J. W. (2004). Computational BAC clone contig assembly for comprehensive genome analysis. Genes Chromosomes & Cancer 40:66-71.
Albertson, D. G., Collins, C., McCormick, F., Gray, J. W. (2003). Chromosome aberrations in solid tumors. Nature Genetics 34: 369-376.

BRIEF SUMMARY OF THE INVENTION

The present invention provides for the identification of high priority apoptosis-suppressing genes by identification of recurrent aberrations involving genome sequence, copy number and/or gene expression that are associated with reduced survival duration. Markers for these genes can then be developed to detect diseases characterized by increased expression of apoptosis-suppressing genes, such as aggressive cancers. Inhibitors of these genes can be developed to treat these diseases.

In one aspect, genome scale analysis technologies are used to identify aberrations that are most strongly associated with poor outcome in ovarian cancer. In one embodiment, array comparative genomic hybridization (CGH) was used to detect high level amplifications of regions of chromosomes 8q24, 11q13 and 20q11-13 as strongly associated with reduced survival duration in patients treated with surgery plus platinum/taxane based agents. Amplification at 8q24 is the strongest predictor of the three in ovarian cancer and has been shown by the results described herein to be a very strong predictor of poor outcome in breast cancer as well. The region of amplification associated with poor outcome is very close to the location of MYC and published FISH studies support the association of amplification of this region with reduced survival duration (Baker, V. V. et al. c-myc amplification in ovarian cancer. *Gynecol Oncol* 38, 340-2 (1990); Wang, Z. R., Liu, W., Smith, S. T., Parrish, R. S. & Young, S. R. c-myc and chromosome 8 centromere studies of ovarian cancer by interphase FISH. *Exp Mol Pathol* 66, 140-8 (1999)).

These data suggest that amplification at these loci will identify a poorly performing subset of patients that can be offered alternative therapies. Moreover, si/shRNA and/or small molecule inhibitors can be made for genes in regions of amplification at 8q24, 11q13 and/or 20q11-13 that cause reduced apoptotic surveillance when over expressed. Inhibitors of anti-apoptotic genes found in the three regions will likely be effective against tumors in which the target genes are amplified.

Our studies of ovarian cancer have combined genome scale analyses of gene expression and genome copy number in 250 serous ovarian cancer patients to identify specific aberrations and genes that are most strongly associated with reduced survival duration. Importantly, high level amplification in general and amplifications specifically at 8q24.1, 11q13.3, 20q13.1 and 20q13.2 are significantly associated with reduced survival duration in conventionally treated patients.

In one aspect of the invention, assessment of amplification at 8q24.1, 11q13.3, 20q13.1 and 20q13.2 should be readily detected by such methods as array comparative genomic hybridization (CGH), fluorescent in situ hybridization, and quantitative PCR.

In one embodiment, array comparative genomic hybridization (CGH) is used to detect high level amplifications of regions of chromosomes 8q24, 11q13 and 20q11-13 which are strongly associated with reduced survival duration in patients treated with surgery plus platinum/taxane based agents.

In another embodiment, the invention provides for an assay using fluorescence in situ hybridization (FISH) with probes to these three loci to identify a poorly performing subset of patients that can be offered alternative therapies. In another aspect, the invention provides a tri-locus test using FISH probes to detect chromosomal amplification. In one embodiment, the tri-locus test detects chromosomal amplification at 8q24, 11q13 and 20q11-13. In a preferred embodiment, the tri-locus test detects chromosomal amplification at 8q24.1, 11q13.3 and 20q13.1. In another embodiment, the tri-locus test detects chromosomal amplification at 8q24.1, 11q13.3 and 20q13.2. In a preferred embodiment, probe(s) selected for each region are to a gene in the region as follows: for 8q, MYC and PVT1; for 11q, CCND1; for 20q13.1, HE4 and WHDC2; for 20q13.2, ZNF21; and for 20q13.3, PTK6.

In one embodiment, assessment of amplification at 8q24, 11q13 and 20q11-13 should be readily detected using multicolor FISH. This is important from a translational point of view since FISH can be readily applied to paraffin embedded samples and paths to FDA approval of FISH based assays are well established. To this end, it is an object of the invention to develop, validate and deploy a fully validated FISH assay for poor clinical response in platinum/taxane treated ovarian cancers as a commercial product.

In another embodiment, elevated gene expression at 8q24, 11q13 and 20q11-13 is detected using quantitative PCR. The transcription levels of single or multiple genes in the tri-locus region can be measured in comparison to normal levels. Moreover, high level amplification and/or over expression of certain genes, such as PVT1, are significantly associated with reduced survival duration in ovarian tumors.

In another aspect, the present invention describes several genes in regions of amplification at 8q24, 11q13 and/or 20q11-13 that are over expressed when amplified. siRNA inhibitors of several of these genes decreased proliferation and/or increase apoptosis. This suggests that amplification at these loci causes over expression of genes that coordinately increase proliferation and inhibit apoptotic responses to oncogene activation and to platinum/taxane therapies. In so doing, these amplification events significantly reduce survival duration. Thus, it is a goal of the invention to pursue amplicon targeted therapies as independent therapeutic modalities. In a preferred embodiment, the high priority targets for therapeutics include MYC and PVT1 at 8q24; CCND1, PPFIA1 and EMS1 at 11q13 and PTK6, EEF1A2 and ZNF217 at 20q11-q13.

In one embodiment, initial priority has been given to the gene, PVT1, since it maps to the region of amplification at 8q24 that is most strongly associated with reduced survival duration in platinum/taxane treated patients. The transcription levels of PVT1 was highly correlated with the DNA copy number alterations in ovarian cell lines (Pearson's correlation coefficient=0.74). Moreover, high level amplification and/or over expression of PVT1 are significantly associated with reduced survival duration in ovarian tumors.

Therefore, it is an object of the invention to provide for an assay to detect elevated PVT1 expression as a predictor of poor response to taxol plus platinum based therapies in serous ovarian cancers. In some embodiments, the assay to detect PVT1 over-amplification is selected from the group: FISH to detect 8q24 amplification; FISH to detect PVT1 amplification, a PCR assay to detect PVT1 amplification; an immunochemical assay to detect PVT1 protein levels; an RT-PCR assay to detect PVT1 transcription levels. Such molecular procedures that detect PVT1 amplification or over expression in serous ovarian cancers will identify patients that will not respond well to conventional platinum plus taxol based therapies. They also show that these patients will respond to therapies that inhibit PVT1 expression.

In another aspect, the present invention provides for a compound to treat patients with elevated PVT1 expression, wherein the compound is a PVT1 inhibitor selected from the group consisting of an antisense oligonucleotide; a siRNA olignonucleotide; a small molecule that interferes with PVT1 function; a viral vector producing a nucleic acid sequence that inhibits PVT1; and an aptamer.

In another aspect, si/shRNA and/or small molecule inhibitors can be made against PVT1 for the treatment of cancer and to induce cell death. siRNAs against PVT1 were particularly effective in inhibiting proliferation and in inducing apoptosis in cells in which PVT1 was amplified and over expressed. Therefore, it is an object of the invention to provide therapeutics for treatment of cells that over express PVT1 to reduce PVT1 transcription and thereby inhibit cell proliferation by blocking cell in the G1-phase of the cell cycle and by inducing cell death.

BRIEF DESCRIPTION OF THE DRAWINGS

FIG. 4 shows a FISH contig assembly for EVI1 and MYC and two images of 2-color FISH results showing normal (2 copies each, left image) and aberrant (increased copy numbers, right image).

FIG. 9A(2) is a graph showing the DNA distribution of CAOV4 cells treated with an siRNA against MYC. FIG. 9A(3) is a graph showing the DNA distribution of CAOV4 cells treated with an siRNA against PVT1.

FIGS. 10A and 10B are graphs showing the fluorescence intensity of nucleus intensity, f-actin content and mitochondria mass/potential in OV90 and OVCA432 cancer cells after treatment with a control, lipofectamine, PVT1 siRNA and taxol. FIG. 10C shows the number of apoptotic cells using the F-actin content in ovarian cancer cell lines treated with PVT1 siRNA.

FIG. 11B shows the 8q24 amplicon as derived from 106 serous tumors. FIG. 11C shows the 8q24 amplicon as derived from 20 ovarian cancer cell lines.

DETAILED DESCRIPTION OF THE PREFERRED EMBODIMENT

Figure 1:
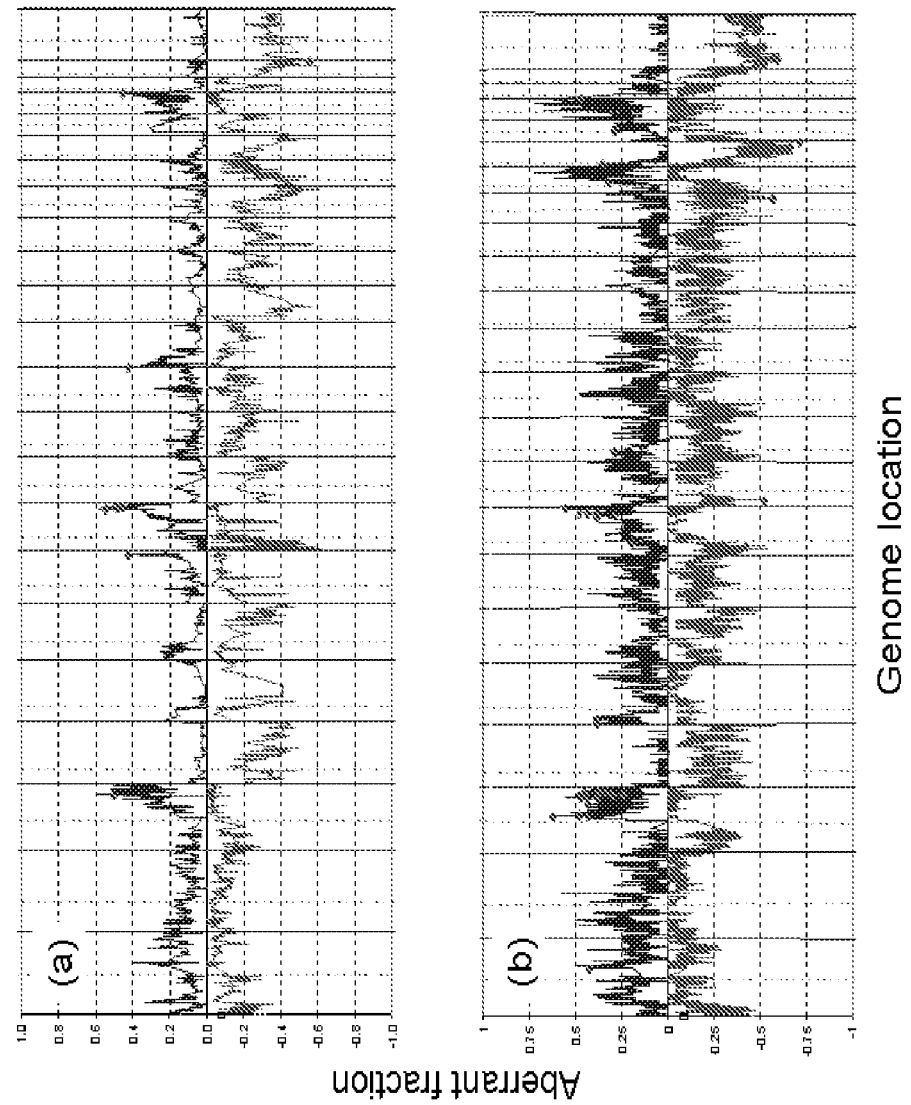
FIG. 1 is a graph showing recurrent aberrations in ovarian cancer detected using array CGH. Frequencies of chromosome aberrations (gains positive values, losses negative values) are displayed as a function of distance along the genome. Vertical lines show chromosome boundaries. Dashed vertical lines show centromere locations. Red symbols show locations of high level amplification or homozygous deletion. Panel a show analyses of 250 primary ovarian cancers. Panel b shows analyses of 21 ovarian cancer cell lines.

Our studies of ovarian cancer have combined genome scale analyses of gene expression and genome copy number in 250 serous ovarian cancer patients to identify specific aberrations and genes that are most strongly associated with reduced survival duration (see Progress for detailed information). These analyses have defined the location and frequency of occurrence of ~20 regions of genome copy number abnormality that are present in at least 30% of tumors. About half of these are copy number increases. Importantly, high level amplification in general and amplifications specifically at 8q24, 11q13, and 20q11-q13 are significantly associated with reduced survival duration in conventionally treated patients (surgical debulking with platinum and taxol adjuvant therapy; data not shown). Amplification at 8q24 is the strongest predictor of the three in ovarian cancer and has been shown by the results described herein to be a very strong predictor of poor outcome in breast cancer as well. The region of amplification associated with poor outcome is very close to the location of MYC and published FISH studies support the association of amplification of this region with reduced survival duration (Baker, V. V. et al. c-myc amplification in ovarian cancer. *Gynecol Oncol* 38, 340-2 (1990); Wang, Z. R., et al., c-myc and chromosome 8 centromere studies of ovarian cancer by interphase FISH. *Exp Mol Pathol* 66, 140-8 (1999)). Table 1 shows the genes located in the three chromosomal regions implicated in disease such as ovarian cancer from analyses of copy number, expression and outcome. The GenBank Accession numbers or coordinates for the genes shown in Table 1 are hereby incorporated by reference.

TABLE 1

Genes implicated from analyses of copy number, expression and outcome

| AccNo | LocusID | Chrom | AFFY | Description | Association of expression with outcome | | Association of expression with copy number at FISH locus | |
|---|---|---|---|---|---|---|---|---|
| | | | | | rawp | adjp | Pearson | Spearman |
| NM_002514 | 4856 | 8 | NOV | nephroblastoma overexpressed gene | 0.017 | 0.096 | 0.349 | 0.302 |
| M34428 | 5820 | 8 | PVT1 | Pvt1 oncogene homolog, MYC activator (mouse) | 0 | 0.018 | 0.329 | 0.334 |
| AV720514 | 51571 | 8 | FAM49B | family with sequence similarity 49, member B | 0.01 | 0.074 | 0.127 | 0.05 |
| NM_003235 | 7038 | 8 | TG | thyroglobulin | 0.018 | 0.098 | 0.221 | 0.233 |
| AK026820 | NA | 8 | NA | NA | 0.006 | 0.058 | 0.348 | 0.334 |
| AU158606 | 91683 | 11 | SYT12 | synaptotagmin XII | 0.003 | 0.043 | 0.201 | 0.227 |
| NM_002708 | 5499 | 11 | PPP1CA | Protein phosphatase 1, catalytic subunit, alpha isoform | 0.001 | 0.033 | 0.285 | 0.269 |
| NM_004910 | 9600 | 11 | PITPNM1 | phosphatidylinositol transfer protein, membrane-associated 1 | 0.017 | 0.096 | 0.281 | 0.247 |
| NM_016366 | 51475 | 11 | CABP2 | calcium binding protein 2 | 0 | 0.018 | 0.277 | 0.278 |
| AI674138 | 347853 | 11 | TBX10 | T-box 10 | 0.004 | 0.052 | 0.175 | 0.169 |
| NM_030930 | 81622 | 11 | UNC93B1 | unc-93 homolog B1 (*C. elegans*) | 0.005 | 0.055 | 0.301 | 0.379 |

TABLE 1-continued

Genes implicated from analyses of copy number, expression and outcome

| AccNo | LocusID | Chrom | AFFY | Description | Association of expression with outcome | | Association of expression with copy number at FISH locus | |
|---|---|---|---|---|---|---|---|---|
| | | | | | rawp | adjp | Pearson | Spearman |
| AF052128 | 3508 | 11 | IGHMBP2 | immunoglobulin mu binding protein 2 | 0 | 0.022 | 0.423 | 0.411 |
| Z23022 | 595 | 11 | CCND1 | cyclin D1 (PRAD1) | 0.001 | 0.029 | 0.119 | 0.099 |
| NM_005553 | 3846 | 11 | KRN1 | keratin, cuticle, ultrahigh sulphur 1 | 0.004 | 0.051 | 0.376 | 0.357 |
| NM_005699 | 10068 | 11 | IL18BP | interleukin 18 binding protein | 0.011 | 0.078 | 0.157 | 0.099 |
| NM_000804 | 2352 | 11 | FOLR3 | folate receptor 3 (gamma) | 0.007 | 0.061 | 0.062 | 0.092 |
| NM_014786 | 9828 | 11 | ARHGEF17 | Rho guanine nucleotide exchange factor (GEF) 17 | 0.003 | 0.047 | 0.238 | 0.374 |
| BF513857 | 5870 | 11 | RAB6A | RAB6A, member RAS oncogene family | 0.006 | 0.059 | 0.158 | 0.207 |
| NM_022803 | 7352 | 11 | UCP3 | uncoupling protein 3 (mitochondrial, proton carrier) | 0.007 | 0.064 | 0.271 | 0.359 |
| NM_025086 | 80156 | 11 | FLJ22596 | hypothetical protein FLJ22596 | 0.001 | 0.027 | 0.163 | 0.149 |
| AK022450 | 10825 | 11 | NEU3 | sialidase 3 (membrane sialidase) | 0.001 | 0.026 | 0.256 | 0.165 |
| N80935 | NA | 11 | NA | NA | 0.005 | 0.053 | 0.239 | 0.391 |
| BF448703 | 283212 | 11 | FLJ33790 | hypothetical protein FLJ33790 | 0.002 | 0.042 | 0.438 | 0.341 |
| NM_025098 | 80168 | 11 | MOGAT2 | monoacylglycerol O-acyltransferase 2 | 0 | 0.017 | 0.395 | 0.329 |
| NM_006189 | 4975 | 11 | OMP | olfactory marker protein | 0.014 | 0.087 | 0.19 | 0.099 |
| NM_000260 | 4647 | 11 | MYO7A | myosin VIIA (Usher syndrome 1B (autosomal recessive, severe)) | 0.003 | 0.046 | 0.481 | 0.435 |
| AF152863 | 28954 | 20 | REM1 | RAS (RAD and GEM)-like GTP-binding 1 | 0.007 | 0.064 | 0.297 | 0.3 |
| AL080086 | 140688 | 20 | C20orf112 | chromosome 20 open reading frame 112 | 0.013 | 0.084 | 0.265 | 0.323 |
| AI810484 | 9139 | 20 | CBFA2T2 | zinc finger protein 75 (D8C6) | 0.004 | 0.051 | 0.573 | 0.662 |
| AK000947 | 57644 | 20 | MYH7B | myosin, heavy polypeptide 7B, cardiac muscle, beta | 0.001 | 0.028 | 0.279 | 0.266 |
| NM_024777 | 79835 | 20 | FERIL4 | Fer-1-like 4 | 0.017 | 0.094 | 0.115 | 0.082 |
| AY027523 | 51230 | 20 | C20orf104 | chromosome 20 open reading frame 104 | 0.001 | 0.03 | 0.272 | 0.395 |
| AA573523 | 2036 | 20 | EPB41L1 | erythrocyte membrane protein band 4.1-like 1 | 0.001 | 0.03 | 0.453 | 0.317 |
| NM_005417 | 6714 | 20 | SRC | v-src sarcoma (Schmidt-Ruppin A-2) viral oncogene homolog (avian) | 0.005 | 0.054 | 0.171 | 0.298 |
| BC003551 | 7052 | 20 | TGM2 | transglutaminase 2 (C polypeptide, protein-glutamine-gamma-glutamyltransferase) | 0.01 | 0.074 | 0.206 | 0.275 |
| AL110247 | 5335 | 20 | PLCG1 | phospholipase C, gamma 1 | 0.006 | 0.061 | 0.638 | 0.602 |
| NM_024034 | 78997 | 20 | GDAP1L1 | ganglioside-induced differentiation-associated protein 1-like 1 | 0.007 | 0.061 | 0.03 | 0.095 |
| X87870 | 3172 | 20 | HNF4A | hepatocyte nuclear factor 4, alpha | 0.002 | 0.036 | 0.471 | 0.438 |
| NM_006282 | 6789 | 20 | STK4 | serine/threonine kinase 4 | 0.003 | 0.043 | 0.262 | 0.411 |
| NM_003833 | 8785 | 20 | MATN4 | matrilin 4 | 0.005 | 0.054 | 0.156 | 0.251 |
| NM_014276 | 11317 | 20 | RBPSUHL | recombining binding protein suppressor of hairless (*Drosophila*)-like | 0.001 | 0.031 | 0.507 | 0.391 |
| AW118166 | 10816 | 20 | SPINT3 | serine protease inhibitor, Kunitz type, 3 | 0.003 | 0.044 | 0.176 | 0.172 |
| NM_003279 | 7125 | 20 | TNNC2 | troponin C2, fast | 0.001 | 0.029 | 0.21 | 0.163 |
| AI743331 | 63935 | 20 | C20orf67 | chromosome 20 open reading frame 67 | 0.003 | 0.046 | 0.523 | 0.509 |
| AA845577 | 63925 | 20 | ZNF335 | zinc finger protein 335 | 0.018 | 0.099 | 0.237 | 0.191 |
| AL121777 | 170552 | 20 | SRMP1 | spermidine synthase pseudogene 1 | 0 | 0.018 | 0.275 | 0.227 |
| BF222916 | 5770 | 20 | PTPN1 | protein tyrosine phosphatase, non-receptor type 1 | 0.001 | 0.029 | 0.46 | 0.437 |
| NM_017843 | 55653 | 20 | BCAS4 | breast carcinoma amplified sequence 4 | 0.003 | 0.044 | 0.116 | 0.195 |

TABLE 1-continued

Genes implicated from analyses of copy number, expression and outcome

| | | | | | Association of expression with outcome | | Association of expression with copy number at FISH locus | |
|---|---|---|---|---|---|---|---|---|
| AccNo | LocusID | Chrom | AFFY | Description | rawp | adjp | Pearson | Spearman |
| BC006367 | 3755 | 20 | KCNG1 | potassium voltage-gated channel, subfamily G, member 1 | 0.004 | 0.052 | 0.36 | 0.423 |
| NM_002623 | 5203 | 20 | PFDN4 | prefoldin 4 | 0.006 | 0.058 | 0.193 | 0.239 |
| BC004248 | 655 | 20 | BMP7 | bone morphogenetic protein 7 (osteogenic protein 1) | 0 | 0.018 | 0.173 | 0.078 |
| NM_024314 | 79160 | 20 | MGC4294 | hypothetical protein MGC4294 | 0.004 | 0.052 | 0.437 | 0.453 |
| AA398062 | 79716 | 20 | NPEPL1 | aminopeptidase-like 1 | 0.005 | 0.053 | 0.191 | 0.295 |
| AA418800 | 1522 | 20 | CTSZ | cathepsin Z | 0.001 | 0.028 | −0.029 | 0.072 |
| NM_001794 | 1002 | 20 | CDH4 | cadherin 4, type 1, R-cadherin (retinal) | 0.006 | 0.058 | 0.089 | 0.11 |
| NM_014054 | 28980 | 20 | C20orf40 | Chromosome 20 open reading frame 40 | 0.003 | 0.047 | 0.282 | 0.309 |
| AB045369 | 11255 | 20 | HRH3 | histamine receptor H3 | 0.013 | 0.084 | 0.157 | 0.207 |

Thus, markers for the genes shown to be amplified in these regions may be developed to detect diseases characterized by increased expression of apoptosis-suppressing genes, such as aggressive cancers. In a preferred embodiment, diagnosis and assessment of amplification levels of any one of these genes shown to be amplified in Table 1 can be useful in prediction of poor outcome of patient's response and drug resistance in ovarian cancer patients with low survival rates.

Moreover, certain genes were found to be high priority therapeutic targets as apoptosis-suppressing genes. The identification of recurrent aberrations involving genome sequence, copy number and/or gene expression are associated with reduced survival duration in certain diseases and cancers, specifically ovarian cancer. Therefore, therapeutics to inhibit amplification and inhibitors of these genes can be developed to treat these diseases.

Assessment of amplification at 8q24, 11q13, 20q11-q13 can be readily detected by methods known in the art. In a preferred embodiment, the amplification can be detected using multi-color Fluorescent In Situ Hybridization (FISH) methods. This is important from a translational point of view since FISH can be readily applied to paraffin embedded samples and paths to FDA approval of FISH based assays are well established (Sokolova, I. A. et al. The development of a multitarget, multicolor fluorescence in situ hybridization assay for the detection of urothelial carcinoma in urine. *J Mol Diagn* 2, 116-23. (2000)). To this end, in a preferred embodiment, the invention provides for a fully validated FISH assay for poor clinical response in platinum/taxane treated ovarian cancers.

In one embodiment, elevated gene expression is detected using FISH to detect 8q24 amplification. For example, one can create probes that hybridize to the 8q24 region, found in GenBank Accession No: NT_008046. Probes can be created by methods known in the art based upon the sequences of genes in 8q24 such as those identified in Table 1. For example, 500 Kbp contiguous spanning regions of high level amplification at 8q24.13 that are most strongly associated with survival duration, avoiding regions of the genome that harbor low level repeats that may not be fully blocked during hybridization content thereby giving false positive hybridization signals. DNA from the probe generated can be produced and labeled with known fluorescent dyes, such as Spectrum Orange, Spectrum Green and Spectrum Aqua (Vysis, Inc.) to produce hybridization probes for detection of amplification at the test loci. In a preferred embodiment, probe production and labeling will be accomplished using Good Manufacturing Practices (GMP) at Vysis so that the analyses will be useful in obtaining FDA approval for clinical use of these markers. In another embodiment, the in situ hybridization methods of identifying probes described in U.S. Pat. No. 6,268,184, which is hereby incorporated by reference, is used. Methods of preparing probes are well known to those of skill in the art (see, e.g. Sambrook et al., Molecular Cloning: A Laboratory Manual (2nd ed.), Vols. 1-3, Cold Spring Harbor Laboratory, (1989) or Current Protocols in Molecular Biology, F. Ausubel et al., ed. Greene Publishing and Wiley-Interscience, New York (1987)).

In another embodiment, elevated expression is detected using FISH to detect chromosomal amplification. Probes can be created by methods described above based upon the genomic sequence containing and flanking genes in contigs covering *Homo sapiens* chromosome 8q24.1, found at GenBank Accession Nos. NT_008046, NT_086743; contigs covering *Homo sapiens* chromosome 11q13.3, found at GenBank Accession Nos. NT_078088, NT_033927, NT_033903; contig covering *Homo sapiens* chromosome 20q13.1 and 20q13.2, found at GenBank Accession Nos. NT_011362, all of which is hereby incorporated by reference.

In another embodiment, a tri-locus fluorescence in situ hybridization (FISH) assay can be used to detect high level amplification at any three of the regions 8q24, 11q13, and 20q11-q13 for paraffin embedded samples that will identify patients that will survive less than 24 months with specificity>95% and sensitivity>60%. For the tri-locus FISH assay, three probes chosen from three different amplicons are chosen. In a preferred embodiment, the tri-locus test detects chromosomal amplification specifically at 8q24.1, 11q13.3 and 20q13.1 because these three loci were shown to have both strong overexpression of genes in the region and corresponding strong array CGH data showing amplification. In other embodiments, it is preferred that the third probe can detect chromosomal amplification at 20q13.2.

An example of a method that can be used to develop probes for the trilocus FISH assay is found in U.S. Pat. No. 6,268,184, hereby incorporated by reference. The method as applied to development of probes for predicting the outcome of ovarian cancer can be as follows. The probes listed in Tables 2-6 are suitable for use in detecting the 8q24, 11q13, or 20q11-q13 amplicons. Table 2 corresponds to the probes found for 8q, Table 3 corresponds to the probes found for 11q, Table 4 corresponds to the probes found for 20q13.1, Table 5 corresponds to the probes found for 20q13.2, and Table 6 corresponds to the probes found for 20q13.3. All GenBank sequences listed in the Tables are hereby incorporated by reference. In a preferred embodiment, probe(s) selected for each region are to a gene in the region as follows: for 8q, MYC and PVT1; for 11q, CCND1; for 20q13.1, HE4 and WHDC2; and for 20q13.2, ZNF217.

Methods of preparing probes are well known to those of skill in the art (see, e.g. Sambrook et al., Molecular Cloning: A Laboratory Manual (2nd ed.), Vols. 1-3, Cold Spring Harbor Laboratory, (1989) or Current Protocols in Molecular Biology, F. Ausubel et al., ed. Greene Publishing and Wiley-Interscience, New York (1987)), which are hereby incorporated by reference.

The probes are most easily prepared by combining and labeling one or more of the constructs listed in Tables 2-6. Prior to use, the constructs are fragmented to provide smaller nucleic acid fragments that easily penetrate the cell and hybridize to the target nucleic acid. Fragmentation can be by any of a number of methods well known to hose of skill in the art. Preferred methods include treatment with a restriction enzyme to selectively cleave the molecules, or alternatively to briefly heat the nucleic acids in the presence of $Mg^{2+}$. Probes are preferably fragmented to an average fragment length ranging from about 50 bp to about 2000 bp, more preferably from about 100 bp to about 1000 bp and most preferably from about 150 bp to about 500 bp.

Alternatively, probes can be produced by amplifying (e.g. via PCR) selected subsequences from the trilocus amplicons disclosed herein. The sequences provided herein permit one of skill to select primers that amplify sequences from one or more exons located within the 8q24, 11q13, or 20q13 amplicons.

Labeling Probes.

Methods of labeling nucleic acids are well known to those of skill in the art. Preferred labels are those that are suitable for use in in situ hybridization. The nucleic acid probes may be detectably labeled prior to the hybridization reaction. Alternatively, a detectable label which binds to the hybridization product may be used. Such detectable labels include any material having a detectable physical or chemical property and have been well-developed in the field of immunoassays.

As used herein, a "label" is any composition detectable by spectroscopic, photochemical, biochemical, immunochemical, or chemical means. Useful labels in the present invention include radioactive labels (e.g., $^{32}P$, $^{125}I$, $^{14}C$, $^{3}H$, and $^{35}S$), fluorescent dyes (e.g. fluorescein, rhodamine, Texas Red, etc.), electron-dense reagents (e.g. gold), enzymes (as commonly used in an ELISA), colorimetric labels (e.g. colloidal gold), magnetic labels (e.g. DYNABEADS™), and the like. Examples of labels which are not directly detected but are detected through the use of directly detectable label include biotin and digoxigenin as well as haptens and proteins for which labeled antisera or monoclonal antibodies are available.

The particular label used is not critical to the present invention, so long as it does not interfere with the in situ hybridization of the stain. However, stains directly labeled with fluorescent labels (e.g. fluorescein-12-dUTP, Texas Red-5-dUTP, etc.) are preferred for chromosome hybridization.

A direct labeled probe, as used herein, is a probe to which a detectable label is attached. Because the direct label is already attached to the probe, no subsequent steps are required to associate the probe with the detectable label. In contrast, an indirect labeled probe is one which bears a moiety to which a detectable label is subsequently bound, typically after the probe is hybridized with the target nucleic acid.

In addition the label must be detectable in as low copy number as possible thereby maximizing the sensitivity of the assay and yet be detectible above any background signal. Finally, a label must be chosen that provides a highly localized signal thereby providing a high degree of spatial resolution when physically mapping the stain against the chromosome. Particularly preferred fluorescent labels include fluorescein-12-dUTP and Texas Red-5-dUTP.

The labels may be coupled to the probes in a variety of means known to those of skill in the art. In a preferred embodiment the nucleic acid probes will be labeled using nick translation or random primer extension (Rigby, et al. J. Mol. Biol., 113: 237 (1977) or Sambrook, et al., Molecular Cloning—A Laboratory Manual, Cold Spring Harbor Laboratory, Cold Spring Harbor, N.Y. (1985)).

One of skill in the art will appreciate that the probes of this invention need not be absolutely specific for the targeted 8q24, 11q13, or 20q11-13 regions of the genome. Rather, the probes are intended to produce "staining contrast". "Contrast" is quantified by the ratio of the probe intensity of the target region of the genome to that of the other portions of the genome. For example, a DNA library produced by cloning a particular chromosome (e.g. chromosome 7) can be used as a stain capable of staining the entire chromosome. The library contains both sequences found only on that chromosome, and sequences shared with other chromosomes. Roughly half the chromosomal DNA falls into each class. If hybridization of the whole library were capable of saturating all of the binding sites on the target chromosome, the target chromosome would be twice as bright (contrast ratio of 2) as the other chromosomes since it would contain signal from the both the specific and the shared sequences in the stain, whereas the other chromosomes would only be stained by the shared sequences. Thus, only a modest decrease in hybridization of the shared sequences in the stain would substantially enhance the contrast. Thus contaminating sequences which only hybridize to non-targeted sequences, for example, impurities in a library, can be tolerated in the stain to the extent that the sequences do not reduce the staining contrast below useful levels.

Detecting the 8q24, 11q13, or 20q11-q13 Amplicons.

It is contemplated that detection of amplification in the 8q24, 11q13, or 20q11-q13 amplicons is indicative of the presence and/or prognosis of a large number of cancers. These include, but are not limited to breast, ovary, bladder, head and neck, and colon. The Examples show that detection of amplification in 8q24, 11q13, or 20q11-q13 amplicons are at least indicative of poor outcome in ovarian cancer patients.

In a preferred embodiment, a 8q24, 11q13, or 20q11-q13 amplification is detected through the hybridization of a probe of this invention to a target nucleic acid (e.g. a chromosomal sample) in which it is desired to screen for the amplification. Suitable hybridization formats are well known to those of skill in the art and include, but are not limited to, variations of Southern Blots, in situ hybridization and quantitative amplification methods such as quantitative PCR (see, e.g. Sambrook, supra., Kallioniemi et al., Proc. Natl. Acad Sci USA, 89: 5321-5325 (1992), and PCR Protocols, A Guide to Methods and Applications, Innis et al., Academic Press, Inc. N.Y., (1990)).

In another embodiment, a 500 Kbp reference probe at 21q21.3 (26,029 Kbp) is generated. Array CGH analyses show this region to the least frequently aberrant locus in serous ovarian cancers (present at abnormal copy number in <5% of all cancers). This probe will be labeled with Spectrum Gold so it can serve as a reference for all three test loci.

In Situ Hybridization.

In a preferred embodiment, the 8q24, 11q13, or 20q11-q13 amplicons are identified using in situ hybridization. Generally, in situ hybridization comprises the following major steps: (1) fixation of tissue or biological structure to analyzed; (2) prehybridization treatment of the biological structure to increase accessibility of target DNA, and to reduce nonspecific binding; (3) hybridization of the mixture of nucleic acids to the nucleic acid in the biological structure or tissue; (4) posthybridization washes to remove nucleic acid fragments not bound in the hybridization and (5) detection of the hybridized nucleic acid fragments. The reagent used in each of these steps and their conditions for use vary depending on the particular application.

In some applications it is necessary to block the hybridization capacity of repetitive sequences. In this case, human genomic DNA is used as an agent to block such hybridization. The preferred size range is from about 200 bp to about 1000 bases, more preferably between about 400 to about 800 bp for double stranded, nick translated nucleic acids.

Hybridization protocols for the particular applications disclosed here are described in Pinkel et al. Proc. Natl. Acad. Sci. USA, 85: 9138-9142 (1988) and in EPO Pub. No. 430,402. Suitable hybridization protocols can also be found in Methods in Molecular Biology Vol. 33, In Situ Hybridization Protocols, K. H. A. Choo, ed., Humana Press, Totowa, N.J., (1994). In a particularly preferred embodiment, the hybridization protocol of Kallioniemi et al., ERBB2 amplification in breast cancer analyzed by fluorescence in situ hybridization. *Proc Natl Acad Sci USA*, 89: 5321-5325 (1992) is used.

Typically, it is desirable to use dual color FISH, in which two probes are utilized, each labelled by a different fluorescent dye. A test probe that hybridizes to the region of interest is labelled with one dye, and a control probe that hybridizes to a different region is labelled with a second dye. A nucleic acid that hybridizes to a stable portion of the chromosome of interest, such as the centromere region, is often most useful as the control probe. In this way, differences between efficiency of hybridization from sample to sample can be accounted for.

The FISH methods for detecting chromosomal abnormalities can be performed on nanogram quantities of the subject nucleic acids. Paraffin embedded tumor sections can be used, as can fresh or frozen material. Because FISH can be applied to the limited material, touch preparations prepared from uncultured primary tumors can also be used (see, e.g., Kallioniemi, A. et al., Cytogenet. Cell Genet. 60: 190-193 (1992)). For instance, small biopsy tissue samples from tumors can be used for touch preparations (see, e.g., Kallioniemi, A. et al., Cytogenet. Cell Genet. 60: 190-193 (1992)). Small numbers of cells obtained from aspiration biopsy or cells in bodily fluids (e.g., blood, urine, sputum and the like) can also be analyzed. For prenatal diagnosis, appropriate samples will include amniotic fluid and the like.

The tri-locus amplification assay developed in Example 2 will stratify patients according to outcome in three retrospective analyses: (1) 70 samples from patients treated with platinum/taxol at MDACC on GOG protocol 0152; (2) 110 samples from patients treated at MDACC on GOG protocol 0182; (3) 1300 samples from patients treated with carboplatin under protocol SCOTRCO.

It is preferred that the assay is validated by application to a larger sample for validation in a retrospective analysis of paraffin embedded samples from 700 moderate and high risk ovarian cancers (60% five year survival), the majority treated with platinum based therapy and 500 high risk cancers treated with cisplatinum and taxane.

In another embodiment, the assay can be used to determine the efficacy of traditional, current and new treatment protocols.

In another embodiment, elevated gene expression is detected using quantitative PCR. Primers can be created using the sequences of genes identified in Tables 1-6, the BAC end sequences listed in Tables 2-6, or the GenBank Accession genomic sequences listed above for 8q24.1, 11q13.3, and 20q13, to detect sequence amplification by signal amplification in gel electrophoresis. As is known in the art, primers or oligonucleotides are generally 15-40 bp in length, and usually flank unique sequence that can be amplified by methods such as polymerase chain reaction (PCR) or reverse transcriptase PCR(RT-PCR, also known as real-time PCR). Methods for RT-PCR and its optimization are known in the art. An example is the PROMEGA PCR Protocols and Guides, found at URL:<http://www.promega.com/guides/pcr_guide/default.htm>, and hereby incorporated by reference. Currently at least four different chemistries, TaqMan® (Applied Biosystems, Foster City, Calif., USA), Molecular Beacons, Scorpions® and SYBR® Green (Molecular Probes), are available for real-time PCR. All of these chemistries allow detection of PCR products via the generation of a fluorescent signal. TaqMan probes, Molecular Beacons and Scorpions depend on Förster Resonance Energy Transfer (FRET) to generate the fluorescence signal via the coupling of a fluorogenic dye molecule and a quencher moeity to the same or different oligonucleotide substrates. SYBR Green is a fluorogenic dye that exhibits little fluorescence when in solution, but emits a strong fluorescent signal upon binding to double-stranded DNA.

Two strategies are commonly employed to quantify the results obtained by real-time RT-PCR; the standard curve method and the comparative threshold method. In this method, a standard curve is first constructed from an RNA of known concentration. This curve is then used as a reference standard for extrapolating quantitative information for mRNA targets of unknown concentrations. Another quantitation approach is termed the comparative $C_t$ method. This involves comparing the $C_t$ values of the samples of interest with a control or calibrator such as a non-treated sample or RNA from normal tissue. The $C_t$ values of both the calibrator and the samples of interest are normalized to an appropriate endogenous housekeeping gene.

In one embodiment, elevated gene expression is detected using an RT-PCR assay to detect transcription levels or detected using a PCR assay to detect amplification of at least one gene from each amplicon region, preferably selected from the foregoing: MYC or PVT1 (8q), CCND1 (11q13.3), HE4 or WHDC2 (20q13.1), ZNF217 (20q13.2) PTK6 (20q13.3).

In a specific embodiment, the TaqMan probes and PVT1 primers used in an RT-PCR assay are SEQ ID NOS: 21-23, in order to detect the TaqMan amplicon SEQ ID NO: 20.

Tri-Locus Assay Kits.

The present invention further provides kits for use within any of the above diagnostic methods. Such kits typically comprise two or more components necessary for performing a diagnostic assay. Components may be compounds, reagents, containers and/or equipment.

In one embodiment, one container within a kit may contain a set of three FISH probes for detection of amplification at three loci, such as 8q24.1, 11q13.3 and 20q13.1. One or more additional containers may enclose elements, such as reagents or buffers, to be used in the assay. Such kits may also, or alternatively, contain a detection reagent as described above that contains a reporter group suitable for direct or indirect detection of antibody binding.

In another embodiment, the kit may be comprised of a set of PCR primers to detect sequence amplification genes found in Tables 1-6 or genomic sequences amplified in the 8q24, 11q13, or 20q11-13 regions. The kit would also contain such reagents as buffers, polymerase, Magnesium, or other elements necessary to carry out quantitative PCR.

Prognostic markers that identify subsets of patients with very poor survival prospects are of modest clinical importance unless therapies can be developed for these patients. Our approach to therapy for these patients is to develop inhibitors of genes that are over expressed in the regions of amplification associated with reduced survival. For example, candidate over expressed genes that are potential therapeutic targets have been identified in Table 1 in each of the regions of amplification. It is contemplated that these candidate genes may be over expressed in diseases including but not limited, cancers, lymphomas, cardiovascular diseases, cardiac hypertrophy, and infectious diseases.

The approaches to be taken will depend on the detailed characteristics of the genes, but in a preferred embodiment, will begin with strategies to inhibit RNA transcription since they can, in principal, be used to attack over expressed genes independent of their biochemical composition. Work in the past two decades on transcriptional inhibitors focused on oligodeoxynucleotides and ribozymes. These approaches have had some clinical success but delivery issues limited their clinical utility. Recently, however, advances in short interfering RNA (siRNA) technology and biological understanding have accelerated development of anti-gene therapies (Wall, N. R. & Shi, Y. Small RNA: can RNA interference be exploited for therapy? *Lancet* 362, 1401-3 (2003); Scanlon, K. J. Anti-genes: siRNA, ribozymes and antisense. *Curr Pharm Biotechnol* 5, 415-20 (2004); Buckingham, S. D., Esmaeili, B., Wood, M. & Sattelle, D. B. RNA interference: from model organisms towards therapy for neural and neuromuscular disorders. *Hum Mol Genet.* 13 Spec No 2, R275-88 (2004)). Promising therapeutic approaches include siRNAs complexed with cationic liposomes (Liao, Y., et al., Enhanced paclitaxel cytotoxicity and prolonged animal survival rate by a nonviral-mediated systemic delivery of E1A gene in orthotopic xenograft human breast cancer. *Cancer Gene Ther* 11, 594-602 (2004); Yano, J. et al. Antitumor activity of small interfering RNA/cationic liposome complex in mouse models of cancer. *Clin Cancer Res* 10, 7721-6 (2004)), virus vector-mediated RNAi (Zhao, N. et al. Knockdown of Mouse Adult beta-Globin Gene Expression in MEL Cells by Retrovirus Vector-Mediated RNA Interference. *Mol Biotechnol* 28, 195-200 (2004); Sumimoto, H. et al. Gene therapy for human small-cell lung carcinoma by inactivation of Skp-2 with virally mediated RNA interference. *Gene Ther* (2004)) and nanoparticles adapted for siRNA (Schiffelers, R. M. et al. Cancer siRNA therapy by tumor selective delivery with ligand-targeted sterically stabilized nanoparticle. *Nucleic Acids Res* 32, e149 (2004)). In one embodiment, siRNAs against the high priority targets complexed with cationic liposomes and small molecule approaches to inhibit the over expressed candidate genes will allow rapid development of this line of attack.

Our studies of ovarian cancer have combined genome scale analyses of gene expression and genome copy number in 250 serous ovarian cancer patients to identify specific aberrations and genes that are most strongly associated with reduced survival duration (see Progress for detailed information). These analyses have defined the location and frequency of occurrence of ~20 regions of genome copy number abnormality that are present in at least 30% of tumors. About half of these are copy number increases. Importantly, high level amplification in general and amplifications specifically at 8q24, 11q13 and 20q11-q13 are significantly associated with reduced survival duration in conventionally treated patients (surgical debulking with platinum and taxol adjuvant therapy; data not shown). Amplification at 8q24 is the strongest predictor of the three in ovarian cancer and has been shown by the results described herein to be a very strong predictor of poor outcome in breast cancer as well. The region of amplification associated with poor outcome is very close to the location of MYC and published FISH studies support the association of amplification of this region with reduced survival duration[26,27].

In one embodiment, genome wide analyses of genome copy number and gene expression in serous ovarian cancers showed that a region at chromosome 8q24 is amplified and over-expressed in approximately half of all cancers. Functional studies of PVT1 and other genes in regions of recurrent abnormality in ovarian and other cancers are herein described. We consider the following genes to be high priority therapeutic targets in diseases wherein they are over expressed and associated with short survival rates. They include MYC and PVT1 at 8q24; CCND1, PPFIA1 and EMS1 at 11q13 and PTK6, EEF1A2 and ZNF217 at 20q11-13. The GenBank Accession numbers or coordinates for PVT1 and other candidate genes are shown in Table 1 shown above.

PVT1 and MYC are particularly important in the context of this application because they are at the site of recurrent high level amplification at 8q24 that is mostly strongly associated with short survival duration in ovarian and breast cancer. These genes were discovered by measuring gene expression levels using Affymetrix expression profiling and copy number levels using array CGH in ~80 ovarian cancers for which outcome information was available. Analyses of correlations between gene expression and genome copy number showed that over 1000 genes are deregulated by recurrent genome aberrations including several in the three regions of amplification associated with reduced survival duration.

Over expression of PVT1 but not MYC is strongly associated with short survival in our analyses ($p<0.001$) and in published studies (ref, $p=0.06$). CCND1, PPFIA1 and EMS1 map to the amplified region of chromosome 11q13 associated with reduced survival duration. PTK6, EEF1A2 and ZNF217 map to chromosome 20q11-13 near the locus most strongly associated with reduced survival duration. Modulation of the expression levels of several of these genes in ovarian cancer cell lines and/or ovarian surface epithelial cells should significantly alter proliferation, invasion and/or apoptosis.

Thus, herein is described complementary strategies to (a) develop and fully validate markers that identify patients with serous ovarian cancer that will survive less than 2 years under conventional treatment and (b) develop and evaluate therapies that will be preferentially effective in this group of patients and provide improved ovarian cancer management. Marker development is expected to be complete and fully validated within a short time and available commercially shortly thereafter. Prototypic therapies against PVT1 and other outcome-associated genes will be developed as described and tested in preclinical models.

In a preferred embodiment, PVT1 is the candidate gene target for development of therapeutics and diagnostic assays. In one embodiment, an assay to detect elevated PVT1 expression as a predictor of poor response to taxol plus platinum based therapies in serous ovarian cancers. In such an assay, elevated PVT1 expression can be detected using methods known in the art. It is contemplated that elevated PVT1 expression can be detected in a subject by testing various tissues and bodily fluids, including but not limited to blood and serum.

In another embodiment, elevated PVT1 expression is detected using FISH to detect 8q24 amplification or PVT1 amplification. For example, one can create probes that hybridize to the 8q24 region, found in GenBank Accession No: NT_008046. Probes can be created based upon the sequences of PVT1 using the methods as described earlier. In a specific embodiment, probes can be created by methods described above based upon the sequence of PVT1 in SEQ ID NO: 1 or SEQ ID NO: 2, or genomic sequence containing and flanking PVT in GenBank Accession No. NT_008046, *Homo sapiens* chromosome 8 genomic contig, which is hereby incorporated by reference. Other useful sequences for making probes and other sequences in the present invention include but are not limited, AY33608 *Homo sapiens* PVT1 (PVT1) gene, exon 1 and 5' UTR; XM_372058, PREDICTED: *Homo sapiens* Pvt1 oncogene homolog, MYC activator (mouse) (PVT1), mRNA; BC033263, *Homo sapiens* Pvt1 oncogene homolog, MYC activator (mouse), mRNA (cDNA clone IMAGE:5517530), with apparent retained intron; and M26714, *Homo sapiens* MYC activator (PVT1) gene, exon 1, all of which are hereby incorporated by reference. Specifically GenBank Accession numbers for PVT1 cDNAs are M34428 and XM_37058 are hereby incorporated by reference.

In another embodiment, elevated PVT1 expression is detected using a PCR assay to detect PVT1 amplification. Primers can be created using the sequences of SEQ ID NO: 1 or SEQ ID NO: 2 or NT_008046, the genomic sequence, to detect sequence amplification by signal amplification in gel electrophoresis. As is known in the art, primers or oligonucleotides are generally 15-40 bp in length, and usually flank unique sequence that can be amplified by methods such as polymerase chain reaction (PCR) or reverse transcriptase PCR. In yet another embodiment, elevated PVT1 expression is detected using an RT-PCR assay to detect PVT1 transcription levels.

It is further contemplated and would be well accepted by one with skill in the art that antibodies can be made to any of the high priority candidate genes listed above to detect specific gene amplification at the three loci. In a preferred embodiment, elevated PVT1 expression is detected using an immunochemical assay to detect PVT1 protein levels. Anti-PVT1 specific antibodies can be made by general methods known in the art. A preferred method of generating these antibodies is by first synthesizing peptide fragments. These peptide fragments should likely cover unique coding regions in the candidate gene. Since synthesized peptides are not always immunogenic by their own, the peptides should be conjugated to a carrier protein before use. Appropriate carrier proteins include but are not limited to Keyhole limpet hemacyanin (KLH). The conjugated phospho peptides should then be mixed with adjuvant and injected into a mammal, preferably a rabbit through intradermal injection, to elicit an immunogenic response. Samples of serum can be collected and tested by ELISA assay to determine the titer of the antibodies and then harvested.

Polyclonal (e.g., anti-PVT1) antibodies can be purified by passing the harvested antibodies through an affinity column. Monoclonal antibodies are preferred over polyclonal antibodies and can be generated according to standard methods known in the art of creating an immortal cell line which expresses the antibody.

Nonhuman antibodies are highly immunogenic in human and that limits their therapeutic potential. In order to reduce their immunogenicity, nonhuman antibodies need to be humanized for therapeutic application. Through the years, many researchers have developed different strategies to humanize the nonhuman antibodies. One such example is using "HuMAb-Mouse" technology available from MEDAREX, Inc. and disclosed by van de Winkel, in U.S. Pat. No. 6,111,166 and hereby incorporated by reference in its entirety. "HuMAb-Mouse" is a strain of transgenic mice which harbor the entire human immunoglobin (Ig) loci and thus can be used to produce fully human monoclonal antibodies such as monoclonal anti-PVT1 antibodies.

In one embodiment, down regulation of PVT1 at 8q24 and other high priority genes at 11q13 and 20q13 will be made using inhibitors preferentially toxic to cells detected as overamplified. It is contemplated that such down regulation will enhance response to platinum and taxane compounds because amplification at 8q24, 11q13 and 20q13 increases resistance to carboplatin and/or pacitaxel.

In a preferred embodiment, identifying genes that are over-expressed in regions of amplification associated with reduced survival duration and for which inhibitors induce apoptosis in ovarian cancer cell lines in which the target is amplified is performed as described in Example 1 using PVT1 as the prototype. However, levels of amplification and gene expression may vary substantially between serous ovarian cancers. These quantitative differences and the presence of other aberrations may influence the degree of response to amplicon gene targeted therapies.

To test that amplification of the target gene as assessed using FISH is necessary and sufficient for response to amplicon gene targeted therapeutics in ovarian cancers, the expression of target genes in a panel of ovarian cancer cell lines are manipulated and/or inhibited. FIG. 1*b* shows the frequencies of recurrent genomic aberrations in 21 ovarian cancer cell lines (14 more are in analysis). In general, the sample-to-sample heterogeneity in levels of recurrent amplification and gene expression reflect those found in primary tumors.

In a preferred embodiment, the expression of PVT1 and other high priority apoptosis-associated genes is manipulated. In one embodiment, such manipulation can be made using optimized siRNAs. See Hannon, G. J. *RNA interference* (2002); Plasterk, R. H. in *Science* 1263-5 (2002); and Elbashir, S. M. et al. in *Nature* 494-8 (2001). Strong Pearson correlations between target gene amplification/expression levels and pro-apoptotic effects of siRNAs will indicate that copy number/expression levels determine the extent of apoptotic responses to target gene inhibitors. Spearman rank test correlations between amplification detected using the tri-locus test and the level of induced apoptosis will indicate that the FISH test predicts response to targeted therapeutics.

In another embodiment, treatment of amplified cells simultaneously with siRNAs against the apoptosis associated genes plus carboplatin or pacitaxel should result in the inhibition of apoptosis-associated amplicon genes and enhance patient response to carboplatin and pacitaxil. Greater than additive induction of apoptosis in these dual treatment experiments will indicate a synergistic effect. Studies can be conducted further to transfect cells that do not amplify/over express the target genes and determine whether over expression of the putative "anti-apoptotic" genes decreases sensitivity to carboplatin and/or pacitaxel.

The invention further provides for compounds to treat patients with elevated PVT1 expression. In a preferred embodiment, the compound is a PVT1 inhibitor such as, an antisense oligonucleotide; a siRNA olignonucleotide; a small molecule that interferes with PVT1 function; a viral vector producing a nucleic acid sequence that inhibits PVT1; or an aptamer.

High throughput methods can be used to identify PVT1 inhibitors such as siRNA and/or small molecular inhibitor formulations to deliver PVT1 (and other) inhibitors efficiently to cultured cells and xenografts. PVT1 (and other) inhibitory formulations will be preferentially effective against xenografts that are amplified at the target loci and that these will enhance response to platinum and taxane compounds. Effective formulations using such methods as described above or in Example 2 will be developed for clinical application.

High Throughput Screening.

In one embodiment, high throughput screening (HTS) methods are used to identify compounds that inhibit PVT1 and other candidate genes which are related to drug resistance and reduced survival rate, such as those amplified in the chromosomal 8q24.1, 11q13.3 and 20q11-q13 regions. In a preferred embodiment, the candidate genes would include MYC and PVT1 at 8q24; CCND1, PPFIA1 and EMS1 at 11q13 and PTK6, EEF1A2 and ZNF217 at 20q13. HTS methods involve providing a combinatorial chemical or peptide library containing a large number of potential therapeutic compounds (i.e., compounds that inhibit PVT1 and other candidate genes which are related to drug resistance). Such "libraries" are then screened in one or more assays, as described herein, to identify those library members (particular peptides, chemical species or subclasses) that display the desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g. U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g. U.S. Pat. No. 5,539,083), antibody libraries (see, e.g. Vaughn et al., *Nature Biotechnology*, 14(3):309-314 (1996) and PCT/US96/10287), carbohydrate libraries (see, e.g. Liang et al., *Science*, 274:1520-1522 (1996) and U.S. Pat. No. 5,593,853), small organic molecule libraries (see, e.g. benzodiazepines, Baum C&EN, January 18, page 33 (1993); isoprenoids, U.S. Pat. No. 5,569,588; thiazolidinones and metathiazanones, U.S. Pat. No. 5,549, 974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g. ECIS™, Applied BioPhysics Inc., Troy, N.Y., MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

Inhibitor Oligonucleotide and RNA interference (RNAi) Sequence Design.

In one embodiment, known methods are used to identify sequences that inhibit PVT1 and other candidate genes which are related to drug resistance and reduced survival rate, such as high priority targets MYC and PVT1 at 8q24; CCND1 at 11q13 and ZNF217 at 20q13. Such inhibitors may include but are not limited to, siRNAoligonucleotides, antisense oligonucleotides, peptide inhibitors and aptamer sequences that bind and act to inhibit PVT1 expression and/or function.

In one embodiment, RNA interference is used to generate small double-stranded RNA (small interference RNA or siRNA) inhibitors to affect the expression of a candidate gene generally through cleaving and destroying its cognate RNA. Small interference RNA (siRNA) is typically 19-22 nt double-stranded RNA. siRNA can be obtained by chemical synthesis or by DNA-vector based RNAi technology. Using DNA vector based siRNA technology, a small DNA insert (about 70 bp) encoding a short hairpin RNA targeting the gene of interest is cloned into a commercially available vector. The insert-containing vector can be transfected into the cell, and expressing the short hairpin RNA. The hairpin RNA is rapidly processed by the cellular machinery into 19-22 nt double stranded RNA (siRNA). In a preferred embodiment, the siRNA is inserted into a suitable RNAi vector because siRNA made synthetically tends to be less stable and not as effective in transfection.

siRNA can be made using methods and algorithms such as those described by Wang L, Mu F Y. (2004) A Web-based Design Center for Vector-based siRNA and siRNA cassette. *Bioinformatics.* (In press); Khvorova A, Reynolds A, Jayasena S D. (2003) Functional siRNAs and miRNAs exhibit strand bias. *Cell.* 115(2):209-16; Harborth J, Elbashir S M, Vandenburgh K, Manning a H, Scaringe S A, Weber K, Tuschl T. (2003) Sequence, chemical, and structural variation of small interfering RNAs and short hairpin RNAs and the effect on mammalian gene silencing. *Antisense Nucleic Acid Drug Dev.* 13(2):83-105; Reynolds A, Leake D, Boese Q, Scaringe S, Marshall W S, Khvorova A. (2004) Rational siRNA design for RNA interference. *Nat. Biotechnol.* 22(3): 326-30 and Ui-Tei K, Naito Y, Takahashi F, Haraguchi T, Ohki-Hamazaki H, Juni A, Ueda R, Saigo K. (2004) Guidelines for the selection of highly effective siRNA sequences for mammalian and chick RNA interference. *Nucleic Acids Res.* 32(3):936-48, which are hereby incorporated by reference.

Other tools for constructing siRNA sequences are web tools such as the siRNA Target Finder and Construct Builder available from GenScript (http://www.genscript.com), Oligo Design and Analysis Tools from Integrated DNA Technologies (URL:<http://www.idtdna.com/SciTools/SciTools.aspx>), or siDESIGN™ Center from Dharmacon, Inc. (URL:<http://design.dharmacon.com/default.aspx?source=0>). siRNA are suggested to built using the ORF (open reading frame) as the target selecting region, preferably 50-100 nt downstream of the start codon. Because siRNAs function at the mRNA level, not at the protein level, to design an siRNA, the precise target mRNA nucleotide sequence may be required. Due to the degenerate nature of the genetic code and codon bias, it is difficult to accurately predict the correct nucleotide sequence from the peptide sequence. Additionally, since the function of siRNAs is to cleave mRNA sequences, it is important to use the mRNA nucleotide sequence and not the genomic sequence for siRNA design, although as noted in the Examples, the genomic sequence can be successfully used for siRNA design. However, designs using genomic information might inadvertently target introns and as a result the siRNA would not be functional for silencing the corresponding mRNA.

Rational siRNA design should also minimize off-target effects which often arise from partial complementarity of the sense or antisense strands to an unintended target. These effects are known to have a concentration dependence and one way to minimize off-target effects is often by reducing siRNA concentrations. Another way to minimize such off-target effects is to screen the siRNA for target specificity.

In one embodiment, the siRNA can be modified on the 5'-end of the sense strand to present compounds such as fluorescent dyes, chemical groups, or polar groups. Modification at the 5'-end of the antisense strand has been shown to interfere with siRNA silencing activity and therefore this position is not recommended for modification. Modifications at the other three termini have been shown to have minimal to no effect on silencing activity.

It is recommended that primers be designed to bracket one of the siRNA cleavage sites as this will help eliminate possible bias in the data (i.e., one of the primers should be upstream of the cleavage site, the other should be downstream of the cleavage site). Bias may be introduced into the experiment if the PCR amplifies either 5' or 3' of a cleavage site, in part because it is difficult to anticipate how long the cleaved mRNA product may persist prior to being degraded. If the amplified region contains the cleavage site, then no amplification can occur if the siRNA has performed its function.

In a preferred embodiment, two cDNA sequences were used to design the PVT1 siRNA, M34428 (SEQ ID NO: 1) and XM_372058 (SEQ ID NO: 2). The M34428 sequence was sent to a commercial company to design the siRNA. SEQ ID NOS: 1 and 2 were used to design primers and Taqman probe for quantitative PCR using the 'Primer Express 2.0' program from ABI Biosystems (Foster City, Calif.). For other siRNA sequences (SEQ ID NOS: 5-17), the webdesigning tool from Genescript (URL: <http://www.genescript.com>) was used since it provides the top candidates and also performs BLAST screening (Altschul, S. F., Gish, W., Miller, W., Myers, E. W. & Lipman, D. J. (1990) "Basic local alignment search tool." *J. Mol. Biol.* 215:403-410) on each resulting siRNA sequence. Five siRNA sequences were chosen that were within the overlapping regions of M34428 and XM_372058 and are SEQ ID NOS: 8-17.

The five siRNA sequences for XM_372058 were chosen because they overlap with the M34428 sequence, and because all five siRNAs were found within the XM_372058 predicted coding region (bp 379-777). Thus siRNAs found within predicted coding regions may indicate useful siRNAs for the present invention. For sequences such as M34428, where the coding region is not known or predicted, it may be prudent to perform a study such as a 5'-RACE test to determine the actual coding sequence.

Figure 11A:
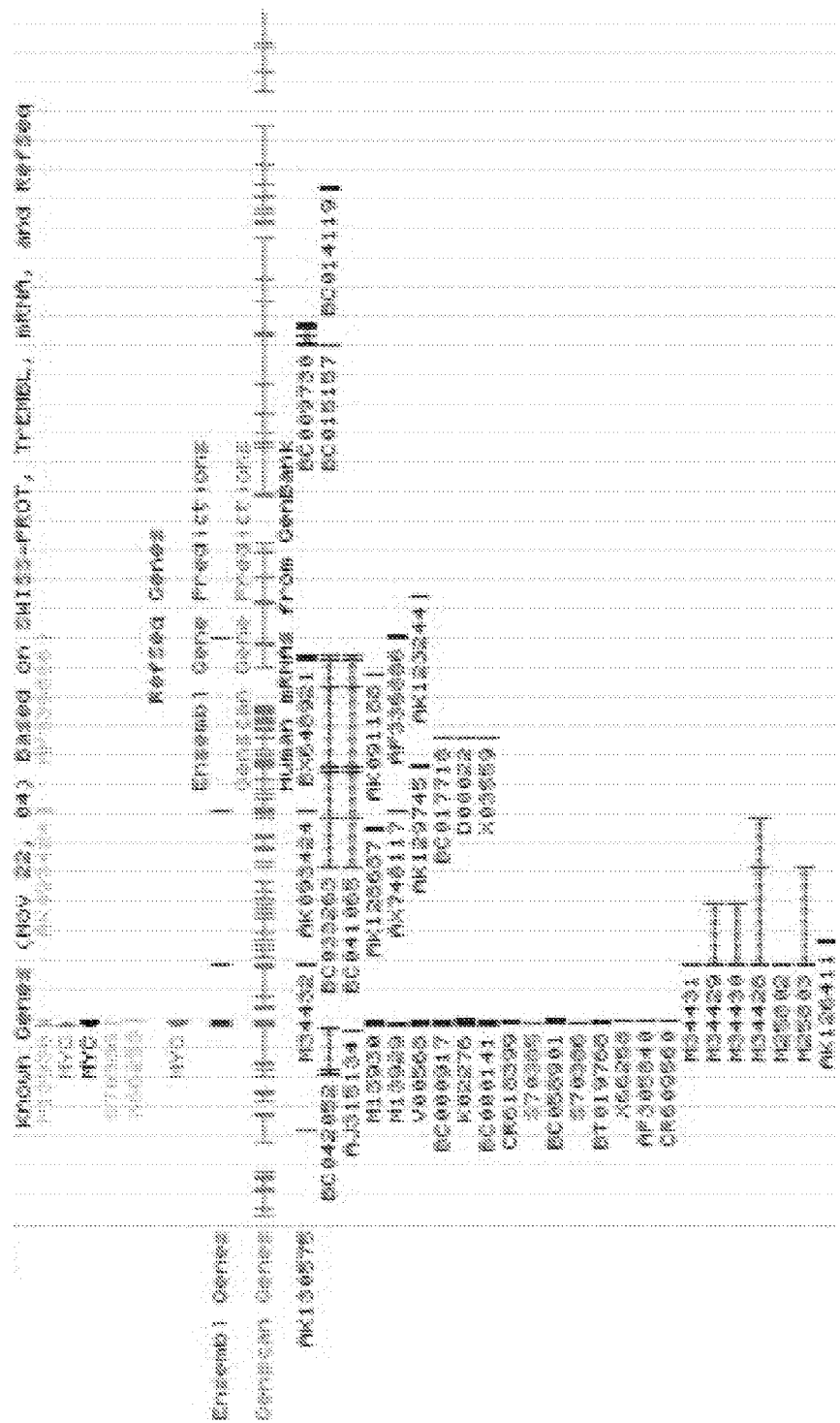
FIG. 11A shows the genomic map of the MYC amplicon in chromosome 8.

FIG. 11A shows the map for the 8q24 amplicon and also how the 8q24 amplicon was defined from tumors and cell lines. The genome distance coordinates are in the May 2004 draft from UCSC genome browser. FIG. 11B is the amplicon as derived from 106 serous tumors, and FIG. 11C is the amplicon as derived from cell lines. The region in cell lines is wider than the one from tumors because the genome distance coordinates for 8q24 were based on the tumors.

In another embodiment, antisense oligonucleotides ("oligos") can be designed to inhibit PVT1 and other candidate gene function. Antisense oligonucleotides are short single-stranded nucleic acids, which function by selectively hybridizing to their target mRNA, thereby blocking translation. Translation is inhibited by either RNase H nuclease activity at the DNA:RNA duplex, or by inhibiting ribosome progression, thereby inhibiting protein synthesis. This results in discontinued synthesis and subsequent loss of function of the protein for which the target mRNA encodes.

In a preferred embodiment, antisense oligos are phosphorothioated upon synthesis and purification, and are usually 18-22 bases in length. It is contemplated that the PVT1 and other candidate gene antisense oligos may have other modifications such as 2'-O-Methyl RNA, methylphosphonates, chimeric oligos, modified bases and many others modifications, including fluorescent oligos.

In a preferred embodiment, active antisense oligos should be compared against control oligos that have the same general chemistry, base composition, and length as the antisense oligo. These can include inverse sequences, scrambled sequences, and sense sequences. The inverse and scrambled are recommended because they have the same base composition, thus same molecular weight and Tm as the active antisense oligonucleotides. Rational antisense oligo design should consider, for example, that the antisense oligos do not anneal to an unintended mRNA or do not contain motifs known to invoke immunostimulatory responses such as four contiguous G residues, palindromes of 6 or more bases and CG motifs.

Antisense oligonucleotides can be used in vitro in most cell types with good results. However, some cell types require the use of transfection reagents to effect efficient transport into cellular interiors. It is recommended that optimization experiments be performed by using differing final oligonucleotide concentrations in the 1-5 µm range with in most cases the addition of transfection reagents. The window of opportunity, i.e., that concentration where you will obtain a reproducible antisense effect, may be quite narrow, where above that range you may experience confusing non-specific, non-antisense effects, and below that range you may not see any results at all. In a preferred embodiment, down regulation of the targeted mRNA (e.g. PVT1 mRNA SEQ ID NO: 1) will be demonstrated by use of techniques such as northern blot, real-time PCR, cDNA/oligo array or western blot. The same endpoints can be made for in vivo experiments, while also assessing behavioral endpoints.

For cell culture, antisense oligonucleotides should be resuspended in sterile nuclease-free water (the use of DEPC-treated water is not recommended). Antisense oligonucleotides can be purified, lyophilized, and ready for use upon re-suspension. Upon suspension, antisense oligonucleotide stock solutions may be frozen at −20° C. and stable for several weeks.

In another embodiment, aptamer sequences which bind to specific RNA or DNA sequences can be made. Aptamer sequences can be isolated through methods such as those disclosed in co-pending U.S. patent application Ser. No. 10/934,856, entitled, "Aptamers and Methods for their Invitro Selection and Uses Thereof," which is hereby incorporated by reference.

It is contemplated that the sequences described herein may be varied to result in substantially homologous sequences which retain the same function as the original. As used herein, a polynucleotide or fragment thereof is "substantially homologous" (or "substantially similar") to another if, when optimally aligned (with appropriate nucleotide insertions or deletions) with the other polynucleotide (or its complementary strand), using an alignment program such as BLASTN (Altschul, S. F., Gish, W., Miller, W., Myers, E. W. & Lipman, D. J. (1990) "Basic local alignment search tool." *J. Mol. Biol.* 215:403-410), and there is nucleotide sequence identity in at least about 80%, preferably at least about 90%, and more preferably at least about 95-98% of the nucleotide bases.

Recombinant Expression.

PVT1 inhibitors such as the siRNA PVT1 inhibitor described herein can also be expressed recombinantly. In general, the nucleic acid sequences encoding PVT1 inhibitors such as the siRNA PVT1 inhibitor and related nucleic acid sequence homologues can be cloned. This aspect of the invention relies on routine techniques in the field of recombinant genetics. Generally, the nomenclature and the laboratory procedures in recombinant DNA technology described herein are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 1994)).

PVT1 and other candidate genes which are related to drug resistance and reduced survival rate are first cloned from cDNA and genomic DNA libraries or isolated using amplification techniques with oligonucleotide primers. For example, sequences of candidate genes amplified in the chromosomal 8q24.1, 11q13.3 and 20q13 regions and related to reduced survival rates, such as MYC and PVT1 at 8q24; CCND1, PPFIA1 and EMS1 at 11q13 and PTK6, EEF1A2 and ZNF217 at 20q13 are typically isolated from nucleic acid (genomic or cDNA) libraries by hybridizing with a nucleic acid probe, the sequence of which can be derived from any one of SEQ ID NOS: 1-2, or a subsequence thereof. In another embodiment, RNA and genomic DNA of MYC and PVT1 at 8q24; CCND1, PPFIA1 and EMS1 at 11q13 and PTK6, EEF1A2 and ZNF217 at 20q13 can be isolated from any mammal including: primates such as humans, monkeys, and chimpanzees; rodents, including mice and rats. Methods for making and screening cDNA libraries and genomic DNA libraries are well known (see, e.g., Gubler & Hoffman, Gene 25:263-269 (1983); Sambrook et al., supra; Ausubel et al., supra; Benton & Davis, *Science* 196:180-182 (1977); and Grunstein et al., *PNAS USA*, 72:3961-3965 (1975)).

Nucleic acids encoding sequences of candidate genes amplified in the chromosomal 8q24.1, 11q13.3 and 20q13 regions and related to reduced survival rates, such as MYC and PVT1 at 8q24; CCND1, PPFIA1 and EMS1 at 11q13 and PTK6, EEF1A2 and ZNF217 at 20q13, can also be isolated from expression libraries using antibodies as probes. Such polyclonal or monoclonal antibodies can be raised using, for example, the polypeptides comprising the sequences set forth in SEQ ID NOS: 1-2, and subsequences thereof, using methods known in the art (see, e.g., Harlow and Lane, Antibodies: A Laboratory Manual (1988)).

Substantially identical nucleic acids encoding sequences of candidate genes amplified in the chromosomal 8q24.1, 11q13.3 and 20q11.2 regions and related to reduced survival rates, such as MYC and PVT1 at 8q24; CCND1, PPFIA1 and EMS1 at 11q13 and PTK6, EEF1A2 and ZNF217 at 20q13 can be isolated using nucleic acid probes and oligonucleotides under stringent hybridization conditions, by screening libraries.

Alternatively, expression libraries can be used to clone these sequences, by detecting expressed homologues immunologically with antisera or purified antibodies made against the core domain of nucleic acids encoding sequences of candidate genes amplified in the chromosomal 8q24.1, 11q13.3 and 20q13 regions and related to reduced survival rates, such as MYC and PVT1 at 8q24; CCND1, PPFIA1 and EMS1 at 11q13 and PTK6, EEF1A2 and ZNF217 at 20q13 which also recognize and selectively bind to the homologue.

Gene expression of candidate genes amplified in the chromosomal 8q24.1, 11q13.3 and 20q13 regions and related to reduced survival rates, such as MYC and PVT1 at 8q24, can also be analyzed by techniques known in the art, e.g., reverse transcription and amplification of mRNA, isolation of total RNA or poly A+RNA, northern blotting, dot blotting, in situ hybridization, RNase protection, probing DNA microchip arrays, and the like.

To obtain high level expression of a cloned gene or nucleic acid sequence, such as those cDNAs encoding nucleic acid sequences encoding PVT1 inhibitors such as the siRNA PVT1 inhibitor and related nucleic acid sequence homologues, one typically subclones an inhibitor peptide sequence (e.g., nucleic acid sequences encoding PVT1 inhibitors such as the siRNA PVT1 inhibitor and related nucleic acid sequence homologue or a sequence encoding SEQ ID NOS: 3-17) into an expression vector that is subsequently transfected into a suitable host cell. The expression vector typically contains a strong promoter or a promoter/enhancer to direct transcription, a transcription/translation terminator, and for a nucleic acid encoding a protein, a ribosome binding site for translational initiation. The promoter is operably linked to the nucleic acid sequence encoding PVT1 inhibitors such as the siRNA PVT1 inhibitor or a subsequence thereof. Suitable bacterial promoters are well known in the art and described, e.g., in Sambrook et al. and Ausubel et al. The elements that are typically included in expression vectors also include a replicon that functions in a suitable host cell such as *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to the recombinant PVT1 inhibitors peptides to provide convenient methods of isolation, e.g., His tags. In some case, enzymatic cleavage sequences (e.g., Met-(His)g-Ile-Glu-GLy-Arg which form the Factor Xa cleavage site) are added to the recombinant PVT1 inhibitor peptides. Bacterial expression systems for expressing the PVT1 inhibitor peptides and nucleic acids are available in, e.g., *E. coli, Bacillus* sp., and *Salmonella* (Palva et al., Gene 22:229-235 (1983); Mosbach et al., Nature 302:543-545 (1983). Kits for such expression systems are commercially available. Eukaryotic expression systems for mammalian cells, yeast, and insect cells are well known in the art and are also commercially available.

Standard transfection methods are used to produce cell lines that express large quantities of PVT1 inhibitor, which can then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of cells is performed according to standard techniques (see, e.g., Morrison, J. Bact. 132:349-351 (1977); Clark-Curtiss & Curtiss, Methods in Enzymology 101:347-362 (Wu et al., eds, 1983). For example, any of the well known procedures for introducing foreign nucleotide sequences into host cells may be used. These include the use of calcium phosphate transfection, lipofectamine, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing PVT1 inhibitor peptides and nucleic acids.

After the expression vector is introduced into the cells, the transfected cells are cultured under conditions favoring expression of PVT1 inhibitors such as the siRNA PVT1 inhibitor and related nucleic acid sequence homologues.

Methods of Treatment.

The PVT1 inhibitor peptides and nucleic acids of the present invention, such as the siRNA PVT1 inhibitor, also can be used to treat or prevent a variety of disorders associated with reduced survival rate, especially as related to cancers. The peptides and nucleic acids are administered to a patient in an amount sufficient to elicit a therapeutic response in the patient (e.g., reduction of tumor size and growth rate, prolonged survival rate, reduction in concurrent cancer therapeutics administered to patient). An amount adequate to accomplish this is defined as "therapeutically effective dose or amount."

The peptides and nucleic acids of the invention can be administered directly to a mammalian subject using any route known in the art, including e.g., by injection (e.g., intravenous, intraperitoneal, subcutaneous, intramuscular, or intradermal), inhalation, transdermal application, rectal administration, or oral administration.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there are a wide variety of suitable formulations of pharmaceutical compositions of the present invention (see, e.g. Remington's Pharmaceutical Sciences, 17th ed., 1989).

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

Administration of the peptides and nucleic acids of the invention can be in any convenient manner, e.g., by injection, intratumoral injection, intravenous and arterial stents (including eluting stents), cather, oral administration, inhalation, transdermal application, or rectal administration. In some cases, the peptides and nucleic acids are formulated with a pharmaceutically acceptable carrier prior to administration. Pharmaceutically acceptable carriers are determined in part by the particular composition being administered (e.g., nucleic acid or polypeptide), as well as by the particular method used to administer the composition. Accordingly, there are a wide variety of suitable formulations of pharmaceutical compositions of the present invention (see, e.g., *Remington's Pharmaceutical Sciences*, $17^{th}$ ed., 1989).

The dose administered to a patient, in the context of the present invention should be sufficient to effect a beneficial therapeutic response in the patient over time. The dose will be determined by the efficacy of the particular vector (e.g. peptide or nucleic acid) employed and the condition of the patient, as well as the body weight or surface area of the patient to be treated. The size of the dose also will be determined by the existence, nature, and extent of any adverse side-effects that accompany the administration of a particular peptide or nucleic acid in a particular patient.

In determining the effective amount of the vector to be administered in the treatment or prophylaxis of diseases or disorder associated with the disease, the physician evaluates circulating plasma levels of the polypeptide or nucleic acid, polypeptide or nucleic acid toxicities, progression of the disease (e.g., ovarian cancer), and the production of antibodies that specifically bind to the peptide. Typically, the dose equivalent of a polypeptide is from about 0.1 to about 50 mg per kg, preferably from about 1 to about 25 mg per kg, most preferably from about 1 to about 20 mg per kg body weight. In general, the dose equivalent of a naked c acid is from about 1 µg to about 100 µg for a typical 70 kilogram patient, and doses of vectors which include a viral particle are calculated to yield an equivalent amount of therapeutic nucleic acid.

For administration, polypeptides and nucleic acids of the present invention can be administered at a rate determined by the LD-50 of the polypeptide or nucleic acid, and the side-effects of the polypeptide or nucleic acid at various concentrations, as applied to the mass and overall health of the patient. Administration can be accomplished via single or divided doses, e.g. doses administered on a regular basis (e.g. daily) for a period of time (e.g., 2, 3, 4, 5, 6, days or 1-3 weeks or more).

In certain circumstances it will be desirable to deliver the pharmaceutical compositions comprising the PVT1 inhibitor peptides and nucleic acids disclosed herein parenterally, intravenously, intramuscularly, or even intraperitoneally as described in U.S. Pat. No. 5,543,158; U.S. Pat. No. 5,641,515 and U.S. Pat. No. 5,399,363. Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g. glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g. *Remington's Pharmaceutical Sciences*, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

To date, most studies have been performed with siRNA formulated in sterile saline or phosphate buffered saline (PBS) that has ionic character similar to serum. There are minor differences in PBS compositions (with or without calcium, magnesium, etc.) and investigators should select a formulation best suited to the injection route and animal employed for the study. Lyophilized oligonucleotides and standard or siSTABLE siRNAs are readily soluble in aqueous solution and can be resuspended at concentrations as high as 2.0 mM. However, viscosity of the resultant solutions can sometimes affect the handling of such concentrated solutions.

While lipid formulations have been used extensively for cell culture experiments, the attributes for optimal uptake in cell culture do not match those useful in animals. The principle issue is that the cationic nature of the lipids used in cell culture leads to aggregation when used in animals and results in serum clearance and lung accumulation. Polyethylene glycol complexed-liposome formulations are currently under investigation for delivery of siRNA by several academic and industrial investigators, including Dharmacon, but typically require complex formulation knowledge. There are a few reports that cite limited success using lipid-mediated delivery of plasmids or oligonucleotides in animals.

Oligonucleotides can also be administered via bolus or continuous administration using an ALZET mini-pump (DURECT Corporation). Caution should be observed with bolus administration as studies of antisense oligonucleotides demonstrated certain dosing-related toxicities including hind limb paralysis and death when the molecules were given at high doses and rates of bolus administration. Studies with antisense and ribozymes have shown that the molecules distribute in a related manner whether the dosing is through intravenous (IV), subcutaneous (sub-Q), or intraperitoneal (IP) administration. For most published studies, dosing has been conducted by IV bolus administration through the tail vein. Less is known about the other methods of delivery, although they may be suitable for various studies. Any method of administration will require optimization to ensure optimal delivery and animal health.

For bolus injection, dosing can occur once or twice per day. The clearance of oligonucleotides appears to be biphasic and a fairly large amount of the initial dose is cleared from the urine in the first pass. Dosing should be conducted for a fairly long term, with a one to two week course of administration being preferred. This is somewhat dependent on the model being examined, but several metabolic disorder studies in rodents that have been conducted using antisense oligonucleotides have required this course of dosing to demonstrate clear target knockdown and anticipated outcomes.

Liposomes. In certain embodiments, the inventors contemplate the use of liposomes, nanocapsules, microparticles, microspheres, lipid particles, vesicles, and the like, for the administration of the PVT1 inhibitory peptides and nucleic acids of the present invention. In particular, the compositions of the present invention may be formulated for delivery either encapsulated in a lipid particle, a liposome, a vesicle, a nanosphere, or a nanoparticle or the like. In one embodiment, the PVT1siRNA inhibitors (e.g., any one of SEQ ID NOS: 3-17) are entrapped in a liposome for delivery as described in Example 5.

The formation and use of liposomes is generally known to those of skill in the art (see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-times (Gabizon & Papahadjopoulos, 1988; Allen and Choun, 1987; U.S. Pat. No. 5,741,516). Further, various methods of liposome and liposome like preparations as potential drug carriers have been reviewed (Takakura, 1998; Chandran et al., 1997; Margalit, 1995; U.S. Pat. No. 5,567,434; U.S. Pat. No. 5,552,157; U.S. Pat. No. 5,565,213; U.S. Pat. No. 5,738,868 and U.S. Pat. No. 5,795,587).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 m. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

Targeting is generally not a limitation in terms of the present invention. However, should specific targeting be desired, methods are available for this to be accomplished. For example, antibodies may be used to bind to the liposome surface and to direct the liposomes and its contents to particular cell types. Carbohydrate determinants (glycoprotein or glycolipid cell-surface components that play a role in cell-cell recognition, interaction and adhesion) may also be used as recognition sites as they have potential in directing liposomes to particular cell types.

Alternatively, the invention provides for pharmaceutically-acceptable nanocapsule formulations of the compositions of the present invention. Nanocapsules can generally entrap compounds in a stable and reproducible way (Henry-Michelland et al., 1987; Quintanar-Guerrero et al., 1998; Douglas et al., 1987). To avoid side effects due to intracellular polymeric overloading, such ultrafine particles (sized around 0.1 m) should be designed using polymers able to be degraded in vivo. Biodegradable polyalkyl-cyanoacrylate nanoparticles that meet these requirements are contemplated for use in the present invention. Such particles may be are easily made, as described (Couvreur et al., 1980; 1988; zur Muhlen et al., 1998; Zambaux et al. 1998; Pinto-Alphandry et al., 1995 and U.S. Pat. No. 5,145,684).

Gene Therapy.

In certain embodiments, the nucleic acids encoding inhibitory PVT1 peptides and nucleic acids of the present invention can be used for transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid, under the control of a promoter, then expresses an inhibitory PVT1 peptides and nucleic acids of the present invention, thereby mitigating the effects of over amplification of a candidate gene associated with reduced survival rate.

Such gene therapy procedures have been used to correct acquired and inherited genetic defects, cancer, and other diseases in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808-813 (1992); Nabel & Felgner, TIBTECH 11:211-217 (1993); Mitani & Caskey, TIBTECH 11:162-166 (1993); Mulligan, *Science* 926-932 (1993); Dillon, TIBTECH 11:167-175 (1993); Miller, *Nature* 357:455-460 (1992); Van Brunt, *Biotechnology* 6(10): 1149-1154 (1998); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* (Doerfler & Böhm eds., 1995); and Yu et al., *Gene Therapy* 1:13-26 (1994)).

For delivery of nucleic acids, viral vectors may be used. Suitable vectors include, for example, herpes simplex virus vectors as described in Lilley et al., *Curr. Gene Ther.* 1(4): 339-58 (2001), alphavirus DNA and particle replicons as described in e.g. Polo et al., *Dev. Biol.* (Basel) 104:181-5 (2000), Epstein-Barr virus (EBV)-based plasmid vectors as described in, e.g., Mazda, *Curr. Gene Ther.* 2(3):379-92 (2002), EBV replicon vector systems as described in e.g., Otomo et al., *J. Gene Med.* 3(4):345-52 (2001), adeno-virus associated viruses from rhesus monkeys as described in e.g., Gao et al., *PNAS USA.* 99(18):11854 (2002), adenoviral and adeno-associated viral vectors as described in, e.g. Nicklin and Baker, *Curr. Gene Ther.* 2(3):273-93 (2002). Other suitable adeno-associated virus (AAV) vector systems can be readily constructed using techniques well known in the art (see, e.g., U.S. Pat. Nos. 5,173,414 and 5,139,941; PCT Publication Nos. WO 92/01070 and WO 93/03769; Lebkowski et al. (1988) *Mol. Cell. Biol.* 8:3988-3996; Vincent et al. (1990) *Vaccines* 90 (Cold Spring Harbor Laboratory Press); Carter (1992) *Current Opinion in Biotechnology* 3:533-539; Muzyczka (1992) *Current Topics in Microbiol. and Immunol.* 158: 97-129; Kotin (1994) *Human Gene Therapy* 5:793-801; Shelling and Smith (1994) *Gene Therapy* 1: 165-169; and Zhou et al. (1994) *J. Exp. Med.* 179:1867-1875). Additional suitable vectors include E1B gene-attenuated replicating adenoviruses described in, e.g. Kim et al., *Cancer Gene Ther.* 9(9):725-36 (2002) and nonreplicating adenovirus vectors described in e.g., Pascual et al., *J. Immunol.* 160(9):4465-72 (1998) Exemplary vectors can be constructed as disclosed by Okayama et al. (1983) *Mol. Cell. Biol.* 3:280.

Molecular conjugate vectors, such as the adenovirus chimeric vectors described in Michael et al. (1993) *J. Biol. Chem.* 268:6866-6869 and Wagner et al. (1992) *Proc. Natl. Acad. Sci. USA* 89:6099-6103, can also be used for gene delivery according to the methods of the invention.

In one illustrative embodiment, retroviruses provide a convenient and effective platform for gene delivery systems. A selected nucleotide sequence encoding an inhibitory PVT1 nucleic acid or polypeptide can be inserted into a vector and packaged in retroviral particles using techniques known in the art. The recombinant virus can then be isolated and delivered to a subject. Suitable vectors include lentiviral vectors as described in e.g., Scherr and Eder, *Curr. Gene Ther.* 2(1):45-55 (2002). Additional illustrative retroviral systems have been described (e.g., U.S. Pat. No. 5,219,740; Miller and Rosman (1989) *BioTechniques* 7:980-990; Miller (1990) *Human Gene Therapy* 1:5-14; Scarpa et al. (1991) *Virology* 180:849-852; Burns et al. (1993) *Proc. Natl. Acad. Sci. USA* 90:8033-8037; and Boris-Lawrie and Temin (1993) *Curr. Opin. Genet. Develop.* 3:102-109.

Other known viral-based delivery systems are described in, e.g. Fisher-Hoch et al. (1989) *Proc. Natl. Acad. Sci. USA* 86:317-321; Flexner et al. (1989) *Ann. N.Y. Acad. Sci.* 569: 86-103; Flexner et al. (1990) *Vaccine* 8:17-21; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner (1988) *Biotechniques* 6:616-627; Rosenfeld et al. (1991) *Science* 252:431-434; Kolls et al. (1994) *Proc. Natl. Acad. Sci. USA* 91:215-219; Kass-Eisler et al. (1993)*Proc. Natl. Acad. Sci. USA* 90:11498-11502; Guzman et al. (1993) *Circulation* 88:2838-2848; Guzman et al. (1993) *Cir. Res.* 73:1202-1207; and Lotze and Kost, *Cancer Gene Ther.* 9(8):692-9 (2002).

Combination Therapy.

In some embodiments, the inhibitory PVT1 polypeptides and nucleic acids are administered in combination with a second therapeutic agent for treating or preventing cancer, including ovarian and breast cancer. For example, an inhibitory PVT1 siRNA of SEQ ID NO: 3 and 4 may be administered in conjunction with any of the standard treatments for ovarian cancer including, but not limited to, paclitaxel, cisplatin, carboplatin, chemotherapy, and radiation treatment.

The inhibitory PVT1 polypeptides and nucleic acids and the second therapeutic agent may be administered simultaneously or sequentially. For example, the inhibitory PVT1 polypeptides and nucleic acids may be administered first, followed by the second therapeutic agent. Alternatively, the second therapeutic agent may be administered first, followed by the inhibitory PVT1 polypeptides and nucleic acids. In some cases, the inhibitory PVT1 polypeptides and nucleic acids and the second therapeutic agent are administered in the same formulation. In other cases the inhibitory PVT1 polypeptides and nucleic acids and the second therapeutic agent are administered in different formulations. When the inhibitory PVT1 polypeptides and nucleic acids and the second therapeutic agent are administered in different formulations, their administration may be simultaneous or sequential.

In some cases, the inhibitory PVT1 polypeptides and nucleic acids can be used to target therapeutic agents to cells and tissues expressing PVT1 and other candidate genes that are related to reduced survival rate.

Kits.

The present invention further provides kits for use within any of the above diagnostic methods. Such kits typically comprise two or more components necessary for performing a diagnostic assay. Components may be compounds, reagents, containers and/or equipment. For example, one container within a kit may contain an inhibitory PVT1 polypeptides and nucleic acids. One or more additional containers may enclose elements, such as reagents or buffers, to be used in the assay. Such kits may also, or alternatively, contain a detection reagent as described above that contains a reporter group suitable for direct or indirect detection of antibody binding.

Kits can also be supplied for therapeutic uses. Thus, the subject composition of the present invention may be provided, usually in a lyophilized form, in a container. The inhibitory PVT1 polypeptides and nucleic acids described herein are included in the kits with instructions for use, and optionally with buffers, stabilizers, biocides, and inert proteins. Generally, these optional materials will be present at less than about 5% by weight, based on the amount of polypeptide or nucleic acid, and will usually be present in a total amount of at least about 0.001% by weight, based on the polypeptide or nucleic acid concentration. It may be desirable to include an inert extender or excipient to dilute the active ingredients, where the excipient may be present in from about 1 to 99% weight of the total composition. The kits may further comprise a second therapeutic agent, e.g. paclitaxel, carboplatin, a chemotherapeutic agent.

Example 1

Identifying a Candidate Gene

Marker Development.

We applied array comparative genomic hybridization (CGH) and expression profiling to localize aberrant genes in three independent sets of stage 3 and 4 serous ovarian cancers for which clinical outcome information was available. All patients were staged according to the guidelines of FIGO (Shepherd, J. H. Revised FIGO staging for gynaecological cancer. *Br J Obstet Gynaecol* 96, 889-92 (1989)). We analyzed genome copy number abnormalities using array CGH with BAC arrays (Hodgson, G. et al. Genome scanning with array CGH delineates regional alterations in mouse islet carcinomas. *Nat Genet.* 29, 459-64 (2001); Snijders, A. M. et al. Assembly of microarrays for genome-wide measurement of DNA copy number. *Nat Genet.* 29, 263-4 (2001)) in all three studies. We analyzed gene expression in two studies using the Affymetrix U133A array platform (Lancaster, J. M. et al. Gene expression patterns that characterize advanced stage serous ovarian cancers. *J Soc Gynecol Investig* 11, 51-9 (2004)). One set of 50 snap frozen serous tumors from the UAB/Duke Ovarian Cancer SPORE, designated as Study A, was comprised of 23 patients that survived>60 months and 27 that survived<36 months. A second set of 50 snap frozen serous tumors from the tumor banks of the MD Anderson Ovarian Cancer SPORE and the "Biology of Ovarian Cancer" Program Project was designated as Study B. A third study, designated study C, was comprised of 149 snap frozen serous cancers from GOG study 8004 in which patients with advanced-stage disease received primary postoperative platinum/taxane chemotherapy on GOG trials.

All tumor samples were assessed for histology by analysis of Hematoxylin and Eosine (H & E) stained sections from paraffin embedded specimens. Each frozen sample was assessed for cellularity and tumor content by analysis of H & E stained cryosections adjacent to the part taken for CGH and expression array analysis. Samples were trimmed to eliminate histologically normal tissue so that the tumor content was >70%. Genomic DNA was extracted using the Promega Wizard kit followed by phenol-chloroform extraction. RNA was extracted using standard Trizol method and quality checked by Agilent 2100 Bioanalyzer.

Array CGH.

CGH arrays for study A were comprised of 2465 BACs selected at approximately megabase intervals along the genome and were prepared by the UCSF Comprehensive Cancer Center Array Core as described in Hodgson, G. et al. Genome scanning with array CGH delineates regional alterations in mouse islet carcinomas. *Nat Genet.* 29, 459-64 (2001) and Snijders, A. M. et al. Assembly of microarrays for genome-wide measurement of DNA copy number. *Nat Genet.* 29, 263-4 (2001), which are hereby incorporated by reference. CGH arrays for Study B & C samples were comprised of 1860 P1, PAC or BAC clones. About three-quarters of the clones contained genes and STSs whose functions or genomic locations suggest possible roles in ovarian cancer development or progression. In addition, 400 overlapping BACs (contigs) across 13 Mbp at 3q26, 15 Mbp 8q24 and 30 Mbp at 20q were included since these regions are frequently aberrant in ovarian cancers and were associated with outcome in earlier studies (Lapuk, A. et al. Computational BAC clone contig assembly for comprehensive genome analysis. *Genes Chromosomes Cancer* 40, 66-71 (2004)).

Labeling of DNA samples for array CGH was accomplished generally as described previously in Hodgson, G. et al., *Nat Genet.* 29, 459-64 (2001) and Hackett, C. S. et al. Genome-wide array CGH analysis of murine neuroblastoma reveals distinct genomic aberrations which parallel those in human tumors. *Cancer Res* 63, 5266-73 (2003). Briefly, 500 ng each of cancer and normal female genomic DNA samples were labeled by random priming with CY3- and CY5-dUTP respectively; denatured, hybridized with excess unlabeled normal cot-1 DNA to CGH arrays. Following hybridization, slides were washed and imaged using a 16-bit CCD camera through CY3, CY5 and DAPI filters as described by Hodgson et al., 2001 and Snijders, A. M. et al, 2001. The resulting images were analyzed to determine CY3/CY5 ratios for each array element using custom software (Jain, A. N. et al. Fully automatic quantification of microarray image data. *Genome Res* 12, 325-32 (2002)).

Affymetrix Expression Array.

RNA samples from all 50 samples in study A and 23 samples from study B were processed for expression analysis using Affymetrix U133A array platform. RNA samples from 23 ovarian tumors in study B were processed for using the Affymetrix U133A HTA (high-throughput array) platform. The GenChip HTA system adapts standard Affymetrix chips to a 96-well microtiter plate, and runs on an automated system that is now installed at the Lawrence Berkeley National Laboratory.

Recurrent Abnormalities.

The array CGH analyses of Studies A-C showed the same remarkable inter-tumor heterogeneity as previously reported for ovarian cancers. In addition, approximately 20 regions of recurrent abnormality were noted. These are summarized in FIG. 1a for the combined studies. Regions of abnormality occurring in more than 40% of all tumors in both data sets included copy number increases at 1q22, 3q23-q27, 7q36, 8q24, 12p13, and 20q13 and copy number decreases at 4p14, 4q22-q35, 6q22-p26, 7p15, 8p23-p21, 9q31-q33, 13q12-q34, 14q32, 15q14, 16 p12-q24, 17p13-q21, 18q21-q33 and 22q11-q13.

Associations with Copy Number.

We used array CGH data from studies A and B to develop strategies to stratify patients according to their survival duration. To accomplish this, study B data (62 from Stage III or IV patients with follow up information available) was treated as a training set and Study A data (69 samples with 50 from Stage III or IV patients (23 long and 27 short survivors) then was treated as test data. The classifier optimization procedure used the Study B dataset to identify events that stratified between patients with short (i.e. <36 months) and long survival (i.e. >42 Months). The resulting classifier was tested in Study A.

We first assessed associations between the frequency of genomic gains and losses (i.e. log 2 ratios>0.3 or <−0.3). These associations did not reveal statistically significant associations. We then tested associations of survival duration with high level amplification (log 2 ratio>0.9) since high level amplification has been associated with adverse outcome in other studies.

General Amplification Classifier.

Figure 2:
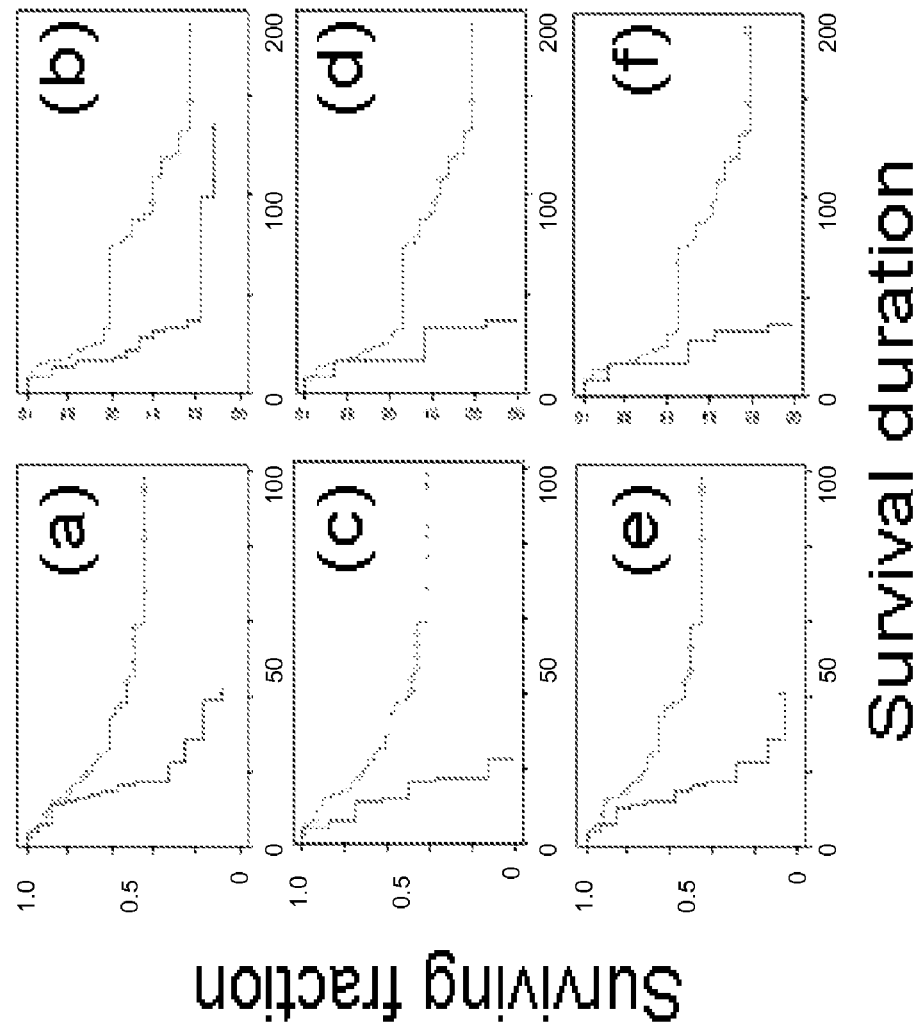
FIG. 2 shows 6 graphs of Kaplan-Meyer survival curves showing the fraction of patients with serous ovarian cancer surviving with time (months) after surgery plus platinum/taxol therapy. Panels a, b show stratification according the presence of high level amp. of >0.9% of the genome (red) vs. amp. of <0.9% of the genome (green) in studies B and A respectively. Panels c, d show stratification according to the presence of high level amplification at 8q24.13 (red) vs. no amplification in studies B and A respectively. Panels e, f show stratification according to the presence of high level amplification (amp.) at 8q24.13 11q13.3 and/or 20q11.21 (red) vs. no amplification (amp.) in studies B and A respectively.

One successful classifier was based on the prevalence of high-level amplification anywhere in the genome. We accomplished this by assigning samples to high risk status if the proportion of genome amplified exceeded a certain cut-off and to low risk status otherwise. We determined the optimal value of the cutoff using study B samples and assessed its stability by performing a leave-one-out cross-validation procedure. To do this, we repeatedly left one sample at a time out, calculated the cut-off providing the lowest p-value for prediction of the survival status on the remaining samples and applied that cut-off to assign label to the left-out sample. The resulting cut-off had mean and median of 0.0086 and log-rank p value=0.0024. The stratification achieved using this approach is illustrated in FIG. 2a.

We tested this procedure on the Study A data. We established correspondence between the clones used in array CGH in the study B the classifier and the clones in the study A dataset by mapping each of the clones in the classifier to its closest in genomic distance counterpart in the study A dataset. The mapping was "many to one" in the sense that the same clone on the RTK array could have been the closest to several clones in the classifier. We kept all the resulting clones, i.e. the test dataset used the same number of clones as were used in the classifier.

We applied the Study B classifier to the resulting subset of data by computing proportion of clones amplified for each sample among the clones used in the classifier and assigning sample to the short survivor group if this proportion was greater or equal than 0.0086. The survival times in two predicted groups were compared using log-rank test resulting in 3-sided p-value of 0.022. The stratification achieved among study A patients is illustrated in FIG. 2f.

Specific Locus Classifier.

We next tested associations of short survival duration with the presence of high level amplification at any of three specific loci. We limited the search to only three loci in order to guide development of a three-color FISH-based assay that could be readily applied to paraffin embedded samples. Again, Study B was used as the training set. Leave-one-out cross validation in Study B analyses showed strong associations between high level amplification at 8q24.13 (126688 Kbp), 1q13.3 (69396 Kbp) and/or 20q 1.21 (31218 Kbp) and short survival duration for platinum/taxol treated patients (p=5.6e-05; see FIG. 2c). This stratification algorithm was validated in study A (p=0.012, FIG. 2d). The specificity for detection of patients surviving less than 24 months in study A was >95% (specificity=fraction of patients predicted to survive<24 months that actually survived<24 months) with a sensitivity of >60% (=number of patients predicted to survive<24 months/number that actually survived<24 months). Thus, the assay is well suited to detection of a subpopulation of patients with short survival duration.

The association between 8q24 amplification and short survival duration was the strongest predictor as illustrated in FIGS. 2e,f. Amplification at 8q24.13 alone stratifies patients according to survival (p=41.5e-05 in the Study B training set and 0.015 in the study A test set). The only disadvantage of using a single locus test is that a small fraction of poorly performing patients will be missed.

Target Gene Identification.

Our goal has been to identify genes in regions of recurrent abnormality that are deregulated as a result of amplification and that contribute to the aggressive phenotype associated with amplification. The following genes were considered to be priority therapeutic targets: MYC and PVT1 at 8q24; CCND1, PPFIA1 and EMS1 at 11q13 and PTK6, EEF1A2 and ZNF217 at 20q13.

Copy Number vs. Gene Expression Associations.

We measured expression profiles for all tumors in studies A and B for which sufficient material was available. These data were used to identify genes in regions of recurrent genome copy number abnormality that appeared to be differentially expressed as a result of the genomic changes leading to copy number abnormalities and that might be attacked therapeutically. Two different algorithms were used to identify the deregulated genes.

In one approach, we searched for genes more-or-less linearly deregulated by changes gene dosage. These genes were identified by calculating Pearson correlation coefficients between copy number as measured by array CGH and expression level as measured using Affymetrix expression profiling. Correlation coefficients were measured for all genes on the Affymetrix arrays that mapped within 0.5 Mbp of a BAC on the CGH arrays. This algorithm assumes that genome aberrations usually span several megabasepairs so that a measure of copy number within 0.5 Mbp of an expressed genes is a good approximation of the copy number of that gene.

Figure 3:
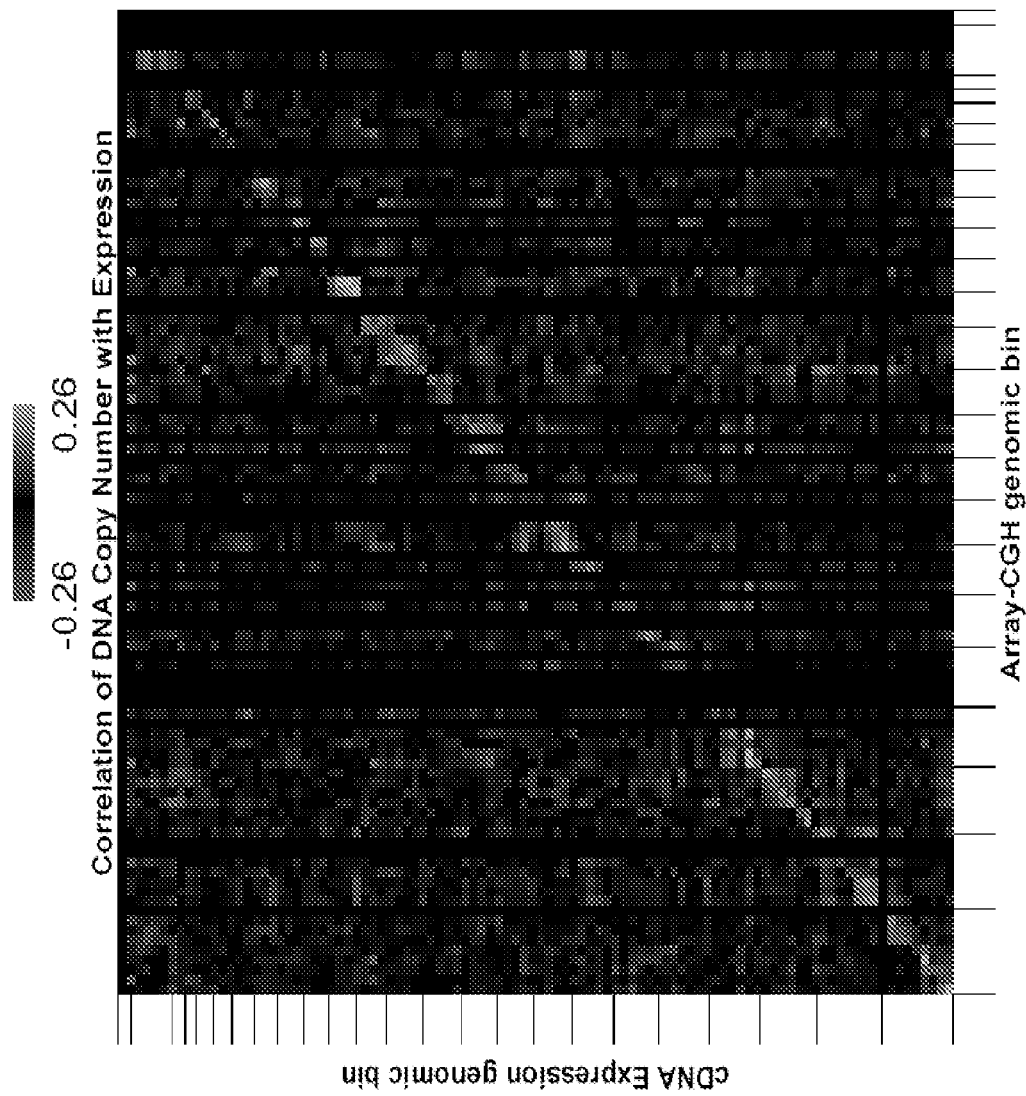
FIG. 3 is a screen shot of array CGH output. Data are organized according to genome location. Green indicates a positive correlation and red indicates a negative correlation. Scale is shown at the top of the figure.

Significant correlations between copy number and expression level were identified for >1000 genes distributed across the entire genome. These correlations are illustrated in FIG. 3. Correlations with copy number for genes in regions of high level amplification associated with short survival duration (i.e. 8q24.13, 1q13.3 and 20q11-13) are listed in Table 1.

A second approach was based on the assumption that the mechanisms of gene deregulation vary between tumors and include copy number abnormalities, structural changes altering regulatory regions, mutations and/or epigenetic mechanisms. In this approach, we searched for genes whose expression levels were consistently increased in tumors with increased copy number and also sometimes were increased relative to normal in tumors showing no copy number abnormalities and genes whose expression levels were consistently decreased in regions of decreased copy number and sometimes decreased in tumors showing no copy number abnormalities. We limited these analyses to regions that were recurrently aberrant in more than 40% of tumors under the assumption that the presence of recurrent genomic aberrations is strong evidence for the presence of genes that are actively selected for or against during tumor progression. Several genes are found to be deregulated relative to normal in these regions. Association strengths for genes in regions of high level amplification associated with short survival duration are also listed in Table 1.

Assessment of Gene Function.

The functions of differentially expressed genes in regions of high level amplification or frequent copy number increase are being investigated (data not shown). To date, these studies have identified several genes that appear to be important in the pathophysiology of ovarian cancers based on our findings that modulation of the expression levels of these genes in ovarian cancer cell lines, xenografts and ovarian surface epithelial cells alters cancer linked phenotypes such as proliferation rate, motility and apoptosis. These including RAB25, EVI1, PIK3CA, PKCi, PVT1, MYC, CCND1, EMS1, PPFIA1, PTK6 and ZNF217. All are potential therapeutic targets and will be considered. However, PVT1, MYC, CCND1, EMS1, PPFIA1, PTK6 and ZNF217 are of special interest here because they are in regions of amplification associated with reduced survival duration.

8q24. This amplicon encodes MYC and the putative MYC activator, PVT1, which has been described in part in Siwarski, D. et al. Structure and expression of the c-Myc/Pvt 1 megagene locus. *Curr Top Microbiol Immunol* 224, 67-72 (1997). The PVT1/MYC amplicon is recurrently increased in copy number in carcinomas of the ovary (50%), respiratory tract (10%), breast (10-40%), bladder (~10%), prostate (~15%) as well as in eye melanoma (100%) and medulloblastoma (~10%) (see URL:<http://www.helsinki.fi/cmg/cgh_data.html>). In addition, this region is involved in the translocation partner of the t(2; 8) translocation in Burkitt's lymphoma. See Zeidler, R. et al. Breakpoints of Burkitt's lymphoma t(8; 22) translocations map within a distance of 300 kb downstream of MYC. *Genes Chromosomes Cancer* 9, 282-7 (1994). It is often assumed that MYC is the target of these aberrations. However, PVT1 is 57-250 kb 3' of MYC and is closer to the t(2; 8) translocation breakpoint than MYC. Moreover, PVT1 but not MYC is highly amplified double minute chromosomes from acute myeloid leukemia and myelodysplastic syndrome cases (Storlazzi, C. T. et al. Identification of a commonly amplified 4.3 Mb region with overexpression of C8FW, but not MYC in MYC-containing double minutes in myeloid malignancies. *Hum Mol Genet.* 13, 1479-85 (2004)). In mice, PVT1 is a site of recurrent tumorigenic viral integration (Santos, J. & Pellicer, A. Novel RFLPs at protooncogene and cancer-related gene loci on mouse chromosomes. *Cytogenet Cell Genet.* 62, 217-9 (1993)) and transgenic mice carrying a Pvt1/Ig Ck fusion gene develop tumors of B cell origin (Siwarski, D. et al., *Curr Top Microbiol Immunol* 224, 67-72 (1997)).

Initial priority in the Examples described herein have been given to PVT1 since it maps to the region of amplification at 8q24 that is most strongly associated with reduced survival duration in platinum/taxane treated patients. Little is known for genes within this region except for MYC which is a well-known oncogene in many types of malignancies including ovarian cancer. PVT1 transcription unit is located 57 kilobase pair downstream of c-myc. Previous studies have shown that PVT1 was involved in translocations and genome amplifications that were specific for malignant cells in Burkitt's lymphoma and colon cancer, respectively. Using quantitative real-time PCR, we have found the transcription levels of PVT1 was highly correlated with the DNA copy number alterations in ovarian cell lines (Pearson's correlation coefficient=0.74). Moreover, high level amplification and/or over expression of PVT1 are significantly associated with reduced survival duration in ovarian tumors. Treatment of 2 cell lines that over express PVT1 with siRNAs that reduce PVT1 transcription inhibit cell proliferation by blocking cell in the G1-phase of the cell cycle and by inducing cell death. Treatment of cell lines that do not amplify or over express PVT1 with the PVT1 siRNA do not inhibit growth or induce cell death. These examples show that molecular procedures that detect PVT1 and other gene amplification or over expression in serous ovarian cancers will identify cancer patients that will not respond well to conventional platinum plus taxol based therapies. They also show that these patients will respond to therapies that inhibit gene expression, e.g. PVT1 gene expression.

Although both MYC and PVT1 are in the region of high level amplification at 8q24 that is most strongly associated with reduced survival duration in breast and ovarian cancer, only the over expression of PVT1 is significantly associated with reduced survival duration in our Affymetrix analyses of expression in ovarian cancer (p=0.018) and in published gene expression studies (p=0.06). Moreover, siRNA inhibition of PVT1 in ovarian cancer cell lines in which it is amplified and over expressed, blocks cells in the G1 phase of the cell cycle and induces apoptosis. siRNA inhibition of MYC, on the other hand, blocks cells in the G1-phase of the cell cycle but does not induce apoptosis.

11q13.

Assessment of genes in this region of amplification has just been initiated in P01 CA64602. To date, we have shown that inhibiting both EMS1 and PPF1A1 inhibit cell cycle traverse in cells in which 11q13 is amplified. EMS1 is the human homolog of cortactin, an actin-binding protein involved in the restructuring of the cortical actin cytoskeleton that may act to modulate cellular adhesion. PPF1A1 encodes a member of the LAR protein-tyrosine phosphatase-interacting protein (liprin) family. Liprins interact with members of LAR family of transmembrane protein tyrosine phosphatases, which are known to be important for axon guidance and mammary gland development. PPF1A1 binds to the intracellular membrane-distal phosphatase domain of tyrosine phosphatase LAR, and appears to localize LAR to cell focal adhesions. This interaction may regulate the disassembly of focal adhesion and thus help orchestrate cell-matrix interactions. Although neither PPF1A1 nor EMS1 appear in Table 1, siRNA inhibitors of these genes produce G1-phase arrests much like that observed following siRNA inhibition of MYC (data not shown). However, inhibition of these genes does not induce apoptosis. siRNA inhibitions of other genes in the list will be performed before settling on candidate therapeutic targets in this region.

20q11-q13.

Three genes from chromosome 20q11-q13 have been assessed as possible therapeutic targets; ZNF217, PTK6 and PFDN4. Expression of each of these genes is associated with reduced survival duration.

ZNF217 is a Krupple-like zinc finger transcription factor. We originally cloned this gene from a region of recurrent high level amplification in breast cancers[30] where it is increased in copy number in 20-30% of primary breast tumors and is highly amplified in 5-10%. High-level amplification is associated with a 50% decrease in disease-free survival in breast cancer, and laboratory data indicate that ZNF217 over expression suppresses cell death induced by genome DNA damage (Nonet, G. H. et al. The ZNF217 gene amplified in breast cancers promotes immortalization of human mammary epithelial cells. *Cancer Res* 61, 1250-4 (2001)) and contributes to transition through telomere crisis. In addition, increased expression of ZNF217 is associated with reduced survival duration in ovarian cancer (study B; p=0.04). We have shown in P01 CA64602 that transfection of ZNF217 into ovarian surface epithelial (OSE) cells stimulates their growth in the presence of EGF/HC (although transfection confers a disadvantage in the absence of EGF). SV40 immortalized IOSE cells become anchorage independent when transfected with ZNF217. ZNF217 is an attractive therapeutic target because it appears to play a critical role in the development of early cancers and is also important in more advanced disease. Importantly, array CGH analyses of ZNF217 immortalized IOSE cultures show gains of 1q22, gain of 3q26, 8q24, 11q13 and 20q11-q13; i.e., all of the recurrent amplicons under study in the project. Thus, a byproduct of the ZNF217 functional studies is a useful in vitro model that can be used to monitor the effects of amplicon gene inhibitors during cell immortalization.

PTK6 is increased in copy number in ~40% of serous ovarian cancers and elevated expression of PTK6 is associated with reduced survival duration (p=0.06 in study B). PTK6 is a protein tyrosine kinase expressed in ~10% of normal ovarian surface epithelium but is highly expressed in 70% of high-grade serous carcinomas. PTK6 is localized primarily to the cytoplasm of ovarian cancer cells but some tumors show nuclear staining as well. Expression of wt PTK6 in ovarian cancer cell lines increases proliferation by 15-20% while treatment with siRNAs slows growth by 10-15%. Taken together, these data suggest that over expression of PTK6 does influence the pathophysiology of ovarian cancer so inhibitors may be useful in treatment of ovarian cancer. The attractiveness of PTK6 as a therapeutic target is increased because the general understanding of kinase structure and function facilitates development of new inhibitors. However, responses seen to date are not sufficiently strong to warrant designating PTK6 as a high priority therapeutic target.

PFDN4 is a heterohexameric chaperone protein which assists in the correct folding of other proteins. It consists of two PFD-alpha type and four PFD-beta type subunits. It binds specifically to cytosolic chaperonin and transfers target proteins. Prefoldin may function by selectively targeting nascent actin and tubulin chains pending their transfer to cytosolic chaperonin for final folding and/or assembly. It promotes folding in an environment in which there are many competing pathways for normative proteins. PFDN4 over expression is associated with reduced survival duration in serous ovarian cancers (p=0.06). In addition, amplification of the region synthetic to human chromosome 20q13 occurs in the RIP1-Tag2 mouse model of multistage carcinogenesis in which the rat insulin gene II promoter targets expression of the SV40 T antigens to the insulin-producing pancreatic P cells. Collaborative studies with the Hanahan laboratory at UCSF have shown that PFDN4 is expressed and significantly upregulated in tumors containing the amplification and that transfection of PFDN4 into cultured islet tumor cells that lack were not amplified enhanced their tumorigenicity upon transplantation into immunodeficient Rag 1-null mice. Both the frequency of tumor establishment and the rate of tumor growth were increased in the PFDN4-transfected cell lines.

Thus after assessment of the priority targets, the following genes are considered to be high priority therapeutic targets: for 8q, MYC and PVT1; for 11q, CCND1; for 20q13.1, HE4 and WHDC2; for 20q13.2, ZNF217; and for 20q13.3, PTK6.

Example 2

Developing a Tri-Locus Assay

One goal is to develop a robust tri-locus assay to stratify patient outcome. A FISH assay is ideally suited as a simple, easy and robust assay. To do so we need to validate the tri-locus classifier identified in the array CGH dataset in Example 1 with FISH probes. Development of a robust tri-locus FISH assay will require optimization of the probe, hybridization conditions and scoring procedures.

Probes.

One key to development of a robust assay that can be applied to paraffin embedded samples is development of probes that span minimally several hundred kilobases centered on each region of interest. We will accomplish this by selecting FISH probes comprised of contiguous BACs covering each locus.

We have already applied this approach to develop probes for early ovarian cancer detection. FIG. 4, for example shows FISH with probes to regions of recurrent copy number increase at 3q26 and 8q24 Probe DNA from the EVl1 locus was labeled with a red fluorescing dye and probe DNA from the MYC locus was labeled with a green fluorescing dye. Comparison of the two images of 2-color FISH results showing normal (2 copies each, left image) and aberrant (increased copy numbers, right image), it is apparent that there is aberrant and increased copy number of both genes. This figure demonstrates that these probes can be used for early detection and thus may be used for a tri-locus assay to validate the Array cGH data in Example 1.

We have determined 500 Kbp to 2 Mbp "contig" spanning regions of high level amplification at 8q24.13 (877223 bp), 11q13.3 (1311424 bp), 20q13.1 (1980969 bp), 20q13.2 (1903354 bp), and/or 20q13.3 (1577742 bp) that are most strongly associated with reduced survival duration, avoiding regions of the genome that harbor low level repeats that may not be fully blocked during hybridization content thereby giving false positive hybridization signals. These contigs are identified in Tables 2-6.

Tissue Microarrays.

Figure 5:
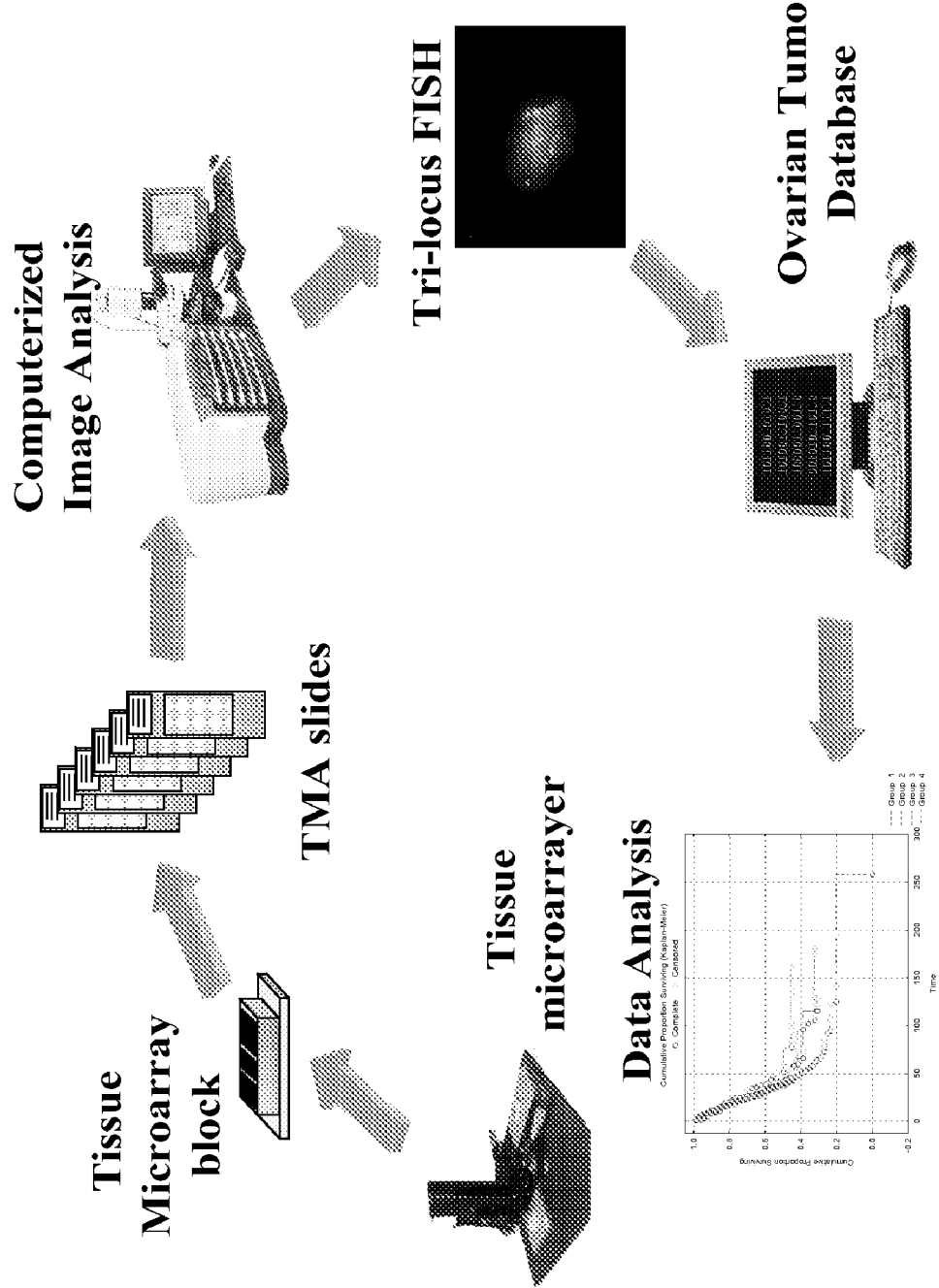
FIG. 5 is a schematic showing the experimental and data flow. Tissue microarrays will be prepared in the Tissue Core according to established procedures. Sections will be managed using a computerized image analysis system. Information on individual samples in the microarrays will be merged with information in the Tumor Database and analyzed to determine associations with outcome.

Tissue microarray will be prepared in the Tissue Core and analyzed as illustrated in FIG. 5. Briefly, 700 µm cores will be taken from each paraffin embedded sample and transferred to a recipient paraffin block. Once complete, three 5 µm sections will be cut from each sample and prepared for hybridization. Sections immediately adjacent to and above and below those taken for FISH will be H&E stained and examined histologically for tumor content as illustrated in FIG. 5. This process is already well established in the Tissue Core.

Conditions using paraffin embedded normal surface epithelium so that all probes hybridize with approximately the same efficiency will be employed. We will start these studies using hybridization conditions that we have found to be effective in other analyses of paraffin embedded tissue, and described in Chin, K. et al. In situ analyses of genome instability in breast cancer. *Nat Genet.* 36, 984-8 (2004). Briefly, FISH will be carried out using 500 ng each of a Spectrum Green labeled probe for 8q24.1, a Spectrum Orange labeled probe for 11q13.3, and a Spectrum Aqua labeled probe for 20q13.1. The probes will be added to 150 µg of salmon sperm DNA and 20 µg of Cot-1 DNA, denatured and hybridized to 5 µm thick sections cut from tissue microarrays that have been deparaffinized, treated in 1M sodium thiocyanate at 80° C. for 8 min. and denatured in 50% formamide at 73° C. for 5 min. Sections will then washed and mounted using anti-fade buffer.

Figure 6:
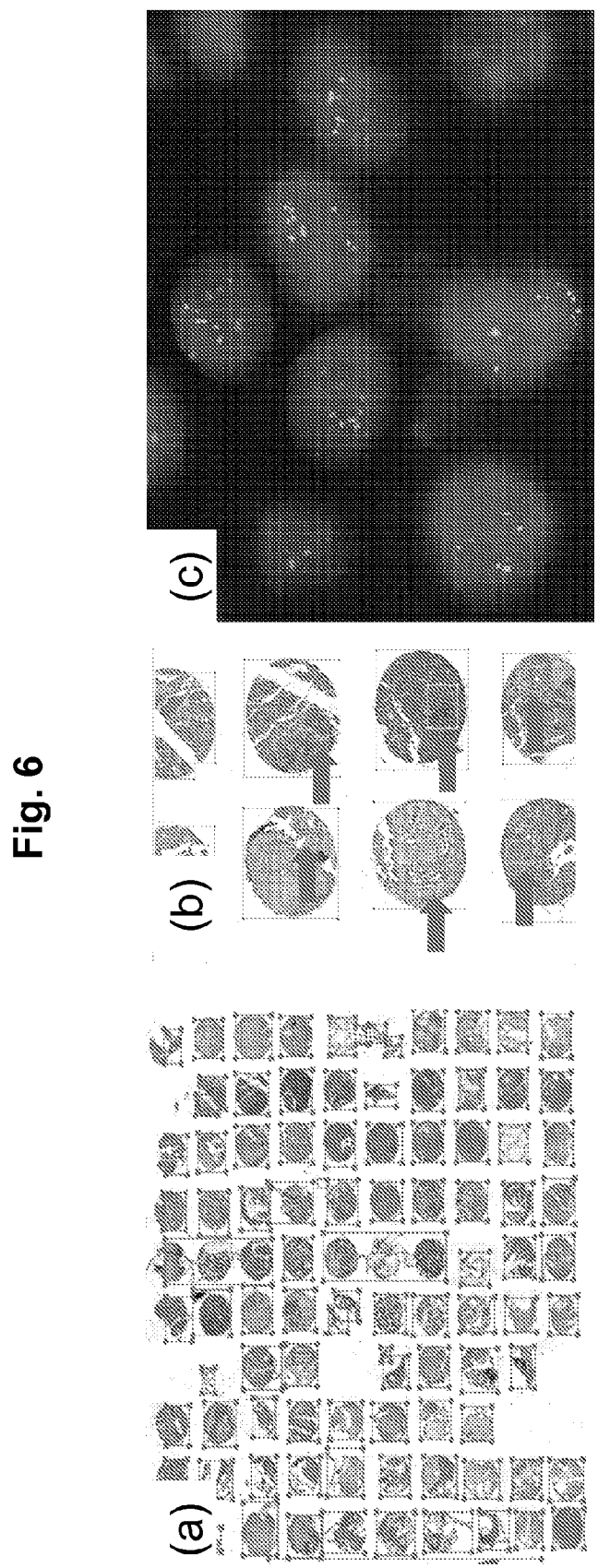
FIG. 6 shows how tissue microarrays are prepared in the Tissue Core from >100 ovarian cancers. Panel a shows a computer rendering of an image acquired for an H&E stained. Panel b shows enlarged images with arrows indicating regions of high tumor content. Panel c shows tricolor FISH analysis of copy number in a paraffin section. These analyses assessed EMSY (green), cyclin D1 (red) and CEP 11 (blue). Amplification of EMSY is apparent.

Optimized hybridization conditions will be applied to tissue microarrays prepared in the Tissue Core from 250 paraffin embedded samples already analyzed using array CGH (see Results above). These procedures are already well established so we anticipate little difficulty with either tissue microarray preparation or multi-color FISH. FIG. 5, for example, shows a tissue micro array carrying 700 µm diameter cores from >100 ovarian tumors and tricolor detection of copy number at CCND1, the chromosome 11 centromere and EMSY. Referring to FIG. 6, tissue microarrays are prepared according to established procedures. FIG. 6a shows a computer rendering of an image acquired for an H&E stained microarray section using an Ariol SL50 image analyzer (San Jose, Calif.) comprised of a Nikon Eclipse TE2000-U microscope connected to a CCD camera (Coolsnap CFPhotometrics, Roper Scientific) and MetaVue 6.1 image analysis software (Meta Imaging Series 6.1, Universal Imaging Corporation). FIG. 6b shows enlarged images with arrows indicating regions of high tumor content. FIG. 6c shows tricolor FISH analysis of copy number in a paraffin section. These analyses assessed EMSY (green), cyclin D1 (red) and CEP 11 (blue). Amplification of EMSY is apparent, thus a tri-locus test can be developed and optimized.

Results.

Probes were developed for the 8q24, 11q13 and 20q11-q13 regions using the contigs identified in Tables 2-6. A tissue microarray containing 10 cell lines and 35 ovarian tumors (25 of them used in array CGH study) was used to test the tri-locus FISH probes. The changes in copy number detected in FISH assay correlated well with the changes detected by array CGH, therefore validate the efficacy of the assay.

Example 3

Tri-Locus FISH Assay Used to Stratify Patient Outcome

The tri-locus FISH assay developed in Example 2 will be used to stratify patients according to outcome in three retrospective analyses: (1) 70 samples from patients treated with platinum/taxol at MDACC on GOG protocol 0152; (2) 110 samples from patients treated at MDACC on GOG protocol 0182; (3) 1300 samples from patients treated with carboplatin under protocol SCOTRCO4.

Approaches. These studies will explore the robustness of the assay for amplification developed in Example 1 against changes in therapy. Study 1.b.i. is a direct, small-scale validation of the assay developed in Example 2. Patients in this study were treated on platinum/taxol based protocols similar to those used in the studies on which the assay is based. Patients in study 1.b.ii. were treated with a variety of therapeutic agents including carboplatin/pacitaxel. Successful stratification of patients in this cohort will indicate that the stratification power comes from amplification driven resistance to any DNA damaging agent and will support the general utility of the stratification assay. Patients in study 1.b.iii. were treated with carboplatin alone. Application of the amplification assay to samples from this study will allow us to test the hypothesis that the assay predicts outcome upon treatment with only a platinum compound.

Methods.

Separate tissue microarrays will be prepared for each of the three studies and hybridized and scored as determined in Example 1.

1.b.i. GOG #0152.

Seventy blocks are available for GOG Protocol 152. GOG #0152 was a phase III randomized study of cisplatin and taxol vs. cisplatin and paclitaxel in patients with suboptimal stage III epithelial ovarian carcinoma.

1.b.ii. GOG #0182.

One hundred ten paraffin blocks are available from GOG Protocol 0182. This is a five arm trial comparing gemcitabine, topotecan, liposomal doxorubicin, and prolonged oral etoposide against carboplatin-paclitaxel. Preclinical models have suggested an advantage for combinations of these agents with platinum, which has been attributed to inhibition of DNA synthetic pathways involved in the repair of platinum-DNA adducts. However, efforts to develop multidrug combinations with platinum and paclitaxel have encountered substantial bone marrow toxicity, prompting exploration of alternative schedules and sequences of drug administration. The goal of these phase I pilot studies in previously untreated patients was to define combinations that would be suitable for group-wide phase III trials.

1.b.iii. SCOTROC4.

This is a phase III, randomized trial conducted within the Scottish Gynecological Cancer Trials Group (SGCTG) that aims to determine if intra-patient dose-escalation of carboplatin improves outcome over carboplatin flat dosing. Approximately 1300 paraffin embedded samples will be collected during the course of this four year study (Recruitment into SCOTROC4 began in March 2004 and should be completed by March, 2008). The primary endpoint of the trial is progression free survival. Other endpoints include overall survival, quality of life, toxicity and response rate. For inclusion, patients must be 18 or over, with histologically confirmed epithelial ovarian carcinoma or primary fallopian tube carcinoma (FIGO stages Ic-IV). Patients will be excluded on the following criteria: ECOG performance status≧3; prior treatment with chemotherapy or radiotherapy; inadequate bone marrow/renal/liver function; history of previous malignancy within the previous 5 years; pregnant or lactating women; or symptomatic peripheral neuropathy. Patients will be allocated centrally to treatments and will receive 6 cycles of carboplatin monotherapy, either flat dosed AUC 6 or escalating from AUC 6 increasing by 10-20% per cycle assuming adequate marrow function. Randomization will take place within 8 weeks of surgery.

DNA from these tri-locus probes will be produced and labeled by Vysis, Inc with Spectrum Orange, Spectrum Green and Spectrum Aqua to produce a three color hybridization probe for detection of amplification at any or all of our test loci amplification Probe production and labeling will be accomplished using Good Manufacturing Practices (GMP) at Vysis so that the analyses of the associations with outcome conducted under the auspices of this SPORE will be useful in obtaining FDA approval for clinical use of these markers.

We also will generate a 500 Kbp reference probe at 21q21.3. Array CGH analyses show this region to the least frequently aberrant locus in serous ovarian cancers (present at abnormal copy number in <5% of all cancers). This probe will be labeled with Spectrum Gold so it can serve as a reference for all three test loci.

Tissue Microarrays, Hybridization and Scoring.

Separate tissue microarrays will be prepared for each of the three studies as described in Example 2. Arrays for studies 1.b.i and 1.b.ii will be prepared and sectioned at MD Anderson in the Tissue Core. Arrays for study 1.b.iii will be prepared and sectioned in Scotland. All sections will be evaluated in the Tissue Core for adequacy and tumor content and then shipped to LBNL for FISH analysis.

Scoring.

Scoring criteria will be developed by visually counting the numbers of Green, Orange, Aqua and tri-color signals for 250 cells selected randomly throughout each 700 µm core in each of the cores in three sections cut from the 250 sample tissue microarray. Three separate analysts will score each tissue microarray section. The identities of the samples in the array will not be known by the analysts. In addition, the analysts will determine the frequencies of cells with four or more closely spaced hybridization signals (an indication of focal, high level amplification (Walker-Daniels, J., Hess, A. R., Hendrix, M. J. & Kinch, M. S. Differential regulation of EphA2 in normal and malignant cells. *Am J Pathol* 162, 1037-42 (2003)) in each sample. These measurements will then be used to select scoring criteria that identify patients that survive less than 24 months with specificity>95% and sensitivity>60%. These data also will be used to determine the extent to which sample classification is scorer dependent, whether fewer than 250 cells can be scored without losing specificity and criteria for assessment of sample adequacy.

Standardized scoring criteria will be applied unchanged during analysis of all sections. One experienced analyst will score all sections. The identities of the samples in the arrays from the three studies will not be known by the analyst. Scores will be entered into the Tumor Database and combined with clinical outcome to determine the sensitivity and specificity with which patients surviving<24 months can be predicted. Importantly, the SCOTROC4 consortium will apply large scale molecular profiling strategies to assess gene expression, DNA copy number and methylation status in SCOTROC4 patients included in study 1.b.iii. Comparison of our results to theirs will allow us to compare the predictive power of the tri-locus amplification assay to independent molecular profiling predictors.

If the specificity>95% and sensitivity>60% for detecting patients surviving<24 months are not achieved in Example 1, we will refine the scoring criteria in order to achieve the desired levels. We will also consider development of other predictive assays as described herein. If the specificity and sensitivity thresholds are not achieved in Example 2, 1.b.ii and/or 1.b.iii, we may limit the assay to prediction of short survival duration only to patients receiving platinum/taxane compounds.

Example 4

Independent Validation of the Tri-Locus FISH Assay

Independent validation of performance will apply the assay to for validation in a retrospective analysis of paraffin embedded samples from 700 moderate and high risk ovarian cancers (60% five year survival), the majority treated with platinum based therapy and 500 high risk cancers treated with cisplatinum and taxane.

Approach.

The British Columbia Cancer Agency (BCCA) is the sole provider of cancer care in the province of British Columbia (BC). This population based cancer care ensures that all BC women with ovarian cancer are treated with standardized protocols and that clinical follow-up data is readily available. Both factors make population based studies of prognostic and predictive cancer biomarkers possible.

Since 1985 the BCCA gynecologic oncology tumor group has stratified ovarian cancer patients into four prognostic risk groups: low, moderate, high and extreme (Swenerton, K. D. et al. Ovarian carcinoma: a multivariate analysis of prognostic factors. *Obstet Gynecol* 65, 264-70 (1985)). This risk assessment includes FIGO stage, tumor grade and extent of residual disease and has been used effectively to triage patients into different treatment groups (Hoskins, P. J. et al. Platinum plus cyclophosphamide plus radiotherapy is superior to platinum alone in 'high-risk' epithelial ovarian cancer (residual negative and either stage I or II, grade 3, or stage III, any grade). *Int J Gynecol Cancer* 5, 134-142 (1995); Hoskins, P. J. et al. 'Moderate-risk' ovarian cancer (stage I, grade 2; stage II, grade 1 or 2) treated with cisplatin chemotherapy (single agent or combination) and pelvi-abdominal irradiation. *Int J Gynecol Cancer* 4, 272-278 (1994)). Low risk patients are stage I grade 1 without cytological, microscopic or macroscopic evidence of residual disease; such patients have not been offered chemotherapy. Moderate risk patients include all residual negative, stage I and II patients with two exceptions: stage Ia or b, grade 1 cancers and grade 3 cancers. High risk patients have no visible residual tumor following primary surgery and either stage I, grade 3; stage II, grade 3; or stage III, any grade. Extreme risk cancers include any stage IV tumors and any with macroscopic residual disease. A detailed chart review of the 3500 patients treated for ovarian at the BCCA from 1987-2000 identified 291 moderate risk, 535 high risk and 1662 extreme risk patients with the remainder being low risk, borderline tumors or metastatic lesions. The 10 year relapse free survival for the moderate risk and high risk groups are 75% and 55%, respectively, making these cohorts ideal for the assessment of prognostic factors. All moderate, high and extreme risk patients have treated with platinum based therapy and in combination with a taxane since 1999 for the moderate and high risk and 1995 for the extreme risk patients.

Methods.

The tissue blocks from 700 of the moderate/high risk patients from the BCCA 1987-2000 cohort have been collected, subjected to pathology review and will be arrayed into 0.6 mm duplicate core tissue microarrays (TMA's). To increase the numbers of taxane treated moderate/high risk patients, the TMA cohort will be extended to include an additional 200 cases diagnosed between 2000 and 2003. Also an array of 500 extreme risk patients treated with platinum/taxane combination chemotherapy will be available for study. The TMA construction and biomarkers studies will be performed by a laboratory with extensive experience in TMA construction, the assessment of novel biomarkers, the development and application of novel FISH based assays to TMA's, and TMA data analysis. Prior to applying the multicolor probe set to the TMA's the BC laboratory will perform hybridize and score 100 of the ovarian cancers used in Example 2. If comparison of the results from all three probes produces a kappa statistic of >0.8 (excellent agreement) then analysis of the BC TMA's will proceed. If less than excellent agreement of results is achieved, this will trigger a careful reexamination of all protocols and case by case audit of results until the cause of the disparities are identified and rectified. The tri-color FISH assay will be applied to the TMA's using the protocols developed in Example 2 and scored using a TMA enabled automated fluorescent spot counter (Metafer, Metasystems, Germany). The raw scores obtained for each probe from 100 non-overlapping nuclei and an amplification ratio obtained against a chromosome 21q21.3 control probe will be directly entered into sector maps rather than spread sheets to avoid data frame shifts. The data will then be de-convoluted into an Excel spreadsheet prior to statistical analysis.

It may be that the tri-locus amplification test does not identify patients with survival duration<24 months upon treatment with carboplatin alone. This will indicate that amplification in short survival duration in platinum/taxane treated patients causes resistance to taxanes but not platinum compounds OR, more likely, that the assay was not properly transferred. The former possibility will be tested mechanistically. The latter possibility will be tested by rescoring the hybridized sections visually and, if needed, transferring fresh sections from study 1.b.iii and rerunning the entire assay.

This study will assess correlations between abnormalities and clinical outcome in GOG Protocol 8004; a pilot study to correlate DNA sequence copy number abnormalities with outcome in patients with advanced epithelial ovarian cancer.

Subject Population.

The subjects for this study will be chosen from patients who participated in GOG #136 (mainly via GOG #0158 and GOG #0152).

Example 5

Tri-Locus Quantitative PCR Assay

In another example, where there is a possibility that scoring criteria cannot be developed that will allow identification of patients surviving less than 24 months with specificity>95% and sensitivity>60%, we will search for scoring criteria that will maintain specificity at the expense of sensitivity. In this case, we will explore the extent to which quantitative PCR strategies can be used to assess over expression of PVT1, CCDN1, and ZNF217 and other genes in regions of high level amplification, specifically at 8q24.1, 11q13.3 and 20q13.1. This approach has the advantage that it can add to commercial prognostic tests already being deployed but the disadvantage of being more difficult to deploy widely. We also will collaborate with Affymetrix to explore the extent to which array CGH to 100K SNP arrays on the Affymetrix High Throughput Analysis system can be developed into a CLIA approved assay. The HTA system performs hybridization in 96-well format to 96 separate gene chips attached to an array of posts (so-call "peg-arrays"). A fully equipped Caliper liquid handling system, a thermal cycler, two incubators and a few other peripheral instruments are integrated to carry out sample prep steps according to standard Affymetrix protocols including DNA digestion, adapter oligonucleotide ligation. This system is now in operation at LBNL.

Quantitative PCR was performed essentially as in Elson, D. A., Thurston, G., Huang, L. E., Ginzinger, D. G., McDonald, D. M., Johnson, R. S., and Arbeit, J. M. (2001). Induction of hypervascularity without leakage or inflammation in transgenic mice overexpressing hypoxia-inducible factor-1alpha. Genes Dev 15, 2520-2532, herein incorporated by reference. In brief, 'no reverse transcriptase' controls were performed on all samples to confirm that genomic DNA was not present. 300 ng RNA was reverse transcribed into cDNA with an iScript kit (Bio-Rad, Hercules Calif.) in a 20 µl volume according to manufacturers specifications.

Quantitative-PCR analysis was performed on an ABI Prism 7900 or 7700 sequence detection system (Applied Biosystems, Foster City, Calif.). Quantitative detection of specific nucleotide sequences was based on the fluorogenic 5' nuclease assay, as summarized in Ginzinger, D. G. (2002). Gene quantification using real-time quantitative PCR: an emerging technology hits the mainstream. Exp Hematol 30, 503-512, and relative expression was calculated as per Gray, J. W., Suzuki, S., Kuo, W. L., Polikoff, D., Deavers, M., Smith-McCune, K., Berchuck, A., Pinkel, D., Albertson, D., and Mills, G. B. (2003). Specific keynote: genome copy number abnormalities in ovarian cancer. Gynecol Oncol 88, S16-21; discussion S22-14, both references which are hereby incorporated by reference. The primer sequences and Taqman® probe in Assays were designed with ABI Primer Express 2.0 software. Primer and probe concentrations of 500 nM and 200 nM, were used respectively. The cDNA equivalent to 3-5 ng of RNA was measured in triplicates by real time PCR using QPCR master mix with final concentrations 5.5 mM $MgCl_2$, 200 mM dNTPs and 0.5 units HotstartAmpliTaq Gold (AB) in 20 µl volume 384 well plate or 50 µL volume for 96 well plates. For normalization, cDNA equivalent to 3-5 ng input RNA was measured for house keeping control genes such as ribosomal 18S, glyceraldehyde-3-phosphate dehydrogenase (GAPDH) and cyclophilin. The PCR protocol was as follows: 95° C., 10 min; 45 cycles of 95° C., 15 seconds and 60° C., 1 minute.

The sequences of the probes and primers used in the assay are specified below:

```
Human PVT geneI-III TaqMan ® assay, Spans intron of
GenBank Accession No. M34428
Taqman ® amplicon:
SEQ ID NO: 20
CATCCGGCGCTCAGCTGGGCTTGAGCTGACCATACTCCCTGGAGCCTTCT

CCCGAGGTGGGCGGGTGACCTTGGCACATACAGCCATCATGA

PVT1 Primers (5'-3')
SEQ ID NO: 21
Forward: CATCCGGCGCTCAGCT

SEQ ID NO: 22
Reverse: TCATGATGGCTGTATGTGCCA

TaqMan ® probe:
SEQ ID NO: 23
5'-FAM-CTGACCATACTCCCTGGAGCCTTCTCC-BHQ1-3'
```

A comparison between the array CGH measurements of genome copy number at 8q24 and quantitative PCR analyses of expression levels for PVT1 and MYC in 21 ovarian cancer cell lines was carried out. Genome copy number was assessed at the BAC array probe (VYS08A2679) closest to PVT1 and MYC, which is overlapping with parts of genomic sequences of both PVT1 and MYC genes. Across the 20 ovarian cancer cell lines, both PVT1 and MYC transcript levels were correlated with genome copy number as obtained by array CGH in Example 1.

Interestingly, the correlation between copy number and expression level was higher for PVT1 than MYC; 0.89 and 0.64, respectively. This is explained by the fact that some cell lines (e.g. OVCAR8) with amplification at 8q24 did not over express MYC while transcription levels of PVT1 were high in all lines (e.g. CAOV4, HEY, OVCA432 and OVCAR8) showing amplification at 8q24. Overall, the transcription levels of MYC and PVT1 in lines in which they were amplified were significantly higher than in most of the cell lines in which they were not amplified, although some exceptions were noted. For example, PVT1 is highly expressed in the cell lines, TOV21G, even though it is not amplified suggesting another mechanism of over expression. Table 7 shows the results of the comparison.

TABLE 7

Comparison of array CGH measurements of genome copy number at 8q24 and quantitative PCR analyses of expression levels for PVT1 and MYC in 21 ovarian cancer cell lines

| cell line name | PVT1 Taqman expression (normalized to the expression of Stratagen RNA Reference Pool) | clone VYS08A2679 copy number changes (log2 ratio cell line vs normal) | c-MYC Taqman expression (normalized to the expression of Stratagen RNA Reference Pool) |
|---|---|---|---|
| A2780 | 0.91 | −0.17 | 1.14 |
| CAOV3 | 0.91 | −0.04 | 0.09 |
| CAOV4* | 21.36 | 3.15 | 2.49 |
| DOV13 | 2.05 | −0.07 | 0.60 |
| ES-2 | 1.29 | 0.32 | 0.86 |
| HEY | 5.09 | 0.63 | 2.88 |
| OCC1 | 0.67 | −0.44 | 0.30 |
| OV90 | 0.25 | −0.02 | 0.62 |
| OVCA 420 | 1.89 | 0.54 | 1.92 |
| OVCA429 | 3.28 | 0.09 | 0.72 |
| OVCA432 | 7.18 | 0.91 | 1.25 |
| OVCA433 | 3.14 | 0.04 | 0.62 |
| OVCAR3 | 1.47 | 0.52 | 0.45 |
| OVCAR5 | 2.93 | 0.73 | 1.24 |
| OVCAR8 | 3.54 | 1.09 | 1.00 |
| PA-1 | 2.55 | −0.01 | 0.80 |
| SKOV3 | 0.70 | 0.09 | 0.76 |
| SW626 | 1.95 | 0.22 | 1.63 |
| TOV112D | 1.25 | 0.40 | 1.19 |
| TOV21G | 5.74 | 0.00 | 0.82 |
| correlation coefficency | $r^2 = 0.89$ | | $r^2 = 0.64$ |

Example 6

Developing siRNAs to Induce Apopotosis

One specific aim is to develop siRNA and/or small molecule inhibitors for genes in regions of amplification at 8q24, 11q13 and/or 20q11-q13 that cause reduced apoptotic surveillance when over expressed. We have given initial priority to PVT1 since it maps to the region of amplification at 8q24 that is most strongly associated with reduced survival duration in platinum/taxane treated patients and inhibitors of PVT1 induce strong apoptotic responses in cell lines in which it is amplified.

We propose that down regulation of PVT1 at 8q24 and other genes at 11q13 and 20q11-13 using siRNAs will be preferentially toxic to cells detected as amplified using a FISH assay, described herein, to show that down regulation will enhance response to platinum and taxane compounds and that amplification at 8q24, 11q13 and 20q11-q13 will increase resistance to carboplatin and/or paclitaxel. By way of example, we demonstrate that down regulation of PVT1 is toxic to cell and results in increased apoptotic levels that can enhance response to platinum and taxane compound therapy.

The primary tumor studies showing an association between amplification at 8q24, 11q13 and 20q11-q13 with reduced survival duration in platinum/taxane treated patients suggests that the amplification confers resistance to the drugs by suppressing apoptotic elimination of cells carrying drug induced damage. We propose a two-way approach to this study: (a) We will treat cells in the panel of 35 cell lines with carboplatin or paclitaxel and determine whether the presence/level of amplification at 8q24, 11q13 and/or 20q11-q13 is correlates with drug resistance and (b) We will transfect PVT1 and other amplified, over expressed genes into ovarian cancer cell lines that are not amplified and sensitive to carboplatin and determine the extent to which transfection induces resistance.

Methods.

Work in this Example involves development of a panel of siRNAs and expression constructs against each target gene and selection of one siRNA that maximally inhibits target gene RNA levels and produces few off target effects.

siRNA Optimization and Validation.

Optimization will be accomplished by producing ~10 siRNAs directed along the length of each target gene including the noncoding region. siRNAs will be designed using the IDT biotool available at www.idtdna.com and purchased from IDT. siRNAs that inhibit gene expression by >75% as measured by quantitative PCR will be evaluated for off target effects by assessing (a) gene expression using Affymetrix U133A arrays, (b) apoptosis pathway proteins and phosphoproteins using lysate arrays and (c) cellular cell cycle and apoptotic response patterns using image cytometry (see below). These effects will be assessed in cell lines that do and do not amplify the target gene (see Table 8 below). Optimized siRNAs will be selected to produce maximal inhibition of target gene expression and increased apoptosis in cells in which the target gene is amplified and over expressed and minimal apoptosis and transcriptional changes in cell lines in which the target gene is weakly expressed. One optimized siRNA for each target gene will be evaluated in all cell lines showing increased target gene copy number and/or expression and in 3 cell lines in which the target gene is not increased in copy number or over expressed. Table 7 summarizes levels of amplification at the three target loci in the 21 cell lines analyzed so far.

TABLE 8

Summary of ovarian cancer cell lines showing copy number increases at designated loci

| Locus of amplification | 0.9 > Log2 copy number > 0.5 | Log2 copy number > 0.9 |
|---|---|---|
| 8q24 | HEY, OVCA420, OVCAR3, OVCAR5, IOSE144RZ−EGF, IOSE144RZ+EGF | OVCAR432, OVCAR8, CAOV4 |
| 11q13 | OVCA420, OVCA432, OVCAR8, OVCAR5 | ES2, OVCAR3 |

TABLE 8-continued

Summary of ovarian cancer cell lines showing
copy number increases at designated loci

| Locus of amplification | 0.9 > Log2 copy number > 0.5 | Log2 copy number > 0.9 |
|---|---|---|
| 20q11 | IOSE80RZ + EGF, HEY, OVCA420, OVCA432, OVCA433, CAOV3, CAOV4, OCC1, SW626, OVCAR5 | CAOV3, OVCAR3 |

Expression Constructs.

Cell lines that are not amplified at the target loci will be transfected with a tet-inducible expression construct and tested for sensitivity to pacitaxel and carboplatin. Increased resistance after tet-induction will support the hypothesis that PVT1 and other apoptosis-associated amplicon genes confer resistance when over expressed as a result of amplification.

The full-length cDNA of PVT1 (and other genes) can be generated by 5'RACE or acquired from Openbiosystems. The GenBank accession ID for PVT1 cDNA from Openbiosystems is BC033263, which is hereby incorporated by reference. The full-length coding sequence of PVT1 is first be cloned into a Gateway entry vector so that we can standardize the use of Gateway Technology to insert cDNAs into appropriate Gateway destination vectors. This system has already been employed in our laboratory, and several of our expression vectors have been Gateway modified. PVT1 will be cloned into pDEST TM 26 or 27, mammalian expression vectors with a CMV promoter and epitope tag for detection, to use in the experiments described above. In order to purify enough protein for antibody production, PVT1 cDNA will also be cloned into a pET Gateway destination vector (i.e. pET160-DEST, Invitrogen) creating both a 6×His-tag and a Lumino tag for purification and visualization of the protein on SDS-PAGE, respectively. Lastly, the PVT1 cDNA will be recombined into a Gateway modified lentivirus vector with a tetracycline inducible promoter (obtained from Tal Kafri, UNC) and GFP to allow visualization of infected cells.

Lentiviral stocks will be prepared by transient co-transfection of the lentivirus expression construct along with plasmids packaging functions into 293FT producer cells (a derivative of HEK 293 cells) by calcium phosphate precipitation. We have found empirically that this protocol consistently yields high lentiviral titers. Approximately 48 hours after transfection, the growth medium is replaced and collected at 4-6 hour intervals thereafter for up to 2 days. Ordinarily, this system yields lentiviruses that are sufficiently concentrated in the spent medium, so that no additional centrifugation or purification steps are required. The lentivirus-containing medium is filtered through a 0.45 µm filter to remove any contaminating packaging cells, and stored in frozen aliquots prior to infection of recipient host cells. Test ampules are titered by infection of prospective host cells with 10-fold dilutions of viral supernatants, followed by drug selection and quantitation of drug-resistant colony formation. The lentiviral expression construct contains a zeocin resistance gene, therefore zeocin will be used when selecting stable clones.

Cell Culture, siRNA Manipulation and Analysis.

Cell culture and treatment with siRNAs alone and in combination with carboplatin or pacitaxel will be accomplished using a centralized, semi-automated system being developed at LBNL in collaboration with the Engineering Department. Both molecular and cellular features of the cells will be assessed before and during treatment.

In this system, stock cell lines are transferred from flasks and $5 \times 10^4$ cells will be seeded into 24-well cell culture plates and transferred to a multi-plate incubator. Individual wells are treated with 40-120 nM siRNA and 2.5-7.5 µg/ml Lipofectamine 2000 (Invitrogen) in 100 ml Opti-MEM reduced serum medium (Invtrogen) for 4 hours (with or without drug) in order to induce the necessary experimental perturbations. After 4 hours, the Opti-MEM are replaced with complete culture medium and the cells cultured for an additional 44 hours. Cell lysates then are extracted and re-formatted into standard 96-well microtiter plates using a Tecan multi-channel liquid handling system. These plates are then fed separately into RNA transcript, protein expression or cell analysis pipelines. For cellular profiling, treated cell culture plates are transported to a Cellomics High Content Imaging system (see below). Transcript profiling is accomplished using Affymetrix U133A/B arrays processed using the Affymetrix High Throughput Analysis system (installed at LBNL in December 2004 under an Affymetrix early access agreement). Protein profiling is accomplished using reverse phase protein at MD Anderson using lysate array technology in cases where suitable antibodies exist. Important pathway proteins are assessed using western blotting in cases where antibodies are not sufficiently specific for use on protein lysate arrays.

A high content fluorescence image analysis system at LBNL (Cellomics, KineticScan) was used to characterize cellular responses to siRNA inhibitors including proliferation rate, apoptotic rate and motility. The KineticScan is an automated imaging instrument that scans through the bottom of clear-bottom 24-well plates, focuses on a field of cells, and acquires images at each selected color channel. The Cellomics software identifies and measures individual features and structures within each cell in a field of cells, so that up to hundreds of cell samples can be analyzed in parallel. The software then tabulates and presents the results in user-defined formats.

In another embodiment, when Hoechst 33342 is used is a counterstain, apoptotics cells demonstrate green fluorescence, necrotic cells demonstrate both green and red fluorescence, and live cells only demonstrate the blue fluorescence from the Hoechst stain.

Cells undergoing cell division within a population are identified using the Arrayscan $V^{TT}$ based on microtubule spindle formation and chromosome condensation using the Cellomics' Mitotic Index HitKit™. Following compound treatment, cells growing in standard high density plates are fixed, permeabilized, and immunofluorescently labeled using an antibody specific for a phosphorylated epitope of a core histone protein.

Cell motility is assessed using the Arrayscan $V^{TT}$ by directly measuring the size of tracks generated by migrating cells using the Cellomics Cell Motility HitKit™. The assay is performed on live cells plated on a lawn of microscopic fluorescent beads. As cells move across the lawn, they leave clear tracks behind them. The track area is measured as an estimate of the rate of cell movement.

A Becton Dickinson cytometer can be used to measure DNA/BrdUrd distributions and/or DNA distributions during treatment. As shown in FIG. 7, BrdUrd/DNA distributions were analyzed to determine the fractions of cells in the G1, S—, and G2M phases of the cell cycle. For BrdUrd/DNA analysis, cells are pulse labeled for 30 min. with 1 µM BrdUrd, fixed in 70% ethanol, treated with RNase, denatured and stained with propidium iodide (PI) and a fluorescently labeled antibody against BrdUrd as described in Dolbeare, F., Gratzner, H., Pallavicini, M. G. & Gray, J. W. Flow cytometric measurement of total DNA content and incorporated bromodeoxyuridine. *Proc Natl Acad Sci USA* 80, 5573-7 (1983), and placed in 96 well trays for analysis.

Results.

Although both MYC and PVT1 are in the region of high level amplification at 8q24 that is most strongly associated with reduced survival duration in breast and ovarian cancer, only the over expression of PVT1 is significantly associated with reduced survival duration in our Affymetrix analyses of expression in ovarian cancer (FDR-adjusted p=0.018) and in published gene expression studies (p=0.06). Moreover, sRNA inhibition of PVT1 in ovarian cancer cell lines in which it is amplified and over expressed, blocks cells in the G1 phase of the cell cycle and induces apoptosis. siRNA inhibition of MYC, on the other hand, blocks cells in the G1-phase of the cell cycle but does not induce apoptosis.

Two cDNA sequences were used to design the PVT1 siRNA, M34428 (SEQ ID NO: 1) and XM_372058 (SEQ ID NO:2). The M34428 sequence was sent to a commercial company to design the siRNA. SEQ ID NOS: 1 and 2 were used to design primers and Taqman probe for quantitative PCR using the 'Primer Express 2.0' program from ABI Biosystems (Foster City, Calif.). For other siRNA sequences (SEQ ID NOS: 5-17), the webdesigning tool from Genescript (www.genescript.com) was used since it provides the top candidates and also performs BLAST screening (Altschul, S. F., Gish, W., Miller, W., Myers, E. W. & Lipman, D. J. (1990) "Basic local alignment search tool." *J. Mol. Biol.* 215:403-410) on each resulting siRNA sequence. When the M34428 sequence was inputted, ten including the two siRNAs (SEQ ID NOs: 3-4) used in the Examples resulted. The sense and antisense sequences are each given separate SEQUENCE ID NUMBERS. Using the other sequence, XM_372058, the Genscript design tool outputted 10 top candidate siRNAs. Five siRNA sequences were chosen that were within the overlapping regions of M34428 and XM_372058 and are SEQ ID NOS: 8-17. A short end "TT" DNA sequence was added to each siRNA sequence.

The five siRNA sequences for XM_372058 were chosen because they overlap with the M34428 sequence, and because all five siRNAs were found within the XM_372058 predicted coding region (bp 379-777). Thus siRNAs found within predicted coding regions may indicate useful siRNAs for the present invention. For sequences such as M34428, where the coding region is not known or predicted, it may be prudent to perform a study such as a 5'-RACE test to determine the actual coding sequence.

The siRNA sequences constructed are shown below:

```
SiRNA sequences for PVT in XM_372058.3 (bp75-775)
SEQ ID NO: 3
Sense:              CAGCCAUCAUGAUGGUACU SEQ ID NO: 4
Antisense:          AGUACCAUCAUGAUGGCUG SiRNA sequences designed by Genscript using M34428
sequence
SEQ ID NO: 5 (start at 348 bp in M34428)
sense:              CCGGCACAUUUCAGGAUACUA SEQ ID NO: 6 (start at 321 bp)
sense:              ACCAUGCACUGGAAUGACACA SEQ ID NO: 7 (start at 231 bp)
sense:              GCUGCAUGGAGCUUCGUUCAA
```

```
SiRNA sequences designed by Genscript using the
XM_372058 sequence
SEQ ID NO: 8 (start at 501 in XM_372058)
sense:              AGCAUCUGAUGCACGUUCCAU SEQ ID NO: 9
antisense:          AUGGAACGUGCAUCAGAUGCU SEQ ID NO: 10 (start at 689 bp)
sense:              GGACUUCGCAGCUGACCAUAC SEQ ID NO: 11
antisense:          GUAUGGUCAGCUGCGAAGUCC SEQ ID NO: 12 (start at 751 bp)
sense:              CAUACAGCCAUCAUGAUGGUA SEQ ID NO: 13
Antisense:          UACCAUCAUGAUGGCUGUAUG SEQ ID NO: 14 (start at 496 bp)
sense:              GGUGAAGCAUCUGAUGCACGU SEQ ID NO: 15
antisense:          ACGUGCAUCAGAUGCUUCACC SEQ ID NO: 16 (start at 690 bp)
sense:              GACUUCGCAGCUGACCAUACU SEQ ID NO: 17
antisense:          AGUAUGGUCAGCUGCGAAGUC SiRNA sequences against c-myc
SEQ ID NO: 18
Sense:              5' GAGGCGAACACACAACGUC 3'

SEQ ID NO: 19
AntiSense:          5' GACGUUGUGUGUUCGCCUC 3'
```

Figure 8:
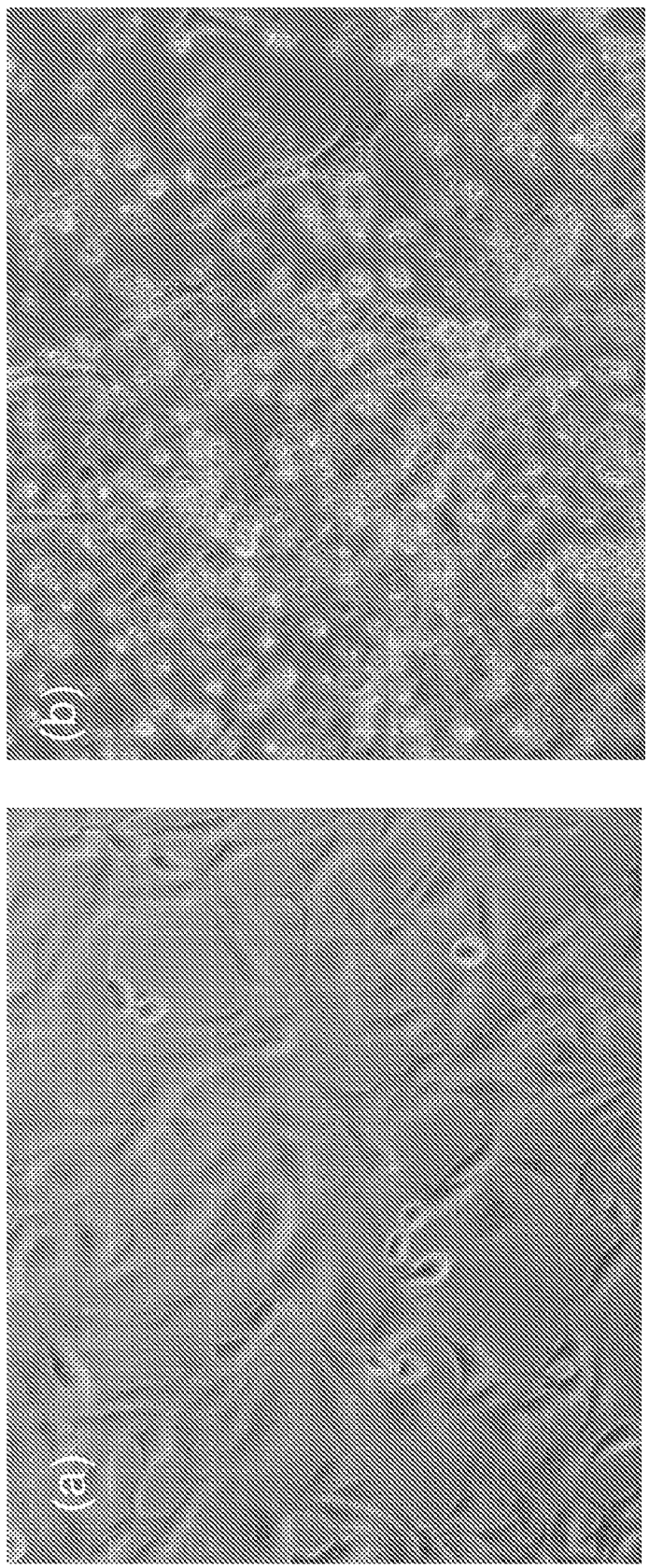
FIG. 8A shows a phase contract photomicrograph of mock treated HEY cells.
FIG. 8B shows a phase contrast photomicrograph of HEY cells after treatment with an siRNA against PVT1. Apoptotic blebbing is clearly apparent.
Figure 9A:
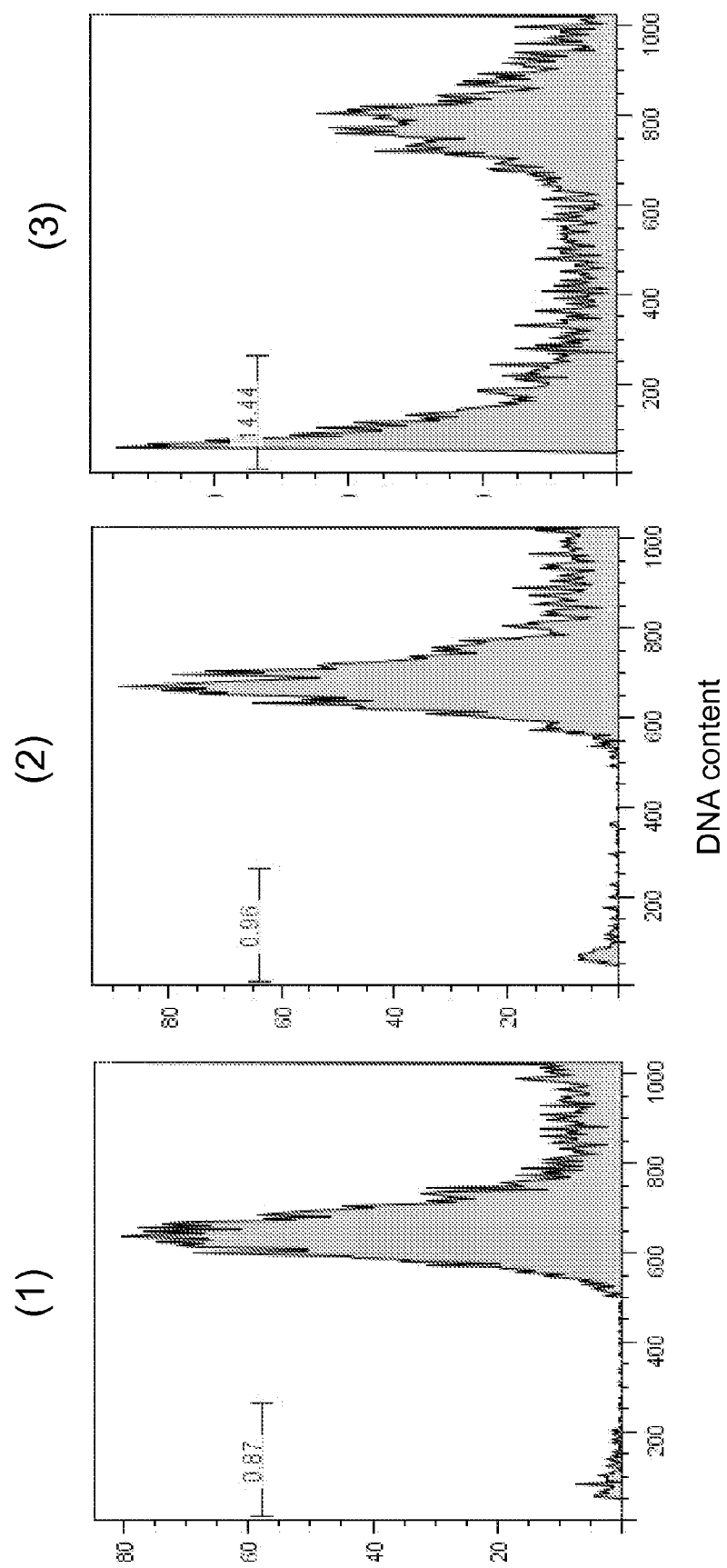
FIG. 9A(1) shows a graph of the G1-peak region of a DNA content distribution for mock treated CAOV4 cells.

FIG. 8A shows phase contrast photomicrographs for HEY cells sham treated and FIG. 8B shows photomicrographs for HEY cells treated for 48 hours with a siRNA against PVT1. The apoptotic blebbing after siRNA inhibition of PVT1 is apparent. FIG. 9A also shows DNA distributions for the region below the G1-peak for CAOV4 cells sham treated (panel 1) or treated with siRNAs against MYC (panel 2) or PVT1 (panel 3). Apoptosis induced DNA fragments are present after PVT1 inhibition but not after MYC inhibition.

Figure 7A:
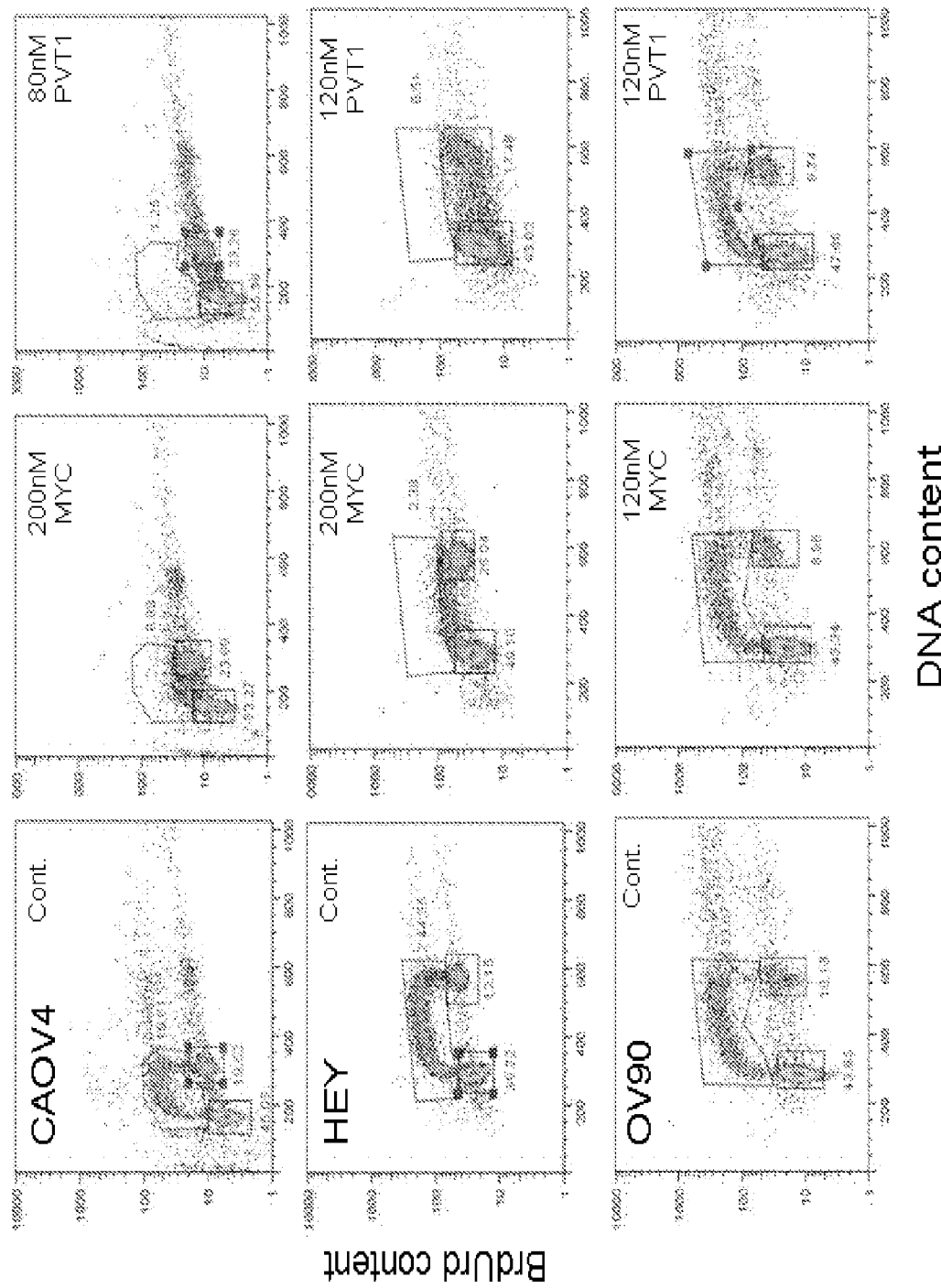
FIG. 7A is a set of graphs showing the BrdUrd vs. DNA distributions (30 min BrdUrd pulse label) measured 48 hours after treatment with siRNA inhibitors. The identities of the siRNA inhibitors are indicated in the figure. The cell lines CAOV4 and HEY carry high level amplification at 8q24.13 while OV90 does not. The fractions of cell in the G1, S and G2M phases of the cell cycle are indicated in the plots.

Referring to FIG. 7A, for example, shows BrdUrd/DNA distributions measured before and 48 hours after treatment with siRNAs against PVT1 and MYC for the cell lines CAOV4 and HEY in which PVT1 and MYC are highly amplified and in OV90 in which MYC and PVT1 are not amplified. Cell cycle progression is strongly inhibited in the PVT1/MYC amplified lines but not in the unamplified line.

Figure 7B:
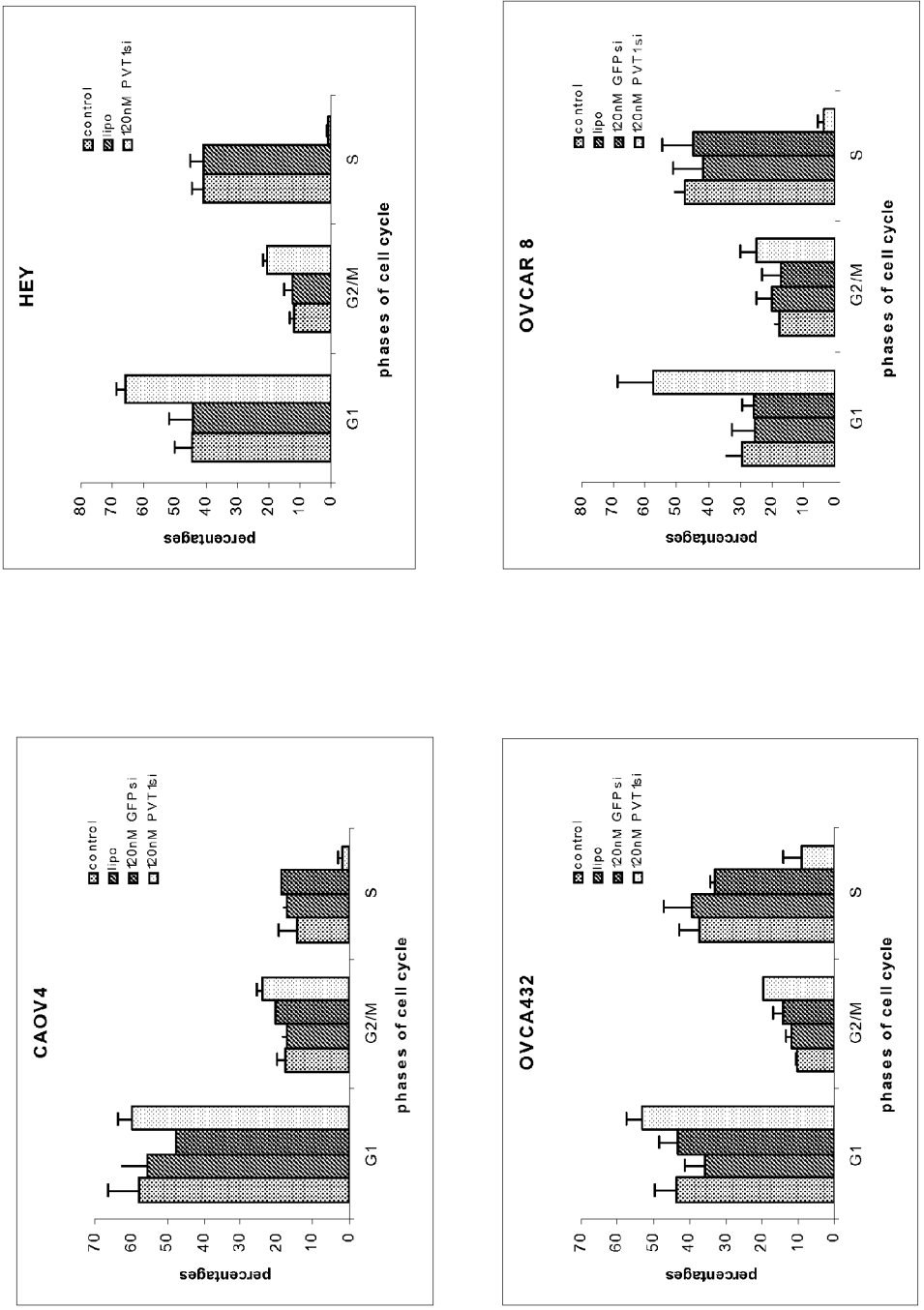
FIG. 7B is a set of graphs showing the effects on cell cycle by PVT1 siRNA in cell Lines expressing PVT1.
Figure 7C:
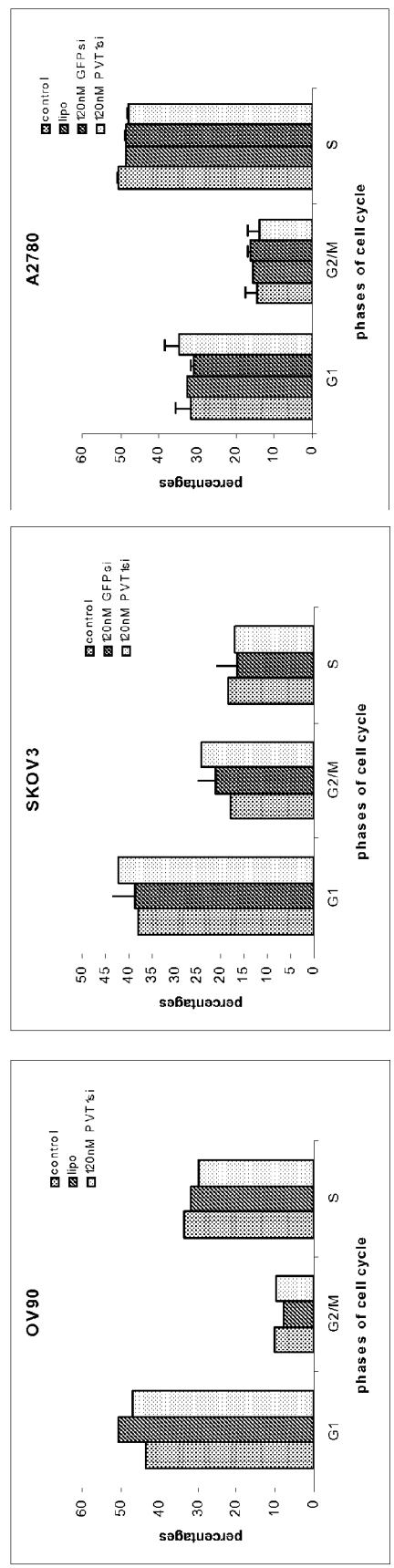
FIG. 7C is a set of graphs showing the effects on cell cycle by PVT1siRNA in cell lines not expressing PVT1.

In FIGS. 7B and 7C, the BrdU data is measuring proportions of cell cycle phases of ovarian cancer cell lines that overexpress PVT1. Referring to the graphs in FIGS. 7B and 7C, cells were left untreated (control, blue bar), treated with lipofectamine 2000 (lipo, purple bar) and green fluorescent protein (GFP; green bar) as controls or treated with PVT1 siRNA (PVT1 si, yellow bar, SEQ ID NO: 3 and 4). The error bars are standard deviation values from more than one experiment. If there are no error bars on a column, it means the experiment was not repeated. Focusing on the yellow columns which represent PVT1 siRNA treated, it was observed that S phase in cell lines overexpressing PVT1 are much shorter than in the 3 control columns (FIG. 7B). FIG. 7C shows the same experiments performed on ovarian cancer cell lines that do not express PVT1. The yellow columns from S phase have almost the same heights as the 3 controls, showing that PVT1 siRNA does not affect the cell cycle of cell lines not expressing PVT1.

Cell Panel Experiments.

Cells from each line are established in 24-well cultures as described above and treated with carboplatin or pacilitaxel at 4 concentrations for 24 and 48 hours. Apoptotic indices are measured as described above using both flow cytometry (extent of subG1-fragments) and image cytometry (using the Cellomics Apoptosis 1 HitKit™). Statistically significant correlations between level of carboplatin or pacitaxel induced apoptosis and amplification level across all cell lines will be assessed to determine the strength of correlation. A high correlation will support the hypothesis that amplification associated gene activation contributes to the development of resistance to carboplatin and/or pacitaxel.

Three non-amplified ovarian cancer cell lines can be transfected with PVT1 or other target genes from Example 1. Cells from each transfected line and its control will be established in multi-well cultures as described and treated with carboplatin or pacitaxel at 4 concentrations for 24 and 48 hours. Apoptotic indices will be measured as described herein using both flow cytometry (extent of subG1-fragments) and image cytometry (using the Cellomics Apoptosis 1 HitKit™). Reduced apoptosis in cell lines transfected with active constructs relative to controls transfected with inactive constructs will support the hypothesis that amplification associated gene activation contributes to the development of resistance to carboplatin and/or pacitaxel.

Referring again to FIG. 8, an additional measure of apoptosis can include staining with an Alexa Fluor® 488 conjugate of annexin V (Molecular Probes) and staining with propidium iodide (PI). PI is impermeable to apoptotic cells and live cells, but can enter and bind nucleic acids in necrotic cells. An apoptotic index can be assessed by measuring the fraction of "sub diploid" cells after staining for DNA content using PI as illustrated in FIG. 8A. Cells are fixed in 70% ethanol, treated with RNAse and placed in 96-well trays for DNA content analysis. FIG. 8A shows phase contrast photomicrographs for HEY cells sham treated and/or treated for 48 hours with a siRNA against PVT1 (FIG. 8B) (SEQ ID NO: 3 and 4). The apoptotic blebbing after siRNA inhibition of PVT1 is apparent in FIG. 8A panel 2.

Figure 9B:
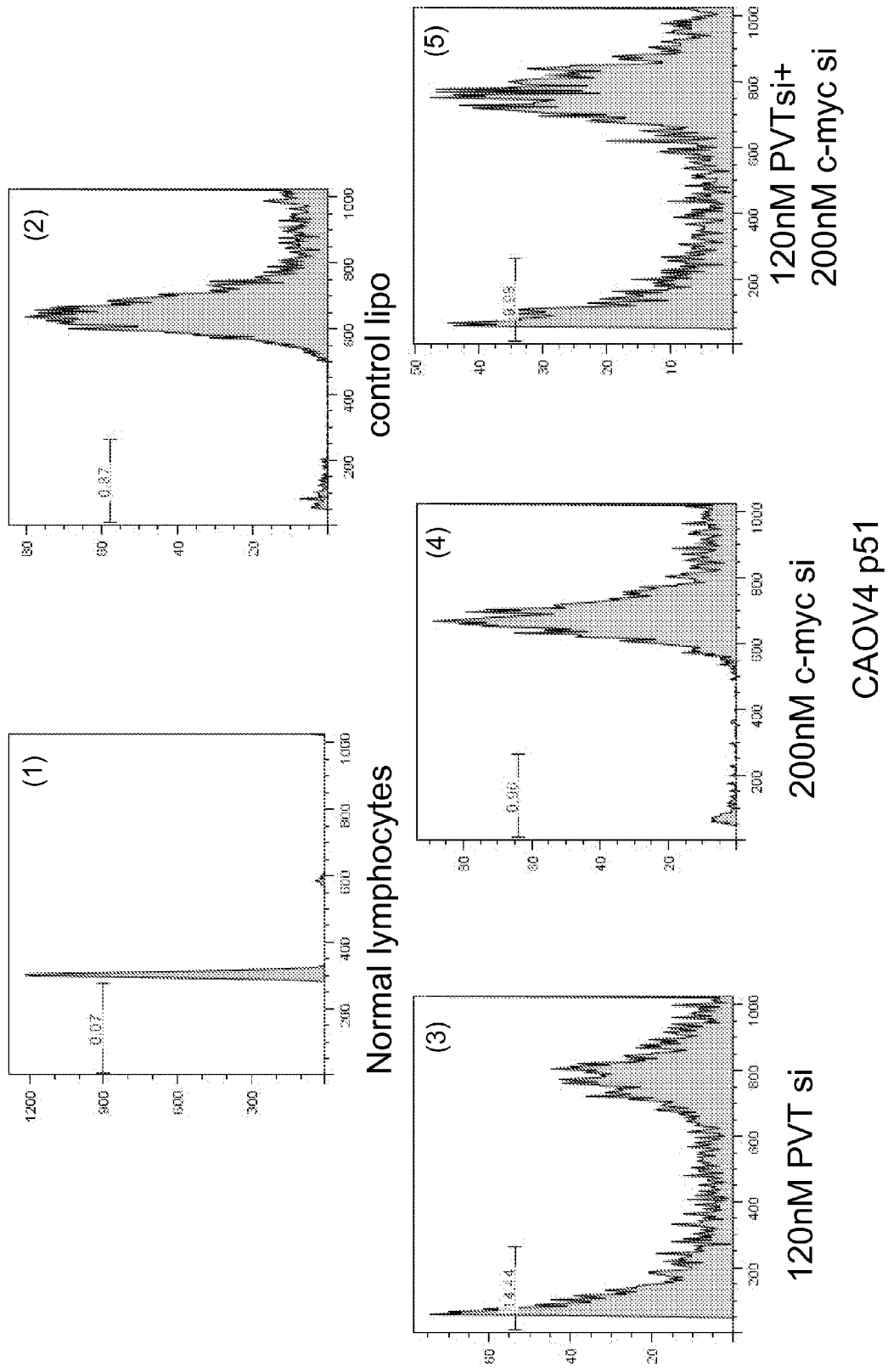
FIG. 9B is a set of graphs showing the combinational effects of siRNAs against PVT1 and c-myc on apoptosis using PI staining for DNA distribution.

FIG. 9A also shows DNA distributions for the region below the diploid cell-peak for CAOV4 cells sham treated (panel 1) or treated with siRNAs against MYC (panel 2; SEQ ID NO: 18 and 19) or PVT1 (panel 3; SEQ ID NO: 3 and 4). Apoptosis induced DNA fragments are present after PVT1 inhibition but not after MYC inhibition. In FIG. 9B, the first plot is the PI staining of normal lymphocytes. The first sharp peak marks the position of diploid cells, and the border of the apoptotic population. Looking at the peak distribution in cell treated with PVT1 siRNA shows a radically different DNA content than normal or even MYC siRNA-treated cells.

These data suggest the interesting possibility that amplification of 8q24 performs two simultaneous oncogenic functions; activation of MYC which stimulates proliferation and activation of PVT1 which inhibits the apoptotic response normally associated with MYC activation[51]. In this context, PVT1 is a much more attractive therapeutic target than MYC since inhibition of MYC will likely be cytostatic while inhibition of PVT1 will generate a strong apoptotic effect. Therefore, development of PVT1 inhibitors will be pursued at highest priority in the following Examples.

Referring to FIG. 10, PVT siRNA-treated ovarian cell lines were analyzed by high content imaging for apoptosis. Apoptotic cells were detected based on nuclear morphology, mitochondrial mass and/or membrane potential, and f-actin content following staining with the Cellomics Multiparameter Apoptosis 1 HitKit™. Nuclear morphology (i.e., condensation or fragmentation) are measured after staining with Hoechst 33342. Mitochondrial membrane potential and mitochondrial mass are measured after staining with MitoTracker® Red. F-actin is measured after staining with an Alexa Fluor® 488 conjugate of phalloidin (Ax488-ph). Changes in the actin cytoskeleton have been used as a potential parameter related to apoptotic changes. Early increase of F-actin content in cells are one of the changes in the cytoskeleton that can be used to measure apoptosis.

Referring to FIG. 10A, the F-actin content and thereby apoptosis in cell lines having no increased PVT1 amplification remained low. Increased F-actin content was observed for cell lines which overamplify PVT1 after treatment with PVT1 siRNA (SEQ ID NO: 3 and 4). Referring to FIGS. 10B and 10C, fluorescence intensity in apoptotic cells were detected based on nuclear morphology, mitochondrial mass and/or membrane potential, and f-actin content in ovarian cancer cell lines. Cell lines that do not amplify PVT1, then treated with the PVT1 siRNA showed normal apoptotic levels (FIG. 6B). Cell lines that do amplify PVT1, then treated with the PVT1 siRNA showed increased apoptotic levels, higher than levels of cells treated with paclitaxel (FIG. 10C).

Thus, an siRNA against PVT1 (SEQ ID NO: 3 and 4) induced apoptosis in cell lines in which PVT1 is amplified produces no apoptotic response in a cell line in which it is not amplified. While it may be possible that the results we have achieved so far will be influenced by off target effects, further analysis of multiple siRNAs for each target gene and analysis of responses in cell line panels will guard against this possibility as will detailed functional assessments of PVT1 and other amplicon genes.

Example 7

Delivery of siRNA Inhibitors of PVT1

Inhibitors such as siRNA and/or small molecular inhibitor formulations can be developed to deliver PVT1 (and other) inhibitors efficiently to cultured cells and xenografts. We describe two approaches to development of amplicon gene inhibitors. Highest in initial priority will be given to PVT1. One approach will be to deliver optimized siRNAs complexed to polymer-coated cationic liposomes. The other approach will be to develop small molecule inhibitors for targets located in key amplified regions in ovarian tumors that have been functionally validated using siRNAs. Apoptotic indices will be measured for cell lines and xenografts in which the target genes are amplified and that respond apoptotically to treatment with siRNAs plus lipofectamine (e.g. HEY and CAOV4 for PVT1 as illustrated in FIGS. 7 and 8). Constructs that induce apoptosis in cell lines/xenografts where the target is amplified and not when the target is not amplified AND that minimally toxic in vivo will be evaluated further. Inhibitor constructs will be developed tested at four concentrations in vitro and then in vivo to establish efficacy and toxicity.

Liposome Bound siRNA Inhibitors.

Optimized siRNAs (e.g., SEQ ID NOS: 3-17) directed against each target gene found in Example 1 will be complexed to non-viral gene delivery system that can be administered in vivo or in vitro. Initially the gene target to complexed is PVT1 (designated siPVT1) and its scrambled controls (designated siPVT1$^{sc}$). Specifically, siRNAs will be bound to SN (e.g. siPVT1-SN), a polymer-coated cationic liposome formulation composed of 1,2-dipalmitoyl-sn-glycerol-3-ethylphosphocholine, 1,2-dipalmitoyl-sn-glycero-3-phosphoethanoamine-N-polyethyleneglycol-5000 and polyethylenimine. The siRNAs are entrapped in the liposome after the thin-lipid film is hydrated and extruded through a filter with 0.2 µm diameter pores. The lipid/siRNA ratio will be 12:1, and the liposomal siRNA particle size will be 70-170 nm in diameter. The extended polyethylene glycol (PEG) on the surface of the liposomes protects the liposome from being attacked by blood components and engulfed by phagocytes in vivo thereby increasing tumor specificity and increasing stability.

Small Molecule Inhibitors.

Small molecule inhibitors will be developed in collaboration. This work will begin with identification of lead compounds by setting up a high throughput screen, obtaining the necessary proteins and reagents to carry out the screen, and conducting the screen using a proprietary collection of small molecules. For those targets whose function is known (e.g., STK4 from Table 1), we will set up functional assays. If the function of the protein target is previously unknown (e.g. PVT1) or cannot be predicted from homology modeling, we will use a binding assay that involves affinity selection with mass spectrometry. Once lead compounds have been identified in the high throughput screen, they will be tested in cell-based apoptosis assays using cells that have the region amplified where the target gene is located. These results will be compared to those obtained in apoptosis assays using cells that do not have the region amplified. Next, promising lead compounds will be optimized for binding to the target, cell penetration and cell-based activity, and pharmacokinetic properties. If a suitable optimized lead compound can be obtained, it will be tested in xenograft tumor models for efficacy and possible toxicity.

Test Systems.

Inhibitors will be tested in cell lines that are amplified at the target loci as determined by array CGH (see Tables 7 and 8). Cells in 24-well cultures will be treated with inhibitors over a concentration range in order to determine the degree to which target gene expression is reduced at the RNA level and the concentration that induces apoptosis at 90% of the maximum achieved (maximum apoptosis index, MAI). Three different target-amplified cell lines will be tested in order to determine an average working concentration for further experiments. Quantitative RT-PCR will be used to assess changes in gene expression. Other methods will be as described in Example 2.

Inhibitors will be tested in vivo in orthotopic xenograft models of ovarian cancer have proven useful for the characterization of ovarian tumor growth and metastasis in vivo as well as for testing novel therapeutics for the treatment of ovarian cancer (Stakleff, K. D. & Von Gruenigen, V. E. Rodent models for ovarian cancer research. *Int J Gynecol Cancer* 13, 405-13 (2003); Vanderhyden, B. C., Shaw, T. J. & Ethier, J. F. Animal models of ovarian cancer. *Reprod Biol Endocrinol* 1, 67 (2003); and Senterman, M. K., Dawson, K., Crane, C. A. & Vanderhyden, B. C. Characterization of intraperitoneal, orthotopic, and metastatic xenograft models of human ovarian cancer. *Mol Ther* 10, 1032-42 (2004). Xenografts will be established by injecting human ovarian cancer cell lines directly into the peritoneum of immunodeficient nude mice. This orthotopic model of ovarian cancer mimics the pattern of tumor spread in the peritoneum seen in the majority of human patients with advanced disease.

Not all xenografts of human ovarian cancer cell lines form intraperitoneal tumors. Fortunately, we have at least two ovarian cancer cell lines that express increased copy numbers of each of our target loci, 8q24, 11q13, and 20q11-q13, and that are also suitable for xenograft studies (Senterman, M. K., et al., *Mol Ther* 10, 1032-42 (2004); Hamilton, T. C. et al. Characterization of a xenograft model of human ovarian carcinoma which produces ascites and intraabdominal carcinomatosis in mice. *Cancer Res* 44, 5286-90 (1984); Buick, R. N., Pullano, R. & Trent, J. M. Comparative properties of five human ovarian adenocarcinoma cell lines. *Cancer Res* 45, 3668-76 (1985); Lau, D. H., Lewis, A. D., Ehsan, M. N. & Sikic, B. I. Multifactorial mechanisms associated with broad cross-resistance of ovarian carcinoma cells selected by cyanomorpholino doxorubicin. *Cancer Res* 51, 5181-7 (1991). OVCAR3 demonstrates amplification of all three loci. HEY will be used to generate xenografts to study amplification at 8q24 and 20q11-q13, and ES2 will be utilized to study amplification at 11q13. Multiple lies for each target is advantageous since individual cell lines demonstrate different histological and growth characteristics (Senterman, M. K., et al., (2004)). For example, data (not presented) demonstrate mice injected intraperitoneally (ip.) with the ovarian cancer cell lines HEYA8 and SKOV3. Histological sections of these tumors demonstrate similarity to human tumors. In this experiment, 9 out of 10 mice injected with HEYA8 cells developed peritoneal tumors and all 10 mice injected with SKOV3 developed tumors. Mice receiving an i.p injection of HEYA8 cells (median survival 30 days, range 28-42 days) developed large (up to 10 mm in diameter) peritoneal lesions with 2-4 discrete lesions per mouse. Mice given an i.p injection of SKOV3 (median survival 40 days, range 35-51 days) developed multiple nodules ranging in size from 2-5 mm in diameter.

In another embodiment, we will select compounds that induce high levels of apoptosis in cell lines in which the target is amplified and low levels otherwise AND that inhibit growth in xenografts where the target is amplified (e.g. HEY for PVT1) and not in xenografts where the target is not amplified (e.g. SKOV3 for PVT1). Apoptosis will be measured in vitro as described above. Apoptosis will be measured in xenografts by assessing the frequency of pyknotic nuclei in four high powered fields in H&E sections and/or by assessing the frequency of cells that stain positively with antibodies against caspase 3.

Activity.

We will assess activity of candidate inhibitory formulations (e.g. siPVT1-DOPC) and control formulations (e.g. siPVT1$^{sc}$-DOPC) in mice bearing well established xenografts in which the target gene is amplified. Six groups of 10 mice will be injected i.p with $10^6$ tumor cells (e.g. HEY for PVT1). Tumors will be allowed to progress for 7 days at which time the animals will be injected with a single dose of each formulation as several different concentrations and three mice will sacrificed at 1 hour, 6 hours, 24 hours, 4 days, 7 days and 10 days. Each experiment will be repeated in triplicate. Samples of tumor tissue will be flash frozen for protein and RNA extraction, and formalin-fixed and paraffin-embedded for immunohistochemical analysis of target protein expression levels following siRNA therapy. An apoptotic index will be measured as the frequency of pyknotic nuclei in four high power fields in H&E sections and/or the frequency of cells that stain positively with an antibody against caspase 3. These studies will establish the 90% MAI concentration for each formulation. Inhibition of gene expression at the RNA level will be measured using quantitative RT-PCR. Inhibition at the protein level will be measured using western analysis and/or immunohistochemistry when suitable antibodies are available.

Successful development of inhibitory constructs that can be delivered in vivo builds on liposome mediated gene delivery technologies described above and on high throughput small molecule screening. Some problems with siRNAs may arise due to inefficient delivery or to unacceptable toxicity. These may be overcome, for example, by using neutral liposomes and/or by targeting the liposomes to the folate receptor (FR), to increase the specificity for ovarian cancer. FR is a glycosylphosphatidylinositol-anchored membrane protein and overexpressed in a wide variety of human tumors while exhibiting highly restricted normal tissue distribution and the subtype, FR-α, is over expressed in 90% of ovarian carcinomas. These and other methods are more fully addressed herein.

Example 8

Effective Formulations of PVT1 Inhibitors

PVT1 (and other) inhibitory formulations developed in Examples 6-7 will be tested for their preferential effectiveness against xenografts that are amplified at the target loci and to test whether they enhance response to platinum and taxane compounds. The most effective formulation will be developed for clinical application. Basically we will establish xenograft models that are positive (i.e. amplified at least log 2>0.5) for each amplified locus (see Tables 7 and 8); determine baseline paclitaxel and carboplatin responses for all xenograft models; determine responses to an anti PVT1 Rx; measure responses to next priority target (designated T2) and responses to PVT1 plus carboplatin; and finally measure responses to PVT1+paclitaxel and responses of T2+carboplatin Formulations that inhibit gene expression in xenografts and for which the 90% MAI concentration is less than the LD50 in xenografts that are amplified at the target locus will be tested at the 90% MAI concentration in xenografts in which the target locus is not amplified.

Formulations that exhibit target specificity (i.e. induce apoptosis in models in which the target is amplified and not in models where the target is not amplified) will be tested against xenografts in which the target is amplified at the 90% MAI concentration and at 2- and 4-fold lower doses in combination with carboplatin or paclitaxel (given at the MTD) in order to determine the extent to which amplicon inhibitors can enhance sensitivity to platinum/taxane based therapies. OVCAR3, HEY and ES2 will be used in these studies since each target locus is amplified in two or more of these lines, all form xenografts and all demonstrate some resistance to cisplatin. Assuming that successful inhibition of a target gene and an apoptotic response can be achieved in vivo, we will evaluate inhibitor treatment schedules alone and in combination with carboplatin or paclitaxel.

We will assess the target specificity of targeted formulations by treating mice bearing well established xenografts that are not amplified for at the target will be injected with a single dose of the inhibitory formulation. As an example, mice bearing well established ES2 xenografts (not amplified for PVT1) will be treated with siPVT1-DOPC and assessed for apoptotic response. Mice will be sacrificed at 1 hour, 6 hours, 24 hours, 4 days, 7 days and 10 days. The experiment will be repeated in triplicate. Samples of tumor tissue will be flash frozen for protein extraction, and formalin-fixed and paraffin-embedded for immunohistochemical analysis of apoptotic response. Lack of apoptotic response will be taken as an indication of specificity since all formulations tested at this stage will already have demonstrated effectiveness in xenografts in which the target is amplified.

We will evaluate the efficacy of inhibitory gene-targeted formulations (e.g. siPVT1-DOPC) against tumors amplified at the target locus alone and in combination with carboplatin (60 mg/kg twice weekly) and paclitaxel (100 µg/week). Six groups of ten mice will be injected intraperitoneally with $10^6$ cells from a line in which the target is amplified (e.g. HEY for PVT1). Tumors will be allowed to progress for 7 days at which time the animals will be divided into six treatment groups; untreated; carboplatin iv twice weekly; paclitaxel iv weekly; gene targeted formulation iv twice weekly; gene targeted formulation plus carboplatin twice weekly; and gene targeted formulation plus paclitaxel weekly. Treatment will be conducted for four weeks, at which time the animals will be sacrificed and a necropsy performed. All tumor tissue will be excised from each mouse and weighed. Total tumor weight will be compared between treatment groups. In addition, tumors will be formalin-fixed and paraffin embedded for the comparison and analysis of histological changes resulting from each therapeutic regime.

Outcomes to be observed include gene amplification/expression levels and apoptotic response in vitro and tumor growth and survival in vivo. Survival data will be analyzed using Kaplan-Meier estimates and compared using the log-rank test. Continuous outcomes will be compared across treatment groups using ANOVA. Continuous measures will be compared against each other (e.g. amplification versus apoptosis) using regression analysis. Tumor growth data will be analyzed using repeated measures ANOVA. We will compute appropriate sample sizes for all animal experiments. For example, based on previous experiments we know that the standard deviation of weights in normal control mice is generally less than 10% of the mean body weight. If a difference of 15% between control and treatment groups is of scientific interest and assuming body weights are normally distributed, then to achieve a 90% power to detect a 15% difference in weight between two groups using a two-sided test at a significance level of 10% requires 11 animals per group.

Example 9

In Vivo siRNA Delivery

The feasibility of therapeutic liposomal siRNA delivery to tumors in vivo has been demonstrated herein. The results of the studies are described below. This technology will be adapted to inhibit PVT1 and other amplicon genes in preclinical mouse xenograft models of ovarian cancer.

Liposome Formulation.

Gene specific siRNAs, and corresponding scrambled controls, were encapsulated in 1,2-Dioleoyl-sn-glycero-3-phosphatidylcholine (DOPC). DOPC and siRNA were mixed in the presence of excess tertiary-butanol at a ratio of 1:10 siRNA:DOPC (weight:weight). Tween-20 was added to the mixture in a ratio of 1:19 Tween-20:siRNA/DOPC The mixture was vortexed, frozen in an acetone/dry ice bath, and lyophilized. Prior to in vivo administration, this preparation was hydrated with normal saline at a concentration of 15 µg/ml, to achieve the desired dose in 150-200 µl per injection.

DOPC Liposomal Delivery of siRNA In Vivo:

Studies were conducted that examined the kinetics, efficiency and distribution of siRNA delivery to both normal and tumor tissues in a mouse xenograft model of ovarian cancer using nanoparticle encapsulated as well as unmodified siRNA (Landen, C. N. et al. Therapeutic EphA2 gene targeting by in vivo liposomal siRNA delivery. *Nature Medicine* (Submitted) (2005)). Five micrograms of fluorescently labeled (Alexa-555), non-specific siRNA encapsulated in neutral liposomes (1,2-Dioleoyl-sn-glycero-3-phosphatidylcholine or DOPC) or unmodified Alexa-555-siRNA, was administered to mice intravenously with HEYA8 tumors (15 days following imp. injection of tumor cells). The delivery of Alexa-555-labeled siRNA to major organs, including heart, lung, brain, liver, kidney and spleen, as well as the tumor was analyzed using confocal microscopy. Interestingly, fluorescently labeled siRNA was detectable in tumor tissue as early as 1 hour following iv injection and persisted for up to 10 days (data not shown). This preferential uptake of long circulating liposomes and other macromolecules by tumors has been previously described as the enhanced permeability and retention (EPR) effect (Maeda, H., Wu, J., Sawa, T., Matsumura, Y. & Hori, K. Tumor vascular permeability and the EPR effect in macromolecular therapeutics: a review. *J Control Release* 65, 271-84 (2000)). Alexa-555-labeled siRNA accumulation was also detectable in normal liver, kidney, spleen and lung. Overall, uptake of DOPC encapsulated siRNA was 30-fold higher than that observed with unencapsulated siRNA. Furthermore, the neutral liposomal formulation of DOPC mediated siRNA delivery was 10-fold more efficient than that observed with a cationic DOTAP (N-[1-(2,3-Dioleoyloxy)propyl]-N,N,N-trimethylammonium methyl sulfate) liposome formulation. These data confirm increased efficiency of siRNA delivery using DOPC liposomes, and underscore the systemic delivery of siRNAs using this method.

Gene Specific Targeting of EPHA2 Using DOPC-EPHA2 siRNA:

Using this formulation of liposomal siRNA delivery, the in vivo inhibition of the EPHA2 receptor tyrosine kinase expression in ovarian tumors was subsequently demonstrated (Landen, C. N. et al. Therapeutic EphA2 gene targeting by in vivo liposomal siRNA delivery. *Nature Medicine* (Submitted) (2005)). EPHA2 is thought to play a role in the regulation of normal epithelial cell growth and migration. It is overexpressed by a wide variety of epithelial tumors, and ectopic over expression of EPHA2 in normal cells is transforming (Walker-Daniels, J., Hess, A. R., Hendrix, M. J. & Kinch, M. S. Differential regulation of EphA2 in normal and malignant cells. *Am J Pathol* 162, 1037-42 (2003); Kinch, M. S. & Carles-Kinch, K. Overexpression and functional alterations of the EphA2 tyrosine kinase in cancer. *Clin Exp Metastasis* 20, 59-68 (2003)), and represents a potential therapeutic target for the treatment of epithelial cancers. In agreement with these data, studies conducted by Thaker et al, demonstrated that EPHA2 protein levels are elevated in up to 75% of ovarian tumors and that EPHA2 over expression correlates with an aggressive phenotype and poor outcome (Thaker, P. H. et al. EphA2 expression is associated with aggressive features in ovarian carcinoma. *Clin Cancer Res* 10, 5145-50 (2004)).

EPHA2 is highly expressed in the HEYA8 and SKOV3ip1 cell lines. A single dose DOPC-encapsulated EPHA2 siRNA was administered to mice possessing HEYA8 cell tumors. Mice were sacrificed at 2, 4, 7 and 10 days following treatment. Western blot analysis was used to assess EPHA2 levels in tumors of DOPC-EPHA2 siRNA-treated mice as compared to mice treated with non-specific siRNA. EPHA2 was specifically down regulated in the tumors of DOPC-EPHA2 siRNA-treated mice. EPHA2 levels remained suppressed four days following treatment, but increased to normal levels by 10 days. Based on these results, it was determined that twice weekly administration of DOPC-EPHA2 siRNA should be sufficient to maintain EPHA2 inhibition in vivo.

For therapeutic studies, mice were injected with HEYA8 or SKOV3ip1 cells. One week later, mice were treated twice weekly with DOPC-EPHA2 siRNA (150 µg/kg) alone or in combination with weekly paclitaxel (100 µg), for four consecutive weeks. Treatment with DOPC-EPHA2 siRNA, paclitaxel and a combination of DOPC-EPHA2 siRNA and paclitaxel were all effective in reducing tumor size. Combination therapy was the most effective, leading to an 86-91% reduction in tumor size as compared to animal treated with control siRNA alone (FIG. 8).

Taken together, these data demonstrate that DOPC-siRNA gene silencing can be used to specifically down regulate protein expression in ovarian tumors in vivo, and represents a promising therapeutic for the treatment of ovarian cancer. We will incorporate the technology to target candidate genes which are amplified, such as PVT1, that are potentially involved in the chemoresistance of ovarian tumors and related to reduced survival rate.

While the present sequence, compositions and processes have been described with reference to specific details of certain exemplary embodiments thereof, it is not intended that such details be regarded as limitations upon the scope of the invention. The present examples, methods, procedures, specific compounds and molecules are meant to exemplify and illustrate the invention and should in no way be seen as limiting the scope of the invention. Any patents, publications, publicly available sequences mentioned in this specification and below are indicative of levels of those skilled in the art to which the invention pertains and are hereby incorporated by reference to the same extent as if each was specifically and individually incorporated by reference.

TABLE 2

| 8q24 | | | | | |
|---|---|---|---|---|---|
| clone_ID | Cytoband_May04 | link_UCSC | May04_chr | UCSC Genome Browser May04_coor1 | UCSC Genome Browser May04_coor2 |
| RP11-367L7 | 8q24.21 | 128528775 | 8 | 128528775 | 128696124 |
| RP11-1136L8 | 8q24.21 | 128624992 | 8 | 128624992 | 128784120 |
| RP11-440N18 | 8q24.21 | 128665938 | 8 | 128665938 | 128847168 |
| RP11-237F24 | 8q24.21 | 128822387 | 8 | 128822387 | 128822827 |
| CTD-2034C18 | 8q24.21 | 128784031 | 8 | 128784031 | 128957168 |
| RP11-125A17 | 8q24.21 | 128934600 | 8 | 128934600 | 129105842 |
| RP11-946L14 | 8q24.21 | 128999600 | 8 | 128999600 | 129171481 |
| CTD-2369J14 | 8q24.21 | 129100931 | 8 | 129100931 | 129253749 |
| RP11-1082G24 | 8q24.21 | 129217209 | 8 | 129217209 | 129405998 |
| | | | | CONTIG bp: | 877223 |

| clone_ID | MapType | Accession # | BAC end seq. | BAC end seq | Gene/Marker |
|---|---|---|---|---|---|
| RP11-367L7 | bacEndPairs.short | AC104370 | AQ529915 | AQ529916 | |
| RP11-1136L8 | bacEndPairs.short | AC108925 | AQ699120 | AQ721856 | |
| RP11-440N18 | | | AQ584795 | AQ584794 | |

TABLE 2-continued

8q24

| clone_ID | MapType | | | | Gene |
|---|---|---|---|---|---|
| RP11-237F24 | fishClones.txt | | | | MYC |
| CTD-2034C18 | bacEndPairs.short | | AQ230095 | AQ230398 | |
| RP11-125A17 | bacEndPairs.short | AC011627 | AQ345999 | AQ346002 | |
| RP11-946L14 | bacEndPairs.short | | AQ599986 | AQ571565 | |
| CTD-2369J14 | | AC084089 | AQ077534 | AQ077537 | PVT1 |
| RP11-1082G24 | bacEndPairs.short | | AQ744431 | AQ744804 | |

TABLE 3

11q13.3

| clone_ID | Cytoband_May04 | link_UCSC | May04_chr | UCSC Genome Browser May04_coor1 | UCSC Genome Browser May04_coor2 | MapType |
|---|---|---|---|---|---|---|
| RP11-378E8 | 11q13.3 | 68913044 | 11 | 68913044 | 69094409 | bacEndPairs.short |
| RP11-825J6 | 11q13.3 | 68958598 | 11 | 68958598 | 69145055 | bacEndPairs.short |
| RP11-266K14 | 11q13.3 | 69145502 | 11 | 69145502 | 69298443 | bacEndPairs.short |
| RP11-300I6 | 11q13.3 | 69162461 | 11 | 69162461 | 69323966 | fishClones.txt |
| RP11-643C9 | 11q13.3 | 69297661 | 11 | 69297661 | 69494887 | bacEndPairs.short |
| RP11-368I20 | 11q13.3 | 69407011 | 11 | 69407011 | 69574983 | bacEndPairs.short |
| RP11-109F24 | 11q13.3 | 69517209 | 11 | 69517209 | 69694415 | bacEndPairs.short |
| RP11-71F17 | 11q13.3 | 69679241 | 11 | 69679241 | 69857706 | bacEndPairs.short |
| RP11-203N8 | 11q13.3 | 69696529 | 11 | 69696529 | 69848866 | fishClones.txt |
| RP11-948G5 | 11q13.3 | 69795403 | 11 | 69795403 | 69989958 | bacEndPairs.short |
| RP11-1146L22 | 11q13.3 | 69867349 | 11 | 69867349 | 70011262 | bacEndPairs.short |
| RP11-994L22 | 11q13.3 | 70010527 | 11 | 70010527 | 70224468 | bacEndPairs.short |
| | | | | CONTIG bp | 1311424 | |

| clone_ID | Accession # | BAC end seq. | BAC end seq | Gene/Marker | | | |
|---|---|---|---|---|---|---|---|
| RP11-378E8 | | AQ552193 | AQ552192 | | | | |
| RP11-825J6 | | AQ800956 | AQ814957 | | | | |
| RP11-266K14 | | AQ490826 | AQ490824 | | | | |
| RP11-300I6 | AP001888 | AQ507379 | AQ507376 | CCND1 | FGF4 | FGF19 | ORAOV1 |
| RP11-643C9 | | AQ410712 | AQ409271 | | | | |
| RP11-368I20 | | AQ527438 | AQ527441 | | | | |
| RP11-109F24 | AC079000 | AQ323038 | AQ350695 | | | | |
| RP11-71F17 | | AQ237008 | AQ268546 | | | | |
| RP11-203N8 | AP001787 | AQ413617 | AQ413618 | SHGC-147791 | TMEM16A | | |
| RP11-948G5 | | AQ571041 | AQ565413 | | | | |
| RP11-1146L22 | | AQ752089 | AQ742036 | | | | |
| RP11-994L22 | | AQ592148 | AQ662229 | | | | |

TABLE 4

20q13.1

| clone_ID | Cytoband_May04 | link_UCSC | May04_chr | UCSC Genome Browser May04_coor1 | UCSC Genome Browser May04_coor2 | MapType | Accession # |
|---|---|---|---|---|---|---|---|
| RP11-180A1 | 20q13.12 | 42569370 | 20 | 42569370 | 42768726 | bacEndPairs.short | |
| RP11-171L8 | 20q13.12 | 42708773 | 20 | 42708773 | 42877841 | bacEndPairs.short | |
| RP11-136D17 | 20q13.12 | 42863692 | 20 | 42863692 | 43011745 | bacEndPairs.short | |
| RP1-14BE22 | 20q13.12 | 42906926 | 20 | 42906926 | 42986153 | fishClones.txt | AL008725 |
| RP11-844G5 | 20q13.12 | 43007323 | | 43007323 | 43190392 | bacEndPairs.short | |
| RP11-158B5 | 20q13.12 | 43111838 | 20 | 43111838 | 43289508 | bacEndPairs.short | |
| RP11-316D9 | 20q13.12 | 43184398 | 20 | 43184398 | 43344433 | bacEndPairs.short | |
| RP11-1078E13 | 20q13.12 | 43317989 | 20 | 43317989 | 43519869 | bacEndPairs.short | |
| RP3-453C12 | 20q13.12 | 43350784 | 20 | 43350784 | 43498404 | fishClones.txt | AL021578 |
| RP3-461P17 | 20q13.12 | 43498302 | 20 | 43498302 | 43625329 | fishClones.txt | AL031663 |
| RP11-241P6 | 20q13.12 | 43503512 | | 43503512 | 43655407 | bacEndPairs.short | |
| RP11-140D6 | 20q13.12 | 43643212 | | 43643212 | 43840988 | bacEndPairs.short | |
| RP11-266P19 | 20q13.12 | 43768929 | 20 | 43768929 | 43934011 | bacEndPairs.short | |
| RP11-724M24 | 20q13.12 | 43804949 | 20 | 43804949 | 43996529 | bacEndPairs.short | |
| RP11-107K11 | 20q13.12 | 43972251 | 20 | 43972251 | 44130754 | bacEndPairs.short | |
| RP11-177B15 | 20q13.12 | 44111213 | | 44111213 | 44286886 | bacEndPairs.short | |
| RP11-108D14 | 20q13.12 | 44160652 | 20 | 44160652 | 44357055 | bacEndPairs.short | |

TABLE 4-continued

20q13.1

| | | | | | | |
|---|---|---|---|---|---|---|
| CTD-2357O14 | 20q13.12 | 44292739 | | 44292739 | 44394896 | bacEndPairs.short |
| RP11-75C17 | 20q13.12 | 44373450 | 20 | 44373450 | 44550339 | fishClones.txt |
| | | | | CONTIG bp | 1980969 | |

| clone_ID | BAC end seq. | BAC end seq | Gene/Marker | | | |
|---|---|---|---|---|---|---|
| RP11-180A1 | AQ414068 | AQ414067 | | | | |
| RP11-171L8 | AZ520284 | AZ520281 | | | | |
| RP11-136D17 | AQ383349 | AQ346171 | | | | |
| RP1-14BE22 | | | YWHAB | | | |
| RP11-844G5 | AQ818691 | AQ809877 | | | | |
| RP11-158B5 | AQ372601 | AQ372588 | | | | |
| RP11-316D9 | AQ540436 | AQ506842 | | | | |
| RP11-1078E13 | AQ743857 | AQ740407 | | | | |
| RP3-453C12 | | | MATN4 | SDC4 | PIGT | RBPSUHL C20orf10 C20orf35 |
| RP3-461P17 | | | WFDC2 | WFDC6 | WFDC8 | SPINLW1 |
| RP11-241P6 | AQ483184 | AQ483181 | | | | |
| RP11-140D6 | AQ383653 | AQ383656 | | | | |
| RP11-266P19 | AQ478366 | AQ478365 | | | | |
| RP11-724M24 | AQ616294 | AQ616208 | | | | |
| RP11-107K11 | AQ319936 | AQ319932 | | | | |
| RP11-177B15 | AQ418358 | AQ418360 | | | | |
| RP11-108D14 | AQ319129 | AQ348861 | | | | |
| CTD-2357O14 | AQ062439 | AQ062441 | | | | |
| RP11-75C17 | AQ266365 | AQ239123 | D20S836 | NIDDM3 | | |

TABLE 5

20q13.2

| clone_ID | Cytoband_May04 | link_UCSC | May04_chr | UCSC Genome Browser May04_coor1 | UCSC Genome Browser May04_coor2 |
|---|---|---|---|---|---|
| RP11-381I13 | 20q13.2 | 50752215 | 20 | 50752215 | 50907963 |
| RP11-1103E10 | 20q13.2 | 50937802 | 20 | 50937802 | 51109210 |
| RP11-15M15 | 20q13.2 | 51109651 | 20 | 51109651 | 51266852 |
| RP11-56N10 | 20q13.2 | 51188671 | 20 | 51188671 | 51356904 |
| RP11-765I11 | 20q13.2 | 51266873 | 20 | 51266873 | 51459601 |
| RP11-91L1 | 20q13.2 | 51421216 | 20 | 51421216 | 51572829 |
| RP4-724E16 | 20q13.2 | 51561510 | 20 | 51561510 | 51690363 |
| RP11-1057P5 | 20q13.2 | 51563366 | 20 | 51563366 | 51758197 |
| RP11-166M15 | 20q13.2 | 51721542 | 20 | 51721542 | 51879477 |
| RP11-159F20 | 20q13.2 | 51850650 | 20 | 51850650 | 52024597 |
| RP11-229P8 | 20q13.2 | 51920859 | 20 | 51920859 | 52096191 |
| RP11-368H3 | 20q13.2 | 52040931 | 20 | 52040931 | 52228711 |
| RP11-1F20 | 20q13.2 | 52157198 | 20 | 52157198 | 52331743 |
| RP11-945B10 | 20q13.2 | 52157210 | 20 | 52157210 | 52339105 |
| RP11-55L7 | 20q13.2 | 52354415 | | 52354415 | 52530584 |
| RP11-6L15 | 20q13.2 | 52483586 | 20 | 52483586 | 52655568 |
| | | | | CONTIG bp | 1,903,354 |

| clone_ID | MapType | Accession # | BAC end seq. | BAC end seq | Gene/Marker | |
|---|---|---|---|---|---|---|
| RP11-381I13 | bacEndPairs.short | | AQ552534 | AQ535756 | | |
| RP11-1103E10 | bacEndPairs.short | | AQ697033 | AQ677071 | | |
| RP11-15M15 | bacEndPairs.short | AL391097 | B83554 | B76563 | | |
| RP11-56N10 | bacEndPairs.short | | AQ115309 | AQ082530 | | |
| RP11-765I11 | bacEndPairs.short | | AQ519657 | AQ452763 | | |
| RP11-91L1 | fishClones.txt | | AQ283579 | AZ519337 | | |
| RP4-724E16 | fishClones.txt | AL157838 | | | ZNF217 | NIDDM3 |
| RP11-1057P5 | bacEndPairs.short | | AQ680772 | AQ673688 | | |
| RP11-166M15 | bacEndPairs.short | | AQ383230 | AQ383226 | | |
| RP11-159F20 | bacEndPairs.short | | AQ373570 | AQ373569 | | |
| RP11-229P8 | bacEndPairs.short | | AQ489432 | AQ489431 | | |
| RP11-368H3 | bacEndPairs.short | | AQ528880 | AQ528449 | | |
| RP11-1F20 | fishClones.txt | AC015742 | | | CYP24A1 | |
| RP11-945B10 | bacEndPairs.short | | AQ565288 | AQ723614 | | |
| RP11-55L7 | bacEndPairs.short | | AQ081779 | AQ081782 | | |
| RP11-6L15 | bacEndPairs.short | AL162292 | B49487 | B63518 | DOK5 | |

TABLE 6

20q13.3

| clone_ID | Cytoband_May04 | link_UCSC | May04_chr | UCSC Genome Browser May04_coor1 | UCSC Genome Browser May04_coor2 | MapType |
|---|---|---|---|---|---|---|
| RP5-885L7 | 20q13.33 | 60852620 | 20 | 60852620 | 61012861 | fishClones.txt |
| RP11-1005J21 | 20q13.33 | 61011745 | 20 | 61011745 | 61170179 | bacEndPairs.short |
| CTD-3051D12 | 20q13.33 | 61038964 | 20 | 61038964 | 61249909 | bacEndPairs.short |
| RP11-419M12 | 20q13.33 | 61266530 | 20 | 61266530 | 61443089 | bacEndPairs.short |
| RP11-1021O15 | 20q13.33 | 61500211 | 20 | 61500211 | 61721537 | baoEndPairs.short |
| RP11-358D14 | 20q13.33 | 61516417 | 20 | 61516417 | 61572892 | clonePos.txt |
| RP11-95N13 | 20q13.33 | 61564622 | 20 | 61564622 | 61727698 | bacEndPairs.short |
| RP4-697K14 | 20q13.33 | 61572792 | 20 | 61572792 | 61685988 | fishClones.txt |
| CTD-3104L22 | 20q13.33 | 61721547 | 20 | 61721547 | 61862002 | bacEndPairs.short |
| CTD-2270O20 | 20q13.33 | 61845303 | 20 | 61845303 | 61984905 | bacEndPairs.short |
| RP11-299N6 | 20q13.33 | 62163352 | 20 | 62163352 | 62196851 | clonePos.txt |
| RP5-1022E24 | 20q13.33 | 62196751 | 20 | 62196751 | 62376639 | clonePos.txt |
| RP11-266K16 | 20q13.33 | 62267315 | 20 | 62267315 | 62430362 | bacEndPairs.short |

| clone_ID | Accession # | BAC end seq. | BAC end seq | Gene/Marker | Gene/Marker | Gene/Marker |
|---|---|---|---|---|---|---|
| RP5-885L7 | AL035669 | | | TCFL5 | OGFR | DATF1 |
| RP11-1005J21 | | AQ715500 | AQ715668 | | | |
| CTD-3051D12 | | AQ134307 | AQ134476 | | | |
| RP11-419M12 | | AQ553273 | AQ553276 | | | |
| RP11-1021O15 | | AQ697703 | AQ720219 | | | |
| RP11-358D14 | AL353658 | AQ542313 | AQ542315 | KCNQ2 | | |
| RP11-95N13 | | AQ315671 | AQ315674 | | | |
| RP4-697K14 | AL121829 | | | EEF1A2 | PTK6 | KCNQ2 |
| CTD-3104L22 | | AQ123749 | EEF1A2 | | | |
| CTD-2270O20 | | AQ164110 | AQ496954 | | | |
| RP11-299N6 | AL590548 | AQ506334 | | RGS19 | OPRL1 | TCEA2 |
| RP5-1022E24 | AL121581 | | | GPR8 | MYT1 | OPRL1 |
| RP11-266K16 | | AQ490829 | AQ490833 | | | |

What is claimed is:

1. A composition comprising:

an RNA interference oligonucleotide inhibitor of PVT1 expression adapted for interacting with an RNA sequence at locus 8q24 of a human chromosome, and a pharmaceutically acceptable carrier, wherein the RNA interference inhibitor is capable of inhibiting PVT1 expression in an ovarian tumor cell having elevated PVT1 expression, wherein the RNA interference inhibitor comprises double-stranded siRNA oligonucleotide selected from the group consisting of SEQ ID NOS: 3 and 4, wherein the siRNA oligonucleotide is adapted to act at a sequence comprises an overlapping region of M34428 (SEQ ID NO:1) and a coding portion of XM_372058 predicted coding region, base pairs 379 to 777 (SEQ ID NO:2), and wherein the siRNA oligonucleotide is 18-22 nucleotide bases in length.

2. A kit for treating a patient having ovarian cancer comprising:

reagents and components for detecting an elevated expression of a PVT1 gene in an ovarian tumor cell of the patient, wherein poor responsiveness to platinum taxane therapy predicted upon detection of elevated expression of the PVT1 gene in the tumor cell, and wherein one of said reagents comprises an RNA interference oligonucleotide inhibitor of PVT1 gene expression, wherein the RNA interference oligonucleotide inhibitor comprising a double-stranded selected from the group consisting of SEQ ID NOS: 3 and 4, wherein the siRNA oligonucleotide is adapted to act at a sequence comprises an overlapping region of M34428 (SEQ ID NO:1) and a coding portion of XM_372058 predicted coding region, base pairs 379 to 777 (SEQ ID NO:2), and wherein the siRNA oligonucleotide is 18-22 nucleotide bases in length.

3. The kit of claim 2, further comprising information to provide patient access to a therapeutic composition comprising an inhibitor of PVT1 gene expression in a pharmaceutically acceptable carrier for administering the therapeutic composition to the patient to treat the ovarian cancer, upon detection of elevated expression of the PVT1 gene in the patient.

* * * * *